US009764022B2

(12) United States Patent
Buck et al.

(10) Patent No.: US 9,764,022 B2
(45) Date of Patent: Sep. 19, 2017

(54) METHODS AND COMPOSITIONS FOR INHIBITING POLYOMAVIRUS-ASSOCIATED PATHOLOGY

(75) Inventors: Christopher B. Buck, Bethesda, MD (US); Diana V. Pastrana, Arlington, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/233,582

(22) PCT Filed: Jul. 17, 2012

(86) PCT No.: PCT/US2012/047069
§ 371 (c)(1),
(2), (4) Date: Jan. 17, 2014

(87) PCT Pub. No.: WO2013/012866
PCT Pub. Date: Jan. 24, 2013

(65) Prior Publication Data

US 2014/0154284 A1 Jun. 5, 2014

Related U.S. Application Data

(60) Provisional application No. 61/508,897, filed on Jul. 18, 2011.

(51) Int. Cl.

| | |
|---|---|
| ***A61K 39/12*** | (2006.01) |
| ***C12N 7/00*** | (2006.01) |
| ***C12Q 1/70*** | (2006.01) |
| ***G01N 33/569*** | (2006.01) |
| *A61K 39/00* | (2006.01) |

(52) U.S. Cl.
CPC ................ *A61K 39/12* (2013.01); *C12N 7/00* (2013.01); *C12Q 1/70* (2013.01); *G01N 33/56983* (2013.01); *A61K 2039/5258* (2013.01); *A61K 2039/55566* (2013.01); *A61K 2039/70* (2013.01); *C12N 2710/22023* (2013.01); *C12N 2710/22034* (2013.01); *G01N 2333/025* (2013.01); *G01N 2469/20* (2013.01); *G01N 2800/347* (2013.01)

(58) Field of Classification Search
None
See application file for complete search history.

(56) References Cited

U.S. PATENT DOCUMENTS

| | | | | |
|---|---|---|---|---|
| 5,213,796 | A | 5/1993 | Garcea et al. | |
| 6,238,859 | B1 | 5/2001 | Luke et al. | |
| 2003/0099668 | A1 * | 5/2003 | Bachmann et al. | ....... 424/204.1 |
| 2007/0026503 | A1 | 2/2007 | Lacey | |
| 2008/0057079 | A1 | 3/2008 | Boland | |

FOREIGN PATENT DOCUMENTS

| | | |
|---|---|---|
| WO | WO 2009/105212 | 8/2009 |
| WO | WO 2010/090757 | 8/2010 |

OTHER PUBLICATIONS

Vlastos Franzen, Murine polyomavirus VP1 virus-like particles as vectors for gene therapy and as vaccines against polyomavirus infection and tumors, Jun. 11, 2004, Abstract.*
Sharma et al., Virology, 2006, 350:128-136.*
Krumbholz et al., Infection, Genetics and Evolution, 2008, 8:632-643.*
GenBank Accession No. BAG84476; Nov. 19, 2008.*
GenBank Accession No. CAA40239; Apr. 21, 1993.*
Chen et al., Arch. Virol., 2006, 151: 2419-2429.*
GenBank Accession No. BAF03085 (Aug. 18, 2006).*
Zhong et al., Journal of General Virology, 2009, 90:144-152.*
Abend et al., "BK Virus and Human Cancer: Innocent until Proven Guilty," *Seminars in Cancer Biology*, vol. 19, pp. 252-260, 2009.
"Bk Virus," *Am. J. Transpl.* vol. 4, Suppl. 10, pp. 89-91, 2004.
Bohl et al., "Donor Origin of BK Virus in Renal Transplantation and Role of HLA C7 in Susceptibility to Sustained BK Viremia," *Am. J. Transpl.* vol. 5, pp. 2213-2221, 2005.
Bohl et al., "BK Virus Antibody Titers and Intensity of Infections after Renal Transplantation," *J. Clin. Virol.*, vol. 43, pp. 184-189, 2008.
Capture-CMV, Solid Phase System for the Detection of IgG and IgM Antibodies to Cytomegalovirus (CMV), Immucor, 2011 (4 pages).
Dheir et al., "Intensive Polyoma Virus Nephropathy Treatment as a Preferable Approach for Graft Surveillance," *Transplantation Proceedings*, vol. 43, No. 3, pp. 867-870, 2011.
Flaegstad et al., "Neutralization test for BK virus: plaque reduction detected by immunoperoxidase staining," *Journal of Medical Virology*, vol. 19, No. 3, pp. 287-296, 1986.

(Continued)

*Primary Examiner* — Nicole Kinsey White

(74) *Attorney, Agent, or Firm* — Klarquist Sparkman, LLP

(57) ABSTRACT

Disclosed herein are methods of eliciting an immune response against a polyomavirus (for example, BKV serotype I (BKV-I), BKV serotype II (BKV-II), BKV serotype III (BKV-III) and/or BKV serotype IV (BKV-IV)) and methods of treating or inhibiting polyomavirus-associated pathology (such as polyomavirus-associated nephropathy, BKV-associated hemorrhagic cystitis, or JC virus-associated progressive multifocal leukoencephalopathy; PML). Further disclosed are immunogenic compositions of use in the disclosed methods. Also disclosed are methods of selecting an organ transplant donor and/or recipient including detecting whether the prospective donor and/or recipient has BKV serotype-specific (such as BKV serotype IV-specific) neutralizing antibodies.

25 Claims, 19 Drawing Sheets

(56) References Cited

OTHER PUBLICATIONS

Gordon et al., “Prevalence of rare BKV serotypes and donor vs. recipient mismatch in polyomavirus nephropathy,” *Journal of Neurovirology*, vol. 14, No. Suppl. 2, p. 27, 2005.
Joint Working Party of the British Transplantation Society and the Renal Association, “United Kingdom Guidelines for Living Donor Kidney Transplantation,” pp. 104-109, 2011.
Knowles et al., “Serological Typing Scheme for BK-Like Isolates of Human Polyomavirus,” *J. Med. Virol.* vol. 28, pp. 118-123, 1989.
Krumbholz et al., “Prevalence of BK Virus Subtype I in Germany,” *J. Med. Virol.* vol. 78, pp. 1588-1598, 2006.
Krumbholz et al., “Evolution of four BK virus subtypes,” *Infection, Genetics and Evolution*, vol. 8, No. 5, pp. 632-643, 2008.
Marfo et al., “Desensitization Protocols and Their Outcome,” *Clin. J. Am. Soc. Nephrol.*, vol. 6, pp. 922-936, 2011.
Nakanishi et al., “SV40 vectors carrying minimal sequence of viral origin with exchangeable capsids,” *Virology*, vol. 379, pp. 110-117, 2008.
Pastrana et al., “Quantitation of Human Seroresponsiveness to Merkel Cell Polyomavirus,” *PLoS Pathogens* vol. 5, No. 9, e1000578, 2009 (11 pages).
Pastrana et al., “Neutralization Serotyping of BK Polyomavirus Infection in Kidney Transplant Recipients,” *PLoS Pathogens*, vol. 8, No. 4, e1002650, 2012 (11 pages).
Pastrana et al., “BK Polyomavirus Genotypes Represent Distinct Serotypes with Distinct Entry Tropism,” *J. Virol.* vol. 87, pp. 10105-10113, 2013.
Puliyanda et al., “IVIG Contains Antibodies Reactive with Polyoma BK Virus and May Represent a Therapeutic Option for BK Nephropathy,” *Am. J. Transpl.* vol. 3, Suppl. 3, pp. 393, 2001.
Randhawa et al., “Immunoglobulin G, A, and M Responses to BK Virus in Renal Transplantation,” *Clin. Vaccine Immunol.* vol. 13, No. 9, pp. 1057-1063, 2006.
Randhawa et al., “Longitudinal Analysis of Levels of Immunoglobulins against BK Virus Capsid Proteins in Kidney Transplant Recipients,” *Clin. Vaccine Immunol.* vol. 15, No. 10, pp. 1564-1571, 2008.
Randhawa et al., “Polyomavirus BK neutralizing activity in human immunoglobulin preparations,” *Transplantation*, vol. 89, No. 12, pp. 1462-1465, 2010 (author manuscript version, 8 pages).
Randhawa, “Vaccine Development for Polyomavirus BK,” *Kidney Research National Dialogue*, 2011 (2 pages).
Reid et al., “Sequencing and Analysis of JC Virus DNA from Natalizumab-Treated PML Patients,” *J. Infectious Dis.* vol. 204, pp. 237-244, 2011.
Sener et al., “Intravenous immunoglobulin as a treatment for BK virus associated nephropathy: one-year follow-up of renal allograft recipients,” *Transplantation*, vol. 81, No. 1, pp. 117-120, 2006.
Shah et al., “Serological investigation of BK papovavirus infection in pregnant women and their offspring,” *Infection and Immunity*, vol. 30, No. 1, pp. 29-35, 1980.
Sharma et al., “Intravenous immunoglobulin as rescue therapy for BK virus nephropathy,” *Pediatric Transplantation*, vol. 13, No. 1, pp. 123-129, 2009.
Smith and Davis, “Screening for BK virus in pediatric renal transplant recipients,” *Pediatric Transplantation*, vol. 14, pp. 559-560, 2010.
Sunyaev et al., “Adaptive Mutation in the JC Virus Protein Capsid are Associated with Progressive Multifocal Leukoencephalopathy (PML),” *PLoS Genetics*, vol. 5, No. 2, e1000368, 2009 (7 pages).
Takayama et al., “BK virus subtype IV nephropathy occurring 5 years after kidney transplantation,” *Clin. Exp. Nephrol.*, vol. 11, pp. 102-106, 2007.
Tremolada et al., “Rare subtypes of BK virus are viable and frequently detected in renal transplant recipients with BK virus-associated nephropathy,” *Virology*, vol. 404, No. 2, pp. 312-318, 2010.
Tremolada et al., “Polymorphisms of the BK Virus Subtypes and their Influence on Viral In Vitro Growth Efficiency,” *Virus Res.* vol. 149, pp. 190-196, 2010.
Viscidi et al., “Serological Cross-Reactivities between Antibodies to Simian Virus 40, BK Virus, and JC Virus Assessed by Virus-Like Particle-Based Enzyme Immunoassays,” *Clin. Diagnos. Lab. Immunol.* vol. 10, No. 2, pp. 278-285, 2003.
Wadei et al., “Kidney Transplant Function and Histological Clearance of Virus Following Diagnosis of Polyomavirus-Associated Nephropathy (PVAN),” *Am. J. Transpl.* vol. 6, pp. 1025-1032, 2006.

* cited by examiner

SEQUENCE LISTING

<160> NUMBER OF SEQ ID NOS: 158

<210> SEQ ID NO 1
<211> LENGTH: 362
<212> TYPE: PRT
<213> ORGANISM: BK virus

<400> SEQUENCE: 1

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 2
<211> LENGTH: 351
<212> TYPE: PRT
<213> ORGANISM: BK virus

<400> SEQUENCE: 2

```
Met Gly Ala Ala Leu Ala Leu Leu Gly Asp Leu Val Ala Ser Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Ile Ala Ser Leu Ala Thr Val
        35                  40                  45

Glu Gly Ile Thr Ser Thr Ser Glu Ala Leu Ala Ala Ile Gly Leu Thr
    50                  55                  60

Pro Gln Thr Tyr Ala Val Ile Ala Gly Ala Pro Gly Ala Ile Ala Gly
65                  70                  75                  80

Phe Ala Ala Leu Ile Gln Thr Val Thr Gly Ile Ser Ser Leu Ala Gln
                85                  90                  95

Val Gly Tyr Arg Phe Phe Ser Asp Trp Asp His Lys Val Ser Thr Val
            100                 105                 110

Gly Leu Tyr Gln Gln Ser Gly Met Ala Leu Glu Leu Phe Asn Pro Asp
        115                 120                 125

Glu Tyr Tyr Asp Ile Leu Phe Pro Gly Val Asn Thr Phe Val Asn Asn
    130                 135                 140

Ile Gln Tyr Leu Asp Pro Arg His Trp Gly Pro Ser Leu Phe Ala Thr
145                 150                 155                 160

Ile Ser Gln Ala Leu Trp His Val Ile Arg Asp Asp Ile Pro Ala Ile
                165                 170                 175

Thr Ser Gln Glu Leu Gln Arg Arg Thr Glu Arg Phe Phe Arg Asp Ser
            180                 185                 190

Leu Ala Arg Phe Leu Glu Glu Thr Thr Trp Thr Ile Val Asn Ala Pro
        195                 200                 205

Ile Asn Phe Tyr Asn Tyr Ile Gln Glu Tyr Val Ser Asp Leu Ser Pro
    210                 215                 220

Ile Arg Pro Ser Met Val Arg Gln Val Ala Glu Arg Glu Gly Thr Arg
225                 230                 235                 240

Val His Phe Gly His Thr Tyr Ser Ile Asp Asp Ala Asp Ser Ile Glu
                245                 250                 255

Glu Val Thr Gln Arg Met Asp Leu Arg Asn Gln Gln Thr Val His Ser
            260                 265                 270

Gly Glu Phe Ile Glu Lys Thr Ile Ala Pro Gly Gly Ala Asn Gln Arg
        275                 280                 285

Thr Ala Pro Gln Trp Met Leu Pro Leu Leu Leu Gly Leu Tyr Gly Thr
    290                 295                 300

Val Thr Pro Ala Leu Glu Ala Tyr Glu Asp Gly Pro Asn Gln Lys Lys
305                 310                 315                 320

Arg Arg Val Ser Arg Gly Ser Ser Gln Lys Ala Lys Gly Thr Arg Ala
                325                 330                 335

Ser Ala Lys Thr Thr Asn Lys Arg Arg Ser Arg Ser Ser Arg Ser
            340                 345                 350
```

<210> SEQ ID NO 3
<211> LENGTH: 232
<212> TYPE: PRT
<213> ORGANISM: BK virus

<400> SEQUENCE: 3

```
Met Ala Leu Glu Leu Phe Asn Pro Asp Glu Tyr Tyr Asp Ile Leu Phe
1               5                   10                  15

Pro Gly Val Asn Thr Phe Val Asn Asn Ile Gln Tyr Leu Asp Pro Arg
            20                  25                  30

His Trp Gly Pro Ser Leu Phe Ala Thr Ile Ser Gln Ala Leu Trp His
        35                  40                  45

Val Ile Arg Asp Asp Ile Pro Ala Ile Thr Ser Gln Glu Leu Gln Arg
    50                  55                  60

Arg Thr Glu Arg Phe Phe Arg Asp Ser Leu Ala Arg Phe Leu Glu Glu
65                  70                  75                  80

Thr Thr Trp Thr Ile Val Asn Ala Pro Ile Asn Phe Tyr Asn Tyr Ile
                85                  90                  95

Gln Glu Tyr Tyr Ser Asp Leu Ser Pro Ile Arg Pro Ser Met Val Arg
            100                 105                 110

Gln Val Ala Glu Arg Glu Gly Thr Arg Val His Phe Gly His Thr Tyr
        115                 120                 125

Ser Ile Asp Asp Ala Asp Ser Ile Glu Glu Val Thr Gln Arg Met Asp
    130                 135                 140

Leu Arg Asn Gln Gln Thr Val His Ser Gly Glu Phe Ile Glu Lys Thr
145                 150                 155                 160

Ile Ala Pro Gly Gly Ala Asn Gln Arg Thr Ala Pro Gln Trp Met Leu
                165                 170                 175

Pro Leu Leu Leu Gly Leu Tyr Gly Thr Val Thr Pro Ala Leu Glu Ala
            180                 185                 190

Tyr Glu Asp Gly Pro Asn Gln Lys Lys Arg Arg Val Ser Arg Gly Ser
        195                 200                 205

Ser Gln Lys Ala Lys Gly Thr Arg Ala Ser Ala Lys Thr Thr Asn Lys
    210                 215                 220

Arg Arg Ser Arg Ser Ser Arg Ser
225                 230
```

<210> SEQ ID NO 4
<211> LENGTH: 362
<212> TYPE: PRT
<213> ORGANISM: BK virus

<400> SEQUENCE: 4

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125
```

```
Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Lys Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 5
<211> LENGTH: 351
<212> TYPE: PRT
<213> ORGANISM: BK virus

<400> SEQUENCE: 5

Met Gly Ala Ala Leu Ala Leu Leu Gly Asp Leu Val Ala Ser Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Ile Ala Ser Leu Ala Thr Val
        35                  40                  45

Glu Gly Ile Thr Ser Thr Ser Glu Ala Ile Ala Ala Ile Gly Leu Thr
    50                  55                  60

Pro Gln Thr Tyr Ala Val Ile Ala Gly Ala Pro Gly Ala Ile Ala Gly
65                  70                  75                  80

Phe Ala Ala Leu Ile Gln Thr Val Thr Gly Ile Ser Ser Leu Ala Gln
                85                  90                  95

Val Gly Tyr Arg Phe Phe Ser Asp Trp Asp His Lys Val Ser Thr Val
            100                 105                 110

Gly Leu Tyr Gln Gln Ser Gly Met Ala Leu Glu Leu Phe Asn Pro Asp
        115                 120                 125

Glu Tyr Tyr Asp Ile Leu Phe Pro Gly Val Asn Thr Phe Val Asn Asn
```

-continued 130 135 140

Ile Gln Tyr Leu Asp Pro Arg His Trp Gly Pro Ser Leu Phe Ala Thr
145 150 155 160

Ile Ser Gln Ala Leu Trp His Val Ile Arg Asp Asp Ile Pro Ala Ile
165 170 175

Thr Ser Gln Glu Leu Gln Arg Arg Thr Glu Arg Phe Phe Arg Asp Ser
180 185 190

Leu Ala Arg Phe Leu Glu Glu Thr Thr Trp Thr Ile Val Asn Ala Pro
195 200 205

Val Asn Phe Tyr Asn Tyr Ile Gln Asp Tyr Tyr Ser Asn Leu Ser Pro
210 215 220

Ile Arg Pro Ser Met Val Arg Gln Val Ala Glu Arg Glu Gly Thr Gln
225 230 235 240

Val Asn Phe Gly His Thr Tyr Arg Ile Asp Asp Ala Asp Ser Ile Gln
245 250 255

Glu Val Thr Gln Arg Met Glu Leu Arg Asn Lys Glu Asn Val His Ser
260 265 270

Gly Glu Phe Ile Glu Lys Thr Ile Ala Pro Gly Gly Ala Asn Gln Arg
275 280 285

Thr Ala Pro Gln Trp Met Leu Pro Leu Leu Leu Gly Leu Tyr Gly Thr
290 295 300

Val Thr Pro Ala Leu Glu Ala Tyr Glu Asp Gly Pro Asn Gln Lys Lys
305 310 315 320

Arg Arg Val Ser Arg Gly Ser Ser Gln Lys Ala Lys Gly Thr Arg Ala
325 330 335

Ser Ala Lys Thr Thr Asn Lys Arg Arg Ser Arg Ser Ser Arg Ser
340 345 350

<210> SEQ ID NO 6
<211> LENGTH: 232
<212> TYPE: PRT
<213> ORGANISM: BK virus

<400> SEQUENCE: 6

Met Ala Leu Glu Leu Phe Asn Pro Asp Glu Tyr Tyr Asp Ile Leu Phe
1 5 10 15

Pro Gly Val Asn Thr Phe Val Asn Asn Ile Gln Tyr Leu Asp Pro Arg
20 25 30

His Trp Gly Pro Ser Leu Phe Ala Thr Ile Ser Gln Ala Leu Trp His
35 40 45

Val Ile Arg Asp Asp Ile Pro Ala Ile Thr Ser Gln Glu Leu Gln Arg
50 55 60

Arg Thr Glu Arg Phe Phe Arg Asp Ser Leu Ala Arg Phe Leu Glu Glu
65 70 75 80

Thr Thr Trp Thr Ile Val Asn Ala Pro Val Asn Phe Tyr Asn Tyr Ile
85 90 95

Gln Asp Tyr Tyr Ser Asn Leu Ser Pro Ile Arg Pro Ser Met Val Arg
100 105 110

Gln Val Ala Glu Arg Glu Gly Thr Gln Val Asn Phe Gly His Thr Tyr
115 120 125

Arg Ile Asp Asp Ala Asp Ser Ile Gln Glu Val Thr Gln Arg Met Glu
130 135 140

Leu Arg Asn Lys Glu Asn Val His Ser Gly Glu Phe Ile Glu Lys Thr
145 150 155 160

-continued

```
Ile Ala Pro Gly Gly Ala Asn Gln Arg Thr Ala Pro Gln Trp Met Leu
                165                 170                 175

Pro Leu Leu Leu Gly Leu Tyr Gly Thr Val Thr Pro Ala Leu Glu Ala
            180                 185                 190

Tyr Glu Asp Gly Pro Asn Gln Lys Lys Arg Arg Val Ser Arg Gly Ser
        195                 200                 205

Ser Gln Lys Ala Lys Gly Thr Arg Ala Ser Ala Lys Thr Thr Asn Lys
    210                 215                 220

Arg Arg Ser Arg Ser Ser Arg Ser
225                 230


<210> SEQ ID NO 7
<211> LENGTH: 362
<212> TYPE: PRT
<213> ORGANISM: BK virus

<400> SEQUENCE: 7

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Lys Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300
```

```
Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 8
<211> LENGTH: 351
<212> TYPE: PRT
<213> ORGANISM: BK virus

<400> SEQUENCE: 8

Met Gly Ala Ala Leu Ala Leu Leu Gly Asp Leu Val Ala Ser Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Ile Ala Ser Leu Ala Thr Val
        35                  40                  45

Glu Gly Ile Thr Thr Thr Ser Glu Ala Ile Ala Ala Ile Gly Leu Thr
    50                  55                  60

Pro Gln Thr Tyr Ala Val Ile Ala Gly Ala Pro Gly Ala Ile Ala Gly
65                  70                  75                  80

Phe Ala Ala Leu Ile Gln Thr Val Thr Gly Ile Ser Ser Leu Ala Gln
                85                  90                  95

Val Gly Tyr Arg Phe Phe Ser Asp Trp Asp His Lys Val Ser Thr Val
            100                 105                 110

Gly Leu Tyr Gln Gln Ser Gly Met Ala Leu Glu Leu Phe Asn Pro Asp
        115                 120                 125

Glu Tyr Tyr Asp Ile Leu Phe Pro Gly Val Asn Thr Phe Val Asn Asn
    130                 135                 140

Ile Gln Tyr Leu Asp Pro Arg His Trp Gly Pro Ser Leu Phe Ala Thr
145                 150                 155                 160

Ile Ser Gln Ala Leu Trp His Val Ile Arg Asp Asp Ile Pro Ala Ile
                165                 170                 175

Thr Ser Gln Glu Leu Gln Arg Arg Thr Glu Arg Phe Phe Arg Asp Ser
            180                 185                 190

Leu Ala Arg Phe Leu Glu Glu Thr Thr Trp Thr Ile Val Asn Ala Pro
        195                 200                 205

Val Asn Phe Tyr Asn Tyr Ile Gln Asp Tyr Tyr Ser Asn Leu Ser Pro
    210                 215                 220

Ile Arg Pro Ser Met Val Arg Gln Val Ala Glu Arg Glu Gly Thr His
225                 230                 235                 240

Val Asn Phe Gly His Thr Tyr Ser Ile Asp Asp Ala Asp Ser Ile Glu
                245                 250                 255

Glu Val Thr Gln Arg Ile Glu Leu Arg Asn Lys Glu Ser Val His Ser
            260                 265                 270

Gly Glu Phe Ile Glu Lys Thr Ile Ala Pro Gly Gly Ala Asn Gln Arg
        275                 280                 285

Thr Ala Pro Gln Trp Met Leu Pro Leu Leu Leu Gly Leu Tyr Gly Thr
    290                 295                 300

Val Thr Pro Ala Leu Glu Ala Tyr Glu Asp Gly Pro Asn Gln Lys Lys
```

305 310 315 320

Arg Arg Val Ser Arg Gly Ser Ser Gln Lys Ala Lys Gly Thr Arg Ala
325 330 335

Ser Ala Lys Thr Thr Asn Lys Arg Arg Ser Arg Ser Ser Arg Ser
340 345 350

<210> SEQ ID NO 9
<211> LENGTH: 232
<212> TYPE: PRT
<213> ORGANISM: BK virus

<400> SEQUENCE: 9

Met Ala Leu Glu Leu Phe Asn Pro Asp Glu Tyr Tyr Asp Ile Leu Phe
1 5 10 15

Pro Gly Val Asn Thr Phe Val Asn Asn Ile Gln Tyr Leu Asp Pro Arg
20 25 30

His Trp Gly Pro Ser Leu Phe Ala Thr Ile Ser Gln Ala Leu Trp His
35 40 45

Val Ile Arg Asp Asp Ile Pro Ala Ile Thr Ser Gln Glu Leu Gln Arg
50 55 60

Arg Thr Glu Arg Phe Phe Arg Asp Ser Leu Ala Arg Phe Leu Glu Glu
65 70 75 80

Thr Thr Trp Thr Ile Val Asn Ala Pro Val Asn Phe Tyr Asn Tyr Ile
85 90 95

Gln Asp Tyr Tyr Ser Asn Leu Ser Pro Ile Arg Pro Ser Met Val Arg
100 105 110

Gln Val Ala Glu Arg Glu Gly Thr His Val Asn Phe Gly His Thr Tyr
115 120 125

Ser Ile Asp Asp Ala Asp Ser Ile Glu Glu Val Thr Gln Arg Ile Glu
130 135 140

Leu Arg Asn Lys Glu Ser Val His Ser Gly Glu Phe Ile Glu Lys Thr
145 150 155 160

Ile Ala Pro Gly Gly Ala Asn Gln Arg Thr Ala Pro Gln Trp Met Leu
165 170 175

Pro Leu Leu Leu Gly Leu Tyr Gly Thr Val Thr Pro Ala Leu Glu Ala
180 185 190

Tyr Glu Asp Gly Pro Asn Gln Lys Lys Arg Arg Val Ser Arg Gly Ser
195 200 205

Ser Gln Lys Ala Lys Gly Thr Arg Ala Ser Ala Lys Thr Thr Asn Lys
210 215 220

Arg Arg Ser Arg Ser Ser Arg Ser
225 230

<210> SEQ ID NO 10
<211> LENGTH: 362
<212> TYPE: PRT
<213> ORGANISM: BK virus

<400> SEQUENCE: 10

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asp His Leu Arg

```
    50                  55                  60

Gly Tyr Ser Gln His Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Lys Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 11
<211> LENGTH: 351
<212> TYPE: PRT
<213> ORGANISM: BK virus

<400> SEQUENCE: 11

Met Gly Ala Ala Leu Ala Leu Leu Gly Asp Leu Val Ala Ser Val Ser
1               5                   10                  15

Glu Ala Ala Ala Ala Thr Gly Phe Ser Val Ala Glu Ile Ala Ala Gly
            20                  25                  30

Glu Ala Ala Ala Ala Ile Glu Val Gln Ile Ala Ser Leu Ala Thr Val
        35                  40                  45

Glu Gly Ile Thr Thr Thr Ser Glu Ala Ile Ala Ala Ile Gly Leu Thr
    50                  55                  60
```

-continued

```
Pro Gln Thr Tyr Ala Val Ile Ala Gly Ala Pro Gly Ala Ile Ala Gly
65                  70                  75                  80

Phe Ala Ala Leu Ile Gln Thr Val Thr Gly Ile Ser Ser Leu Ala Gln
                85                  90                  95

Val Gly Tyr Arg Phe Phe Ser Asp Trp Asp His Lys Val Ser Thr Val
            100                 105                 110

Gly Leu Tyr Gln Gln Ser Gly Met Ala Leu Glu Leu Phe Asn Pro Asp
        115                 120                 125

Glu Tyr Tyr Asp Ile Leu Phe Pro Gly Val Asn Thr Phe Val Asn Asn
    130                 135                 140

Ile Gln Tyr Leu Asp Pro Arg His Trp Gly Pro Ser Leu Phe Ala Thr
145                 150                 155                 160

Ile Ser Gln Ala Leu Trp His Val Ile Arg Asp Asp Ile Pro Ala Ile
                165                 170                 175

Thr Ser Gln Glu Leu Gln Arg Arg Thr Glu Arg Phe Phe Arg Asp Ser
            180                 185                 190

Leu Ala Arg Phe Leu Glu Glu Thr Thr Trp Thr Ile Val Asn Ala Pro
        195                 200                 205

Ile Asn Phe Tyr Asn Tyr Ile Gln Asp Tyr Tyr Ser Asn Leu Ser Pro
    210                 215                 220

Ile Arg Pro Ser Met Val Arg Gln Val Ala Glu Arg Glu Gly Thr His
225                 230                 235                 240

Val Asn Phe Gly His Thr Tyr Ser Ile Asp Asn Ala Asp Ser Ile Glu
                245                 250                 255

Glu Val Thr Gln Arg Met Asp Leu Arg Asn Lys Glu Ser Val His Ser
            260                 265                 270

Gly Glu Phe Ile Glu Lys Thr Ile Ala Pro Gly Gly Ala Asn Gln Arg
        275                 280                 285

Thr Ala Pro Gln Trp Met Leu Pro Leu Leu Leu Gly Leu Tyr Gly Thr
    290                 295                 300

Val Thr Pro Ala Leu Glu Ala Tyr Glu Asp Gly Pro Asn Gln Lys Lys
305                 310                 315                 320

Arg Arg Val Ser Arg Gly Ser Ser Gln Lys Ala Lys Gly Thr Arg Ala
                325                 330                 335

Ser Ala Lys Thr Thr Asn Lys Arg Arg Ser Arg Ser Ser Arg Ser
            340                 345                 350


<210> SEQ ID NO 12
<211> LENGTH: 232
<212> TYPE: PRT
<213> ORGANISM: BK virus

<400> SEQUENCE: 12

Met Ala Leu Glu Leu Phe Asn Pro Asp Glu Tyr Tyr Asp Ile Leu Phe
1               5                   10                  15

Pro Gly Val Asn Thr Phe Val Asn Asn Ile Gln Tyr Leu Asp Pro Arg
            20                  25                  30

His Trp Gly Pro Ser Leu Phe Ala Thr Ile Ser Gln Ala Leu Trp His
        35                  40                  45

Val Ile Arg Asp Asp Ile Pro Ala Ile Thr Ser Gln Glu Leu Gln Arg
    50                  55                  60

Arg Thr Glu Arg Phe Phe Arg Asp Ser Leu Ala Arg Phe Leu Glu Glu
65                  70                  75                  80

Thr Thr Trp Thr Ile Val Asn Ala Pro Ile Asn Phe Tyr Asn Tyr Ile
                85                  90                  95
```

-continued

```
Gln Asp Tyr Tyr Ser Asn Leu Ser Pro Ile Arg Pro Ser Met Val Arg
            100                 105                 110

Gln Val Ala Glu Arg Glu Gly Thr His Val Asn Phe Gly His Thr Tyr
        115                 120                 125

Ser Ile Asp Asn Ala Asp Ser Ile Glu Glu Val Thr Gln Arg Met Asp
    130                 135                 140

Leu Arg Asn Lys Glu Ser Val His Ser Gly Glu Phe Ile Glu Lys Thr
145                 150                 155                 160

Ile Ala Pro Gly Gly Ala Asn Gln Arg Thr Ala Pro Gln Trp Met Leu
                165                 170                 175

Pro Leu Leu Leu Gly Leu Tyr Gly Thr Val Thr Pro Ala Leu Glu Ala
            180                 185                 190

Tyr Glu Asp Gly Pro Asn Gln Lys Lys Arg Arg Val Ser Arg Gly Ser
        195                 200                 205

Ser Gln Lys Ala Lys Gly Thr Arg Ala Ser Ala Lys Thr Thr Asn Lys
    210                 215                 220

Arg Arg Ser Arg Ser Ser Arg Ser
225                 230


<210> SEQ ID NO 13
<211> LENGTH: 362
<212> TYPE: PRT
<213> ORGANISM: BK virus

<400> SEQUENCE: 13

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
```

-continued 225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Arg Leu Pro Gly Asp Pro Asp Met Ile Arg Tyr Ile Asp
340 345 350

Lys Gln Gly Gln Leu Gln Thr Lys Met Leu
355 360

<210> SEQ ID NO 14
<211> LENGTH: 362
<212> TYPE: PRT
<213> ORGANISM: BK virus

<400> SEQUENCE: 14

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Leu Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Ala Lys Asn Asp Phe Ser Ser Asp Ser
65 70 75 80

Pro Asp Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Phe Thr Gly Gly Glu Asn Val Pro Pro Val Leu His Val Thr Asn Thr
225 230 235 240

```
Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 15
<211> LENGTH: 362
<212> TYPE: PRT
<213> ORGANISM: BK virus

<400> SEQUENCE: 15

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Val Glu Asn Asp Phe Ser Ser Asp Ser
65                  70                  75                  80

Pro Gln Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255
```

```
Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 16
<211> LENGTH: 362
<212> TYPE: PRT
<213> ORGANISM: BK virus

<400> SEQUENCE: 16

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asn Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Asp Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
```

```
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 17
<211> LENGTH: 354
<212> TYPE: PRT
<213> ORGANISM: JC virus

<400> SEQUENCE: 17

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270
```

```
Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu


<210> SEQ ID NO 18
<211> LENGTH: 344
<212> TYPE: PRT
<213> ORGANISM: JC virus

<400> SEQUENCE: 18

Met Gly Ala Ala Leu Ala Leu Leu Gly Asp Leu Val Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Thr Ile Glu Val Glu Ile Ala Ser Leu Ala Thr Val
        35                  40                  45

Glu Gly Ile Thr Ser Thr Ser Glu Ala Ile Ala Ala Ile Gly Leu Thr
    50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

Gly Leu Phe Gln Gln Pro Ala Met Ala Leu Gln Leu Phe Asn Pro Glu
        115                 120                 125

Asp Tyr Tyr Asp Ile Leu Phe Pro Gly Val Asn Ala Phe Val Asn Asn
    130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ala Leu
                165                 170                 175

Thr Ser Gln Glu Ile Gln Arg Arg Thr Gln Lys Leu Phe Val Glu Ser
            180                 185                 190

Leu Ala Arg Phe Leu Glu Glu Thr Thr Trp Ala Ile Val Asn Ser Pro
        195                 200                 205

Ala Asn Leu Tyr Asn Tyr Ile Ser Asp Tyr Tyr Ser Arg Leu Ser Pro
    210                 215                 220

Val Arg Pro Ser Met Val Arg Gln Val Ala Gln Arg Glu Gly Thr Tyr
225                 230                 235                 240

Ile Ser Phe Gly His Ser Tyr Thr Gln Ser Ile Asp Asp Ala Asp Ser
                245                 250                 255

Ile Gln Glu Val Thr Gln Arg Leu Asp Leu Lys Thr Pro Asn Val Gln
            260                 265                 270

Ser Gly Glu Phe Ile Glu Arg Ser Ile Ala Pro Gly Gly Ala Asn Gln
        275                 280                 285
```

-continued

```
Arg Ser Ala Pro Gln Trp Met Leu Pro Leu Leu Leu Gly Leu Tyr Gly
    290                 295                 300

Thr Val Thr Pro Ala Leu Glu Ala Tyr Glu Asp Gly Pro Asn Lys Lys
305                 310                 315                 320

Lys Arg Arg Lys Glu Gly Pro Arg Ala Ser Ser Lys Thr Ser Tyr Lys
                325                 330                 335

Arg Arg Ser Arg Ser Ser Arg Ser
            340


<210> SEQ ID NO 19
<211> LENGTH: 225
<212> TYPE: PRT
<213> ORGANISM: JC virus

<400> SEQUENCE: 19

Met Ala Leu Gln Leu Phe Asn Pro Glu Asp Tyr Tyr Asp Ile Leu Phe
1               5                   10                  15

Pro Gly Val Asn Ala Phe Val Asn Asn Ile His Tyr Leu Asp Pro Arg
            20                  25                  30

His Trp Gly Pro Ser Leu Phe Ser Thr Ile Ser Gln Ala Phe Trp Asn
        35                  40                  45

Leu Val Arg Asp Asp Leu Pro Ala Leu Thr Ser Gln Glu Ile Gln Arg
    50                  55                  60

Arg Thr Gln Lys Leu Phe Val Glu Ser Leu Ala Arg Phe Leu Glu Glu
65                  70                  75                  80

Thr Thr Trp Ala Ile Val Asn Ser Pro Ala Asn Leu Tyr Asn Tyr Ile
                85                  90                  95

Ser Asp Tyr Tyr Ser Arg Leu Ser Pro Val Arg Pro Ser Met Val Arg
            100                 105                 110

Gln Val Ala Gln Arg Glu Gly Thr Tyr Ile Ser Phe Gly His Ser Tyr
        115                 120                 125

Thr Gln Ser Ile Asp Asp Ala Asp Ser Ile Gln Glu Val Thr Gln Arg
    130                 135                 140

Leu Asp Leu Lys Thr Pro Asn Val Gln Ser Gly Glu Phe Ile Glu Arg
145                 150                 155                 160

Ser Ile Ala Pro Gly Gly Ala Asn Gln Arg Ser Ala Pro Gln Trp Met
                165                 170                 175

Leu Pro Leu Leu Leu Gly Leu Tyr Gly Thr Val Thr Pro Ala Leu Glu
            180                 185                 190

Ala Tyr Glu Asp Gly Pro Asn Lys Lys Lys Arg Arg Lys Glu Gly Pro
        195                 200                 205

Arg Ala Ser Ser Lys Thr Ser Tyr Lys Arg Arg Ser Arg Ser Ser Arg
    210                 215                 220

Ser
225


<210> SEQ ID NO 20
<211> LENGTH: 354
<212> TYPE: PRT
<213> ORGANISM: JC virus

<400> SEQUENCE: 20

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30
```

-continued

Gly Val Asp Ser Ile Thr Glu Val Glu Cys Phe Leu Thr Pro Glu Met
35 40 45

Gly Asp Pro Asp Glu His Leu Arg Gly Phe Ser Lys Ser Ile Ser Ile
50 55 60

Ser Asp Thr Phe Glu Ser Asp Ser Pro Asn Lys Asp Met Leu Pro Cys
65 70 75 80

Tyr Ser Val Ala Arg Ile Pro Leu Pro Asn Leu Asn Glu Asp Leu Thr
85 90 95

Cys Gly Asn Ile Leu Met Trp Glu Ala Val Thr Leu Lys Thr Glu Val
100 105 110

Ile Gly Val Thr Thr Leu Met Asn Val His Ser Asn Gly Gln Ala Thr
115 120 125

His Asp Asn Gly Ala Gly Lys Pro Val Gln Gly Thr Ser Phe His Phe
130 135 140

Phe Ser Val Gly Gly Glu Ala Leu Glu Leu Gln Gly Val Val Phe Asn
145 150 155 160

Tyr Arg Thr Lys Tyr Pro Asp Gly Thr Ile Phe Pro Lys Asn Ala Thr
165 170 175

Val Gln Ser Gln Val Met Asn Thr Glu His Lys Ala Tyr Leu Asp Lys
180 185 190

Asn Lys Ala Tyr Pro Val Glu Cys Trp Val Pro Asp Pro Thr Arg Asn
195 200 205

Glu Asn Thr Arg Tyr Phe Gly Thr Leu Thr Gly Gly Glu Asn Val Pro
210 215 220

Pro Val Leu His Ile Thr Asn Thr Ala Thr Thr Val Leu Leu Asp Glu
225 230 235 240

Phe Gly Val Gly Pro Leu Cys Lys Gly Asp Asn Leu Tyr Leu Ser Ala
245 250 255

Val Asp Val Cys Gly Met Phe Thr Asn Arg Ser Gly Ser Gln Gln Trp
260 265 270

Arg Gly Leu Ser Arg Tyr Phe Lys Val Gln Leu Arg Lys Arg Arg Val
275 280 285

Lys Asn Pro Tyr Pro Ile Ser Phe Leu Leu Thr Asp Leu Ile Asn Arg
290 295 300

Arg Thr Pro Arg Val Asp Gly Gln Pro Met Tyr Gly Met Asp Ala Gln
305 310 315 320

Val Glu Glu Val Arg Val Phe Glu Gly Thr Glu Glu Leu Pro Gly Asp
325 330 335

Pro Asp Met Met Arg Tyr Val Asp Arg Tyr Gly Gln Leu Gln Thr Lys
340 345 350

Met Leu

<210> SEQ ID NO 21
<211> LENGTH: 354
<212> TYPE: PRT
<213> ORGANISM: JC virus

<400> SEQUENCE: 21

Met Ala Pro Thr Lys Arg Lys Gly Glu Arg Lys Asp Pro Val Gln Val
1 5 10 15

Pro Lys Leu Leu Ile Arg Gly Gly Val Glu Val Leu Glu Val Lys Thr
20 25 30

Gly Val Asp Ser Ile Thr Glu Val Glu Cys Phe Leu Thr Pro Glu Met
35 40 45

Gly Asp Pro Asp Glu His Phe Arg Gly Phe Ser Lys Ser Ile Ser Ile
50 55 60

Ser Asp Thr Phe Glu Ser Asp Ser Pro Asn Lys Asp Met Leu Pro Cys
65 70 75 80

Tyr Ser Val Ala Arg Ile Pro Leu Pro Asn Leu Asn Glu Asp Leu Thr
85 90 95

Cys Gly Asn Ile Leu Met Trp Glu Ala Val Thr Leu Lys Thr Glu Val
100 105 110

Ile Gly Val Thr Thr Leu Met Asn Val His Ser Asn Gly Gln Ala Thr
115 120 125

His Asp Asn Gly Ala Ala Lys Pro Val Gln Gly Thr Ser Phe His Phe
130 135 140

Phe Ser Val Gly Gly Glu Ala Leu Glu Leu Gln Gly Val Val Phe Asn
145 150 155 160

Tyr Arg Thr Thr Tyr Pro Asp Gly Thr Ile Phe Pro Lys Asn Ala Thr
165 170 175

Val Gln Ser Gln Val Met Asn Thr Glu His Lys Ala Tyr Leu Asp Lys
180 185 190

Asn Lys Ala Tyr Pro Val Glu Cys Trp Val Pro Asp Pro Thr Arg Asn
195 200 205

Glu Asn Thr Arg Tyr Phe Gly Thr Leu Thr Gly Gly Glu Asn Val Pro
210 215 220

Pro Val Leu His Ile Thr Asn Thr Ala Thr Thr Val Leu Leu Asp Glu
225 230 235 240

Phe Gly Val Gly Pro Leu Cys Lys Gly Asp Asn Leu Tyr Leu Ser Ala
245 250 255

Val Asp Val Cys Gly Met Phe Thr Asn Arg Ser Gly Ser Gln Gln Trp
260 265 270

Arg Gly Leu Ser Arg Tyr Phe Lys Val Gln Leu Arg Lys Arg Arg Val
275 280 285

Lys Asn Pro Tyr Pro Ile Ser Phe Leu Leu Thr Asp Leu Ile Asn Arg
290 295 300

Arg Thr Pro Arg Val Asp Gly Gln Pro Met Tyr Gly Met Asp Ala Gln
305 310 315 320

Ile Glu Glu Val Arg Val Phe Glu Gly Thr Glu Gln Leu Pro Gly Asp
325 330 335

Pro Asp Met Met Arg Tyr Val Asp Arg Tyr Gly Gln Leu Gln Thr Lys
340 345 350

Met Leu

<210> SEQ ID NO 22
<211> LENGTH: 344
<212> TYPE: PRT
<213> ORGANISM: JC virus

<400> SEQUENCE: 22

Met Gly Ala Ala Leu Ala Leu Leu Gly Asp Leu Val Ala Thr Val Ser
1 5 10 15

Glu Ala Ala Ala Ala Thr Gly Phe Ser Val Ala Glu Ile Ala Ala Gly
20 25 30

Glu Ala Ala Ala Thr Ile Glu Val Glu Ile Ala Ser Leu Ala Thr Val
35 40 45

Glu Gly Ile Thr Ser Thr Ser Glu Ala Ile Ala Ala Ile Gly Leu Thr
50 55 60

-continued

```
Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

Gly Leu Phe Gln Gln Pro Ala Met Ala Leu Gln Leu Phe Asn Pro Glu
        115                 120                 125

Asp Tyr Tyr Asp Ile Leu Phe Pro Gly Val Asn Ala Phe Val Asn Asn
    130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ser Leu
                165                 170                 175

Thr Ser Gln Glu Ile Gln Arg Arg Thr Gln Lys Leu Phe Val Glu Ser
            180                 185                 190

Leu Ala Arg Phe Leu Glu Glu Thr Thr Trp Ala Ile Val Asn Ser Pro
        195                 200                 205

Val Asn Leu Tyr Asn Tyr Ile Ser Asp Tyr Tyr Ser Arg Leu Ser Pro
    210                 215                 220

Val Arg Pro Ser Met Val Arg Gln Val Ala Gln Arg Glu Gly Thr Tyr
225                 230                 235                 240

Ile Ser Phe Gly His Ser Tyr Thr Gln Ser Ile Asp Asp Ala Asp Ser
                245                 250                 255

Ile Gln Glu Val Thr Gln Arg Leu Asp Leu Lys Thr Pro Asn Val Gln
            260                 265                 270

Ser Gly Glu Phe Ile Glu Lys Ser Ile Ala Pro Gly Gly Ala Asn Gln
        275                 280                 285

Arg Ser Ala Pro Gln Trp Met Leu Pro Leu Leu Leu Gly Leu Tyr Gly
    290                 295                 300

Thr Val Thr Pro Ala Leu Glu Ala Tyr Glu Asp Gly Pro Asn Lys Lys
305                 310                 315                 320

Lys Arg Arg Lys Glu Gly Pro Arg Ala Ser Ser Lys Thr Ser Tyr Lys
                325                 330                 335

Arg Arg Ser Arg Ser Ser Arg Ser
            340


<210> SEQ ID NO 23
<211> LENGTH: 225
<212> TYPE: PRT
<213> ORGANISM: JC virus

<400> SEQUENCE: 23

Met Ala Leu Gln Leu Phe Asn Pro Glu Asp Tyr Tyr Asp Ile Leu Phe
1               5                   10                  15

Pro Gly Val Asn Ala Phe Val Asn Asn Ile His Tyr Leu Asp Pro Arg
            20                  25                  30

His Trp Gly Pro Ser Leu Phe Ser Thr Ile Ser Gln Ala Phe Trp Asn
        35                  40                  45

Leu Val Arg Asp Asp Leu Pro Ser Leu Thr Ser Gln Glu Ile Gln Arg
    50                  55                  60

Arg Thr Gln Lys Leu Phe Val Glu Ser Leu Ala Arg Phe Leu Glu Glu
65                  70                  75                  80

Thr Thr Trp Ala Ile Val Asn Ser Pro Val Asn Leu Tyr Asn Tyr Ile
                85                  90                  95
```

-continued

Ser Asp Tyr Tyr Ser Arg Leu Ser Pro Val Arg Pro Ser Met Val Arg
100 105 110

Gln Val Ala Gln Arg Glu Gly Thr Tyr Ile Ser Phe Gly His Ser Tyr
115 120 125

Thr Gln Ser Ile Asp Asp Ala Asp Ser Ile Gln Glu Val Thr Gln Arg
130 135 140

Leu Asp Leu Lys Thr Pro Asn Val Gln Ser Gly Glu Phe Ile Glu Lys
145 150 155 160

Ser Ile Ala Pro Gly Gly Ala Asn Gln Arg Ser Ala Pro Gln Trp Met
165 170 175

Leu Pro Leu Leu Leu Gly Leu Tyr Gly Thr Val Thr Pro Ala Leu Glu
180 185 190

Ala Tyr Glu Asp Gly Pro Asn Lys Lys Lys Arg Arg Lys Glu Gly Pro
195 200 205

Arg Ala Ser Ser Lys Thr Ser Tyr Lys Arg Arg Ser Arg Ser Ser Arg
210 215 220

Ser
225

<210> SEQ ID NO 24
<211> LENGTH: 1089
<212> TYPE: DNA
<213> ORGANISM: BK virus

<400> SEQUENCE: 24
atggccccaa ccaaaagaaa aggagagtgt ccaggggcag ctcccaaaaa gccaaaggaa 60
cccgtgcaag tgccaaaact actaataaaa ggaggagtag aagttctaga agttaaaact 120
ggggtagatg ctataacaga ggtagaatgc ttcctaaacc cagaaatggg ggatccagat 180
gaaaacctta ggggctttag tctaaagcta agtgctgaaa atgactttag cagtgatagc 240
ccagaaagaa aaatgcttcc ctgttacagc acagcaagaa ttcccctccc caatttaaat 300
gaggacctaa cctgtggaaa tctactgatg tgggaggctg taactgtaca aacagaggtc 360
attggaataa ctagcatgct taaccttcat gcagggtcac aaaaagtgca tgagcatggt 420
ggaggtaaac ctattcaagg cagtaatttc cacttctttg ctgttggtgg agaccccttg 480
gaaatgcagg gagtgctaat gaattacagg accaagtacc cagatggtac tataacccca 540
aaaaacccaa cagcccagtc ccaggtaatg aatactgacc ataaggccta tttggacaaa 600
aacaatgctt atccagttga gtgctgggtt cctgatccta gtagaaatga aaatactagg 660
tattttggga ctttcacagg aggggaaaat gttcccccag tacttcatgt gaccaacaca 720
gctaccacag tgttgctaga tgaacagggt gtggggcctc tttgtaaagc tgatagcctg 780
tatgtttcag ctgctgatat ttgtggcctg tttactaaca gctctggaac acaacagtgg 840
agaggccttg caagatattt taagattcgc ctgagaaaaa gatctgtaaa aaatccttac 900
ccaatttcct ttttgctaag tgaccttata aacaggagaa cccagagagt ggatgggcag 960
cctatgtatg gtatggaatc ccaggtagaa gaggttaggg tgtttgatgg cacagaaaga 1020
cttccagggg acccagatat gataagatat attgataaac aaggacaatt gcaaaccaaa 1080
atgctttaa 1089

<210> SEQ ID NO 25
<211> LENGTH: 1056
<212> TYPE: DNA
<213> ORGANISM: BK virus

<400> SEQUENCE: 25
atgggtgctg ctctagcact tttgggggac ctagttgcca gtgtatctga ggctgctgct 60
gccacaggat tttcagtggc tgaaattgct gctggggagg ctgctgctgc tatagaagtt 120
caaattgcat cccttgctac tgtagagggc ataacaagta cctcagaggc tatagctgct 180
ataggcctaa ctcctcaaac atatgctgta attgctggtg ctcctggggc tattgctggg 240
tttgctgctt taattcaaac tgttactggt attagttcct tggctcaagt agggtatagg 300
ttttttagtg attgggatca caaagtttcc actgtaggcc tctatcagca atcaggcatg 360
gctttggaat tgtttaaccc agatgagtac tatgatattt tgtttcctgg tgtaaatact 420
tttgtaaata atattcaata ccttgatcct aggcattggg gtccttcctt gtttgctact 480
atttcccagg ctttgtggca tgttattagg gatgatatac ctgctataac ctcacaagaa 540
ttgcaaagaa gaacagaaag attttttaga gactccttgg ctagattttt ggaggaaact 600
acctggacaa ttgtaaatgc ccctataaac ttttataatt atattcaaga atattattct 660
gatctttccc ctattaggcc ctcaatggtt agacaagtgg ctgaaaggga aggtacccgt 720
gtacattttg gccatactta tagtatagat gatgctgaca gtatagaaga agttacacaa 780
agaatggact taagaaatca acaaactgta cattcaggag agtttataga aaaaactatt 840
gccccaggag gtgctaatca aagaactgct cctcaatgga tgttgccttt acttctaggc 900
ctgtacggga ctgtaacacc tgctcttgaa gcatatgaag atggccccaa ccaaaagaaa 960
aggagagtgt ccaggggcag ctcccaaaaa gccaaaggaa cccgtgcaag tgccaaaact 1020
actaataaaa ggaggagtag aagttctaga agttaa 1056

<210> SEQ ID NO 26
<211> LENGTH: 699
<212> TYPE: DNA
<213> ORGANISM: BK virus

<400> SEQUENCE: 26
atggctttgg aattgtttaa cccagatgag tactatgata ttttgtttcc tggtgtaaat 60
acttttgtaa ataatattca ataccttgat cctaggcatt ggggtccttc cttgtttgct 120
actatttccc aggctttgtg gcatgttatt agggatgata tacctgctat aacctcacaa 180
gaattgcaaa gaagaacaga aagatttttt agagactcct tggctagatt tttggaggaa 240
actacctgga caattgtaaa tgcccctata aacttttata attatattca agaatattat 300
tctgatcttt cccctattag gccctcaatg gttagacaag tggctgaaag ggaaggtacc 360
cgtgtacatt ttggccatac ttatagtata gatgatgctg acagtataga agaagttaca 420
caaagaatgg acttaagaaa tcaacaaact gtacattcag gagagtttat agaaaaaact 480
attgccccag gaggtgctaa tcaaagaact gctcctcaat ggatgttgcc tttacttcta 540
ggcctgtacg ggactgtaac acctgctctt gaagcatatg aagatggccc caaccaaaag 600
aaaaggagag tgtccagggg cagctcccaa aaagccaaag gaacccgtgc aagtgccaaa 660
actactaata aaaggaggag tagaagttct agaagttaa 699

<210> SEQ ID NO 27
<211> LENGTH: 1089
<212> TYPE: DNA
<213> ORGANISM: BK virus

<400> SEQUENCE: 27

```
atggccccaa ccaaaagaaa aggagagtgt ccaggggcag ctcccaaaaa gccaaaggaa     60

cccgtgcaag tgccaaaact actaataaaa ggaggagtag aagttctaga agttaaaact    120

ggggtagatg ctataacaga agtagaatgc tttctaaatc cagaaatggg ggatccagat    180

aatgacctta ggggctatag tctaagacta actgctgaaa ctgcctttga cagtgatagc    240

ccagacagaa aaatgcttcc ctgttacagc acagcaagaa ttccactacc taatttgaat    300

gaggatctaa cctgtggaaa tctactaatg tgggaggctg tgactgtaaa aacagaggtt    360

attggaataa ctagtatgct taaccttcat gcagggtcac agaaagtaca tgaaaatggt    420

ggaggcaaac ctattcaagg cagcaatttt cactttttg ctgtgggtgg ggaccccttg    480

gaaatgcagg gagtacttat gaactacaga acaaagtacc cagaaggtac tgtcacccca    540

aaaaatccca cagctcagtc ccaggtaatg aatactgacc ataaggccta cttggacaaa    600

aacaatgctt atccagttga atgctggatt cctgacccta gtaaaaatga aaatactaga    660

tattttggaa catacacagg aggggaaaat gttcccccag tacttcatgt aaccaacaca    720

gctaccacag tgttgctgga tgaacagggt gtggggcctc tgtgtaaagc tgatagcctg    780

tatgtttcag ctgctgatat ttgtggactg tttactaaca gctctggaac acaacagtgg    840

aggggccttc caagatattt taagattcgc ctgagaaaaa gatctgtaaa gaacccttac    900

ccaatttcct ttttgcttag tgaccttata aacaggagaa cccagagagt ggatgggcag    960

cctatgtatg gtatggagtc tcaggtggag gaggtcaggg tgtttgatgg cacagaacag   1020

cttccagggg acccagatat gataagatat attgacagac agggacaatt gcaaacaaaa   1080

atggtttaa                                                           1089
```

<210> SEQ ID NO 28
<211> LENGTH: 1056
<212> TYPE: DNA
<213> ORGANISM: BK virus

<400> SEQUENCE: 28

```
atgggtgctg ctctagcact tttgggggac ctagttgcca gtgtatctga ggctgctgct     60

gccacaggat tttcagtggc tgaaattgct gctggggagg ctgctgctgc tatagaagtt    120

caaattgcat cccttgctac tgtagagggc ataacaagta cctcagaggc tatagctgct    180

ataggcctaa ctcctcaaac atatgctgta attgctggtg ctccaggggc tattgctggg    240

tttgctgctt taattcaaac tgttactggt attagttctt tggctcaagt agggtatagg    300

ttttttagtg attgggatca caaagtttcc actgtaggcc tttatcagca atcaggcatg    360

gcattggaat tgtttaaccc agatgagtac tatgatattt tgtttcctgg tgtaaatact    420

tttgtaaata atattcaata cctagatcct aggcattggg gtccttcttt gtttgctact    480

atttcccagg ctttgtggca tgttattagg gatgatatac ctgctataac ttcacaagaa    540

ttgcaaagaa gaacagagag attctttaga gactccttgg ctagattttt ggaagaaact    600

acctggacaa ttgtaaatgc ccctgtaaac ttttataatt atattcagga ttattattct    660

aatttgtccc ctattaggcc ttcaatggtt aggcaagttg ctgaaaggga aggaacccag    720

gtaaattttg gccataccta cagaatagat gatgctgaca gtatacaaga agttacccaa    780

agaatggagt taagaaataa agagaatgta cattcaggag agtttataga aaaaactatt    840

gccccaggag gtgctaatca aagaactgct cctcaatgga tgttgccttt gcttctaggc    900

ctgtacggga ctgtaacacc tgctcttgaa gcatatgaag atggccccaa ccaaaagaaa    960

aggagagtgt ccaggggcag ctcccaaaaa gccaaaggaa cccgtgcaag tgccaaaact   1020
```

actaataaaa ggaggagtag aagttctaga agttaa 1056

<210> SEQ ID NO 29
<211> LENGTH: 699
<212> TYPE: DNA
<213> ORGANISM: BK virus

<400> SEQUENCE: 29
atggcattgg aattgtttaa cccagatgag tactatgata ttttgtttcc tggtgtaaat 60
acttttgtaa ataatattca atacctagat cctaggcatt ggggtccttc tttgtttgct 120
actatttccc aggctttgtg gcatgttatt agggatgata tacctgctat aacttcacaa 180
gaattgcaaa gaagaacaga gagattcttt agagactcct tggctagatt tttggaagaa 240
actacctgga caattgtaaa tgcccctgta aacttttata attatattca ggattattat 300
tctaatttgt cccctattag gccttcaatg gttaggcaag ttgctgaaag ggaaggaacc 360
caggtaaatt ttggccatac ctacagaata gatgatgctg acagtataca agaagttacc 420
caaagaatgg agttaagaaa taaagagaat gtacattcag gagagtttat agaaaaaact 480
attgccccag gaggtgctaa tcaaagaact gctcctcaat ggatgttgcc tttgcttcta 540
ggcctgtacg ggactgtaac acctgctctt gaagcatatg aagatggccc caaccaaaag 600
aaaaggagag tgtccagggg cagctcccaa aaagccaaag gaacccgtgc aagtgccaaa 660
actactaata aaaggaggag tagaagttct agaagttaa 699

<210> SEQ ID NO 30
<211> LENGTH: 1089
<212> TYPE: DNA
<213> ORGANISM: BK virus

<400> SEQUENCE: 30
atggccccaa ccaaaagaaa aggagagtgt ccaggggcag ctcccaaaaa gccaaaggaa 60
cccgtgcaag tgccaaaact actaataaaa ggaggagtag aagttctaga agttaaaact 120
ggggtagatg ctataacaga ggtagaatgc tttctaaatc cagaaatggg ggatccagat 180
aatgacctta ggggctatag tctaaagcta actgctgaaa atgcctttga cagtgatagc 240
ccagacaaaa aaatgcttcc ttgttacagc acagcaagaa ttccactgcc caatctaaat 300
gaggacctaa cctgtggaaa tctactaatg tgggaggctg taactgtaaa aacagaggtt 360
attggaataa ctagcatgct taaccttcat gcagggtccc aaaaagttca tgagaatggt 420
ggaggcaaac ctgtgcaagg cagtaatttc cacttctttg ctgtgggtgg agaccccttg 480
gaaatgcagg gagtgctaat gaattacaga acaaagtacc cacaaggtac tataacccct 540
aaaaacccta cagctcagtc ccaggtaatg aatactgatc ataaggccta tttggacaaa 600
aacaatgctt atccagttga gtgctggatt cctgatccta gtagaaatga aaatactagg 660
tattttggaa cttacacagg aggggaaaat gttcccccag tacttcatgt taccaacaca 720
gctaccacag tgttgctgga tgaacagggt gtggggcctc tatgtaaagc tgacagcctg 780
tatgtttcag ctgctgatat ttgtgggctg tttactaaca gctctgggac acaacagtgg 840
agaggccttg caagatattt taagattcgc ctgagaaaaa gatctgtgaa gaatccttac 900
ccaatttcct ttttgctaag tgaccttata aacaggagaa cccaaaaagt ggatgggcag 960
cctatgtatg gtatggaatc tcaggttgag gaggtgaggg tgtttgatgg cacagaacag 1020
cttccagggg acccagatat gataagatat attgacagac aaggacaatt gcaaacaaaa 1080

-continued atggtttaa 1089

<210> SEQ ID NO 31
<211> LENGTH: 1056
<212> TYPE: DNA
<213> ORGANISM: BK virus

<400> SEQUENCE: 31

```
atgggtgctg ctctagcact tttgggggac ctagttgcca gtgtatctga ggctgctgct     60
gccacaggat tttcagtggc tgaaattgct gctggggagg ctgctgctgc catagaagtt    120
caaattgcat cccttgctac tgtagagggc ataacaacta cctcagaggc tatagctgct    180
ataggcctaa cacctcaaac atatgctgta attgctggtg ctccaggggc tattgctggg    240
tttgctgctt taattcaaac tgttactggt attagttctt tggctcaagt agggtatagg    300
ttttttagtg attgggatca caaagtttcc actgtaggcc tttatcagca atcaggcatg    360
gctttggaat tgtttaaccc agatgagtac tatgatattt tgtttcctgg tgtaaatact    420
tttgtaaata atattcaata tctagatcct aggcattggg gtccttcttt gtttgctact    480
atttctcagg ctttgtggca tgttattaga gatgatatac ctgctataac ttcacaagaa    540
ttgcaaagga gaacagaaag atttttttagg gactctttgg ctagattttt ggaagaaacc    600
acctggacaa ttgtaaatgc ccctgtaaac ttttataatt atattcagga ttattattct    660
aatttgtccc ctattaggcc ttcaatggtt aggcaagtag ctgaaaggga aggtacccat    720
gtaaattttg gccataccta cagcatagat gatgctgaca gtatagaaga agttacccaa    780
agaatagagt taagaaataa ggaaagtgta cattcaggag agtttataga aaaaactatt    840
gccccaggag gtgctaatca aagaactgct cctcaatgga tgttgccttt gcttctaggc    900
ctgtacggga ctgtaacacc tgctcttgaa gcatatgaag atggccccaa ccaaaagaaa    960
aggagagtgt ccaggggcag ctcccaaaaa gccaaaggaa cccgtgcaag tgccaaaact   1020
actaataaaa ggaggagtag aagttctaga agttaa                             1056
```

<210> SEQ ID NO 32
<211> LENGTH: 699
<212> TYPE: DNA
<213> ORGANISM: BK virus

<400> SEQUENCE: 32

```
atggctttgg aattgtttaa cccagatgag tactatgata ttttgtttcc tggtgtaaat     60
acttttgtaa ataatattca atatctagat cctaggcatt ggggtccttc tttgtttgct    120
actatttctc aggctttgtg gcatgttatt agagatgata tacctgctat aacttcacaa    180
gaattgcaaa ggagaacaga aagatttttt agggactctt tggctagatt tttggaagaa    240
accacctgga caattgtaaa tgcccctgta aacttttata attatattca ggattattat    300
tctaatttgt cccctattag gccttcaatg gttaggcaag tagctgaaag ggaaggtacc    360
catgtaaatt ttggccatac ctacagcata gatgatgctg acagtataga agaagttacc    420
caaagaatag agttaagaaa taaggaaagt gtacattcag gagagtttat agaaaaaact    480
attgccccag gaggtgctaa tcaaagaact gctcctcaat ggatgttgcc tttgcttcta    540
ggcctgtacg ggactgtaac acctgctctt gaagcatatg aagatggccc caaccaaaag    600
aaaaggagag tgtccagggg cagctcccaa aaagccaaag gaacccgtgc aagtgccaaa    660
actactaata aaaggaggag tagaagttct agaagttaa                           699
```

<210> SEQ ID NO 33
<211> LENGTH: 1089
<212> TYPE: DNA
<213> ORGANISM: BK virus

<400> SEQUENCE: 33
atggccccaa ccaaaagaaa aggagagtgt ccaggggcag ctcccaaaaa gccaaaggaa 60
cccgtgcaag tgccaaaact actaataaaa ggaggagtag aagttctaga agttaaaact 120
ggggtagatg ctataacaga ggtagaatgc tttctaaacc cagaaatggg ggatccagat 180
gatcacctta ggggctatag tcagcaccta actgctgaaa atgcctttga cagtgatagc 240
ccagacaaaa aaatgcttcc ttgttacagt acagcaagaa ttccactgcc caacctaaat 300
gaggacctaa cctgtggaaa tctactaatg tgggaggctg taactgtaaa aacagaggtt 360
attggaataa ctagcatgct taaccttcat gcagggtccc aaaaagttca tgagaatggt 420
ggaggtaaac ctgtccaagg cagtaatttc cacttctttg ctgtgggtgg agaccccttg 480
gaaatgcagg gagtgctaat gaattacaga acaaagtacc cacaaggtac tataacccct 540
aaaaacccta cagctcagtc ccaggtaatg aatactgatc ataaggccta tttggacaaa 600
aacaatgctt atccagttga gtgctggatt cctgatccta gtaaaaatga aaatactagg 660
tattttggaa cttacacagg aggggaaaat gttcctccag tacttcatgt taccaacaca 720
gctaccacag tgttgctgga tgaacagggt gtggggcctc tgtgtaaagc tgatagcctg 780
tatgtttcag ctgctgatat ttgtgggctg tttactaaca gctctgggac acaacagtgg 840
agaggccttg caagatattt taagattcgc ctgagaaaaa gatctgtgaa gaatccttac 900
ccaatttcct ttttgctaag tgaccttata aacaggagaa cccaaaaagt ggatgggcag 960
cctatgtatg gtatggaatc tcaggttgag gaggtaaggg tgtttgatgg cacagaacag 1020
cttccagggg acccagatat gataagatat attgacagac aaggacaatt gcaaacaaaa 1080
atggtttaa 1089

<210> SEQ ID NO 34
<211> LENGTH: 1056
<212> TYPE: DNA
<213> ORGANISM: BK virus

<400> SEQUENCE: 34
atgggtgctg ctctagcact tttgggggac ctagttgcca gtgtatctga ggctgctgct 60
gccacaggat tttcagtggc tgaaattgct gctggggagg ctgctgctgc catagaagtt 120
caaattgcat cccttgctac tgtagagggc ataacaacta cctcagaggc tatagctgct 180
ataggcctaa cacctcaaac atatgctgta attgctggtg ctccaggggc tattgctggg 240
tttgctgctt taattcaaac tgttactggt attagttctt tggctcaagt agggtatagg 300
ttttttagtg attgggatca caaagtttcc actgtaggcc tttatcagca atcaggcatg 360
gctttggaat tgtttaaccc agatgagtac tatgatattt tgtttcctgg tgtaaatacc 420
tttgttaata atattcaata tctagatcct aggcattggg gtccttcttt gtttgctact 480
atttcccagg ctttgtggca tgttattaga gatgatatac ctgctataac ttcacaagaa 540
ttgcaaagga gaacagagag attttttagg gactctttgg ctagattttt ggaagaaacc 600
acctggacaa ttgtaaatgc cccataaac ttttataatt atattcagga ttattattct 660
aatttgtccc ctattaggcc ttcaatggtt aggcaagtag ctgaaaggga aggtacccat 720
gtaaattttg gccataccta cagcatagat aatgctgaca gtatagaaga agttacccaa 780

-continued agaatggatt taagaaataa ggaaagtgta cattcaggag agtttataga aaaaactatt 840
gccccaggag gtgctaatca aagaactgct cctcaatgga tgttgccttt gcttctaggc 900
ctgtacggga ctgtaacacc tgctcttgaa gcatatgaag atggccccaa ccaaaagaaa 960
aggagagtgt ccaggggcag ctcccaaaaa gccaaaggaa cccgtgcaag tgccaaaact 1020
actaataaaa ggaggagtag aagttctaga agttaa 1056

<210> SEQ ID NO 35
<211> LENGTH: 699
<212> TYPE: DNA
<213> ORGANISM: BK virus

<400> SEQUENCE: 35
atggctttgg aattgtttaa cccagatgag tactatgata ttttgtttcc tggtgtaaat 60
acctttgtta ataatattca atatctagat cctaggcatt ggggtccttc tttgtttgct 120
actatttccc aggctttgtg gcatgttatt agagatgata tacctgctat aacttcacaa 180
gaattgcaaa ggagaacaga gagatttttt agggactctt tggctagatt tttggaagaa 240
accacctgga caattgtaaa tgcccccata aacttttata attatattca ggattattat 300
tctaatttgt cccctattag gccttcaatg gttaggcaag tagctgaaag ggaaggtacc 360
catgtaaatt ttggccatac ctacagcata gataatgctg acagtataga agaagttacc 420
caaagaatgg atttaagaaa taaggaaagt gtacattcag gagagtttat agaaaaaact 480
attgccccag gaggtgctaa tcaaagaact gctcctcaat ggatgttgcc tttgcttcta 540
ggcctgtacg ggactgtaac acctgctctt gaagcatatg aagatggccc caaccaaaag 600
aaaaggagag tgtccagggg cagctcccaa aaagccaaag gaacccgtgc aagtgccaaa 660
actactaata aaaggaggag tagaagttct agaagttaa 699

<210> SEQ ID NO 36
<211> LENGTH: 1065
<212> TYPE: DNA
<213> ORGANISM: JC virus

<400> SEQUENCE: 36
atggccccaa caaaaagaaa aggagaaagg aaggaccccg tgcaagttcc aaaacttctt 60
ataagaggag gagtagaagt tctagaagtt aaaactgggg ttgactcaat tacagaggta 120
gaatgctttt taactccaga aatgggtgac ccagatgagc atcttagggg ttttagtaag 180
tcaatatcta tatcagatac atttgaaagt gactccccaa atagggacat gcttccttgt 240
tacagtgtgg ccagaattcc actacccaat ctaaatgagg atctaacctg tggaaatata 300
ctcatgtggg aggctgtgac cttaaaaact gaggttatag gggtgacaag tttgatgaat 360
gtgcactcta atgggcaagc aactcatgac aatggtgcag ggaagccagt gcagggcacc 420
agctttcatt ttttttctgt tgggggggag gctttagaat tacagggggt gctttttaat 480
tacagaacaa agtacccaga tggaacaatt tttccaaaga atgccacagt gcaatctcaa 540
gtcatgaaca cagagcacaa ggcgtaccta gataagaaca aagcatatcc tgttgaatgt 600
tgggttcctg atcccaccag aaatgaaaac acaagatatt ttgggacact aacaggagga 660
gaaaatgttc ctccagttct tcatataaca aacactgcca caacagtgtt gcttgatgaa 720
tttggtgttg ggccactttg caaaggtgac aacttatact tgtcagctgt tgatgtctgt 780
ggcatgttta caaacaggtc tggttcccag cagtggagag gactctccag atattttaag 840
gtgcagctaa ggaaaaggag ggttaaaaac ccctacccaa tttctttcct tcttactgat 900

```
ttaattaaca gaaggactcc tagagttgat gggcagccta tgtatggcat ggatgctcaa    960

gtagaggagg ttagagtttt tgagggaaca gaggagcttc caggggaccc agacatgatg   1020

agatacgttg acaaatatgg acagttgcag acaaaaatgc tgtaa                  1065


<210> SEQ ID NO 37
<211> LENGTH: 1035
<212> TYPE: DNA
<213> ORGANISM: JC virus

<400> SEQUENCE: 37

atgggtgccg cacttgcact tttgggggac ctagttgcta ctgtttctga ggctgctgct     60

gccacaggat tttcagtagc tgaaattgct gctggagagg ctgctgctac tatagaagtt    120

gaaattgcat cccttgctac tgtagagggg attacaagta cctctgaggc tatagctgct    180

ataggcctta ctcctgaaac atatgctgta ataactggag ctccgggggc tgtagctggg    240

tttgctgcat tggttcaaac tgtaactggt ggtagtgcta ttgctcagtt gggatataga    300

tttttgctg actgggatca taaagtttca acagttgggc tttttcagca gccagctatg    360

gctttacaat tatttaatcc agaagactac tatgatattt tatttcctgg agtgaatgcc    420

tttgttaaca atattcacta tttagatcct agacattggg gcccgtcctt gttctccaca    480

atctcccagg ctttttggaa tcttgttaga gatgatttgc cagccttaac ctctcaggaa    540

attcagagaa gaacccaaaa actatttgtt gaaagtttag caaggttttt ggaagaaact    600

acttgggcaa tagttaattc accagctaac ttatataatt atatttcaga ctattattct    660

agattgtctc cagttaggcc ctctatggta aggcaagttg cccaaaggga gggaacctat    720

atttcttttg gccactcata cacccaaagt atagatgatg cagacagcat tcaagaagtt    780

acccaaaggc tagatttaaa aaccccaaat gtgcaatctg gtgaatttat agaaagaagt    840

attgcaccag gaggtgcaaa tcaaagatct gctcctcaat ggatgttgcc tttactttta    900

gggttgtacg ggactgtaac acctgctctt gaagcatatg aagatggccc caacaaaaag    960

aaaaggagaa aggaaggacc ccgtgcaagt tccaaaactt cttataagag gaggagtaga   1020

agttctagaa gttaa                                                   1035


<210> SEQ ID NO 38
<211> LENGTH: 678
<212> TYPE: DNA
<213> ORGANISM: JC virus

<400> SEQUENCE: 38

atggctttac aattatttaa tccagaagac tactatgata ttttatttcc tggagtgaat     60

gcctttgtta acaatattca ctatttagat cctagacatt ggggcccgtc cttgttctcc    120

acaatctccc aggctttttg gaatcttgtt agagatgatt tgccagcctt aacctctcag    180

gaaattcaga gaagaaccca aaaactattt gttgaaagtt tagcaaggtt tttggaagaa    240

actacttggg caatagttaa ttcaccagct aacttatata attatatttc agactattat    300

tctagattgt ctccagttag gccctctatg gtaaggcaag ttgcccaaag ggagggaacc    360

tatatttctt ttggccactc atacacccaa agtatagatg atgcagacag cattcaagaa    420

gttacccaaa ggctagattt aaaaacccca aatgtgcaat ctggtgaatt tatagaaaga    480

agtattgcac caggaggtgc aaatcaaaga tctgctcctc aatggatgtt gcctttactt    540

ttagggttgt acgggactgt aacacctgct cttgaagcat atgaagatgg ccccaacaaa    600
```

-continued aagaaaagga gaaaggaagg accccgtgca agttccaaaa cttcttataa gaggaggagt 660
agaagttcta gaagttaa 678

<210> SEQ ID NO 39
<211> LENGTH: 1089
<212> TYPE: DNA
<213> ORGANISM: Artificial Sequence
<220> FEATURE:
<223> OTHER INFORMATION: Codon-optimized BKV-IVc2 VP1

<400> SEQUENCE: 39
atggcaccca caaagcgcaa gggcgaatgc cccggcgccg ccccaaagaa acccaaggag 60
ccagtccagg tccccaagtt gctgatcaag ggcggcgtgg aggtcctgga ggtcaagacc 120
ggcgtggacg ccatcaccga ggtggagtgt ttcttgaacc ccgagatggg cgaccccgac 180
aacgatctgc gcgggtacag cttgcgcctg accgccgaga ccgcattcga ttccgactca 240
cccgatcgca agatgttgcc atgctattcc accgcccgca tcccactgcc caacctcaac 300
gaagacttga catgcggcaa cctgctgatg tgggaagccg tcaccgtgaa gaccgaagtc 360
atcggcatca cctccatgtt gaatctgcac gccggaagcc aaaaggtgca cgagaacggc 420
ggcgggaagc ccatccaggg gtcaaacttc catttcttcg ccgtcggcgg cgatccactc 480
gagatgcaag gcgtgttgat gaactatcgc accaagtatc ccgagggcac cgtgacaccc 540
aagaacccaa ccgcccaaag tcaggtcatg aacaccgatc acaaagcata tctcgataag 600
aataacgcct accccgtcga gtgttggatc cccgatccat ccaagaacga gaacacccgc 660
tacttcggca cctataccgg cggcgagaac gtcccacccg tgttgcacgt gacaaatacc 720
gccacaaccg tcctgctcga cgagcaaggc gtcggcccac tctgcaaggc agacagcctc 780
tacgtcagcg ccgccgacat ctgcggactg ttcaccaatt caagcggcac ccagcaatgg 840
cgcgggttgc cccgctactt caaaatcagg ctccgcaagc gcagcgtgaa gaatccctat 900
ccaatcagtt tcctgctgtc cgatttgatc aatcgccgca cacaacgcgt cgacggccag 960
cccatgtacg gcatggaaag ccaagtcgaa gaagtgcgcg tcttcgacgg gaccgagcag 1020
ttgcccggcg atcccgacat gatccgctac atcgatcgcc aaggccagct ccaaaccaag 1080
atggtctga 1089

<210> SEQ ID NO 40
<211> LENGTH: 1056
<212> TYPE: DNA
<213> ORGANISM: Artificial Sequence
<220> FEATURE:
<223> OTHER INFORMATION: Codon-optimized BKV-IVc2 VP2

<400> SEQUENCE: 40
atgggcgcag ctctggcatt gctcggagat ctggtcgcat ctgtgtccga agcagccgct 60
gcaactggat tcagcgtcgc cgagatcgct gccggcgaag cagctgccgc aatcgaggtc 120
cagatcgcaa gtctggccac tgtggaaggg atcacctcta caagcgaagc catcgctgcc 180
atcggattga cccctcaaac ctacgccgtg atcgctggcg cacctggcgc aatcgctggt 240
ttcgccgcac tgatccagac tgtcaccgga atctcgagcc tcgcccaggt cggatatcgg 300
ttcttctcgg actgggacca taaggtcagt accgtggggt tgtaccaaca aagcgggatg 360
gccctcgagc tcttcaatcc cgacgaatac tacgacatcc tgttccctgg cgtgaacacc 420
ttcgtgaaca acatccagta tctggacccc cgccactggg gaccaagcct gttcgccaca 480
atcagtcaag ccctctggca cgtcatccgc gacgacatcc ccgccatcac aagccaggag 540

-continued ctccagcgcc gcaccgaaag gtttttccgc gatagtctcg caagattcct cgaggagacc 600
acatggacca tcgtgaacgc acccgtgaat ttctacaact acatccaaga ctactactcc 660
aacctgagtc ccatccgccc aagcatggtc cgccaagtcg ccgagcgcga gggcacacaa 720
gtgaacttcg ggcacacata tcgcatcgac gacgccgatt ccatccagga ggtcacacag 780
cgcatggaac tgcgcaacaa ggaaaacgtg cacagcggcg aattcatcga gaagaccatc 840
gcacccggcg gcgccaacca gcgcaccgcc ccacaatgga tgctcccact cttgctgggg 900
ctctatggca ccgtgacccc tgccctggag gcctacgagg acgggccaaa tcagaaaaag 960
cgccgcgtca gtcgcgggtc aagtcagaag gcaaagggca caagggcctc cgcaaagacc 1020
accaacaagc gccgctcccg gtcgagccgc tcatga 1056

<210> SEQ ID NO 41
<211> LENGTH: 699
<212> TYPE: DNA
<213> ORGANISM: Artificial Sequence
<220> FEATURE:
<223> OTHER INFORMATION: Codon-optimized BKV-IVc2 VP3

<400> SEQUENCE: 41
atggccctcg agctcttcaa tcccgacgaa tactacgaca tcctgttccc tggcgtgaac 60
accttcgtga acaacatcca gtatctggac ccccgccact ggggaccaag cctgttcgcc 120
acaatcagtc aagccctctg gcacgtcatc cgcgacgaca tccccgccat cacaagccag 180
gagctccagc gccgcaccga aaggtttttc cgcgatagtc tcgcaagatt cctcgaggag 240
accacatgga ccatcgtgaa cgcacccgtg aatttctaca actacatcca agactactac 300
tccaacctga gtcccatccg cccaagcatg gtccgccaag tcgccgagcg cgagggcaca 360
caagtgaact tcgggcacac atatcgcatc gacgacgccg attccatcca ggaggtcaca 420
cagcgcatgg aactgcgcaa caaggaaaac gtgcacagcg gcgaattcat cgagaagacc 480
atcgcacccg gcggcgccaa ccagcgcacc gccccacaat ggatgctccc actcttgctg 540
gggctctatg gcaccgtgac ccctgccctg gaggcctacg aggacgggcc aaatcagaaa 600
aagcgccgcg tcagtcgcgg gtcaagtcag aaggcaaagg gcacaagggc ctccgcaaag 660
accaccaaca agcgccgctc ccggtcgagc cgctcatga 699

<210> SEQ ID NO 42
<211> LENGTH: 1089
<212> TYPE: DNA
<213> ORGANISM: Artificial Sequence
<220> FEATURE:
<223> OTHER INFORMATION: Codon-optimized BKV-Ia VP1

<400> SEQUENCE: 42
atggcaccca caaagcgcaa gggcgaatgc cccggcgccg ccccaaagaa acccaaggag 60
ccagtccagg tccccaagtt gctgatcaag ggcggcgtgg aggtcctgga ggtcaagacc 120
ggcgtggacg ccatcaccga ggtggagtgt ttcttgaacc ccgagatggg cgaccccgac 180
gagaacctgc gcgggttcag cttgaagctg agcgccgaga acgacttcag ctccgactca 240
cccgaacgca agatgttgcc atgctattcc accgcccgca tcccactgcc caacctcaac 300
gaagacttga catgcggcaa cctgctgatg tgggaagccg tcaccgtgca gaccgaagtc 360
atcggcatca cctccatgtt gaatctgcac gccggaagcc aaaaggtgca cgagcacggc 420
ggcgggaagc ccatccaggg gtcaaacttc catttcttcg ccgtcggcgg cgatccactc 480

-continued

```
gagatgcaag gcgtgttgat gaactatcgc accaagtatc ccgacggcac catcacaccc    540

aagaacccaa ccgcccaaag tcaggtcatg aacaccgatc acaaagcata tctcgataag    600

aataacgcct accccgtcga gtgttgggtc cccgatccat cccggaacga gaacacccgc    660

tacttcggca cctttaccgg cggcgagaac gtcccacccg tgttgcacgt gacaaatacc    720

gccacaaccg tcctgctcga cgagcaaggc gtcggcccac tctgcaaggc agacagcctc    780

tacgtcagcg ccgccgacat ctgcggactg ttcaccaatt caagcggcac ccagcaatgg    840

cgcgggttgg cccgctactt caaaatcagg ctccgcaagc gcagcgtgaa gaatccctat    900

ccaatcagtt tcctgctgtc cgatttgatc aatcgccgca cacaacgcgt cgacggccag    960

cccatgtacg gcatggaaag ccaagtcgaa gaagtgcgcg tcttcgacgg gaccgagcgg   1020

ttgcccggcg atcccgacat gatccgctac atcgataagc aaggccagct ccaaaccaag   1080

atgctgtga                                                           1089
```

<210> SEQ ID NO 43
<211> LENGTH: 1089
<212> TYPE: DNA
<213> ORGANISM: Artificial Sequence
<220> FEATURE:
<223> OTHER INFORMATION: Codon-optimizied BKV-Ib2 VP1

<400> SEQUENCE: 43

```
atggcaccca caaagcgcaa gggcgaatgc cccggcgccg ccccaaagaa acccaaggag     60

ccagtccagg tccccaagtt gctgatcaag ggcggcgtgg aggtcctgga ggtcaagacc    120

ggcctggacg ccatcaccga ggtggagtgt ttcttgaacc ccgagatggg cgaccccgac    180

gagaacctgc gcgggttcag cttgaagctg agcgccaaga acgacttcag ctccgactca    240

cccgaccgca agatgttgcc atgctattcc accgcccgca tcccactgcc caacctcaac    300

gaagacttga catgcggcaa cctgctgatg tgggaagccg tcaccgtgca gaccgaagtc    360

atcggcatca cctccatgtt gaatctgcac gccggaagcc aaaaggtgca cgagcacggc    420

ggcgggaagc ccatccaggg gtcaaacttc catttcttcg ccgtcggcgg cgatccactc    480

gagatgcaag gcgtgttgat gaactatcgc accaagtatc ccgaaggcac catcacaccc    540

aagaacccaa ccgcccaaag tcaggtcatg aacaccgatc acaaagcata tctcgataag    600

aataacgcct accccgtcga gtgttggatc cccgatccat cccggaacga gaacacccgc    660

tacttcggca cctttaccgg cggcgagaac gtcccacccg tgttgcacgt gacaaatacc    720

gccacaaccg tcctgctcga cgagcaaggc gtcggcccac tctgcaaggc agacagcctc    780

tacgtcagcg ccgccgacat ctgcggactg ttcaccaatt caagcggcac ccagcaatgg    840

cgcgggttgg cccgctactt caaaatcagg ctccgcaagc gcagcgtgaa gaatccctat    900

ccaatcagtt tcctgctgtc cgatttgatc aatcgccgca cacaacgcgt cgacggccag    960

cccatgtacg gcatggaaag ccaagtcgaa gaagtgcgcg tcttcgacgg gaccgagcgg   1020

ttgcccggcg atcccgacat gatccgctac atcgataagc aaggccagct ccaaaccaag   1080

atgctgtga                                                           1089
```

<210> SEQ ID NO 44
<211> LENGTH: 1089
<212> TYPE: DNA
<213> ORGANISM: Artificial Sequence
<220> FEATURE:
<223> OTHER INFORMATION: Codon-optimized BKV-Ic VP1

<400> SEQUENCE: 44

```
atggcaccca caaagcgcaa gggcgaatgc cccggcgccg ccccaaagaa acccaaggag     60

ccagtccagg tccccaagtt gctgatcaag ggcggcgtgg aggtcctgga ggtcaagacc    120

ggcgtggacg ccatcaccga ggtggagtgt ttcttgaacc ccgagatggg cgaccccgac    180

gagaacctgc gcgggttcag cttgaagctg agcgtcgaga acgacttcag ctccgactca    240

ccccaacgca agatgttgcc atgctattcc accgcccgca tcccactgcc caacctcaac    300

gaagacttga catgcggcaa cctgctgatg tgggaagccg tcaccgtgca gaccgaagtc    360

atcggcatca cctccatgtt gaatctgcac gccggaagcc aaaaggtgca cgagcacggc    420

ggcgggaagc ccatccaggg gtcaaacttc catttcttcg ccgtcggcgg cgatccactc    480

gagatgcaag gcgtgttgat gaactatcgc accaagtatc ccgaaggcac catcacaccc    540

aagaacccaa ccgcccaaag tcaggtcatg aacaccgatc acaaagcata tctcgataag    600

aataacgcct accccgtcga gtgttggatc cccgatccat cccggaacga gaacacccgc    660

tacttcggca ccttgaccgg cggcgagaac gtcccacccg tgttgcacgt gacaaatacc    720

gccacaaccg tcctgctcga cgagcaaggc gtcggcccac tctgcaaggc agacagcctc    780

tacgtcagcg ccgccgacat ctgcggactg ttcaccaatt caagcggcac ccagcaatgg    840

cgcgggttgg cccgctactt caaaatcagg ctccgcaagc gcagcgtgaa gaatccctat    900

ccaatcagtt tcctgctgtc cgatttgatc aatcgccgca cacaacgcgt cgacggccag    960

cccatgtacg gcatggaaag ccaagtcgaa gaagtgcgcg tcttcgacgg gaccgagaag   1020

ttgcccggcg atcccgacat gatccgctac atcgataagc aaggccagct ccaaaccaag   1080

atgctgtga                                                           1089
```

```
<210> SEQ ID NO 45
<211> LENGTH: 1089
<212> TYPE: DNA
<213> ORGANISM: Artificial Sequence
<220> FEATURE:
<223> OTHER INFORMATION: Codon-optimized BKV-II VP1

<400> SEQUENCE: 45

atggcaccca caaagcgcaa gggcgaatgc cccggcgccg ccccaaagaa acccaaggag     60

ccagtccagg tccccaagtt gctgatcaag ggcggcgtgg aggtcctgga ggtcaagacc    120

ggcgtggacg ccatcaccga ggtggagtgt ttcttgaacc ccgagatggg cgaccccgac    180

aacgatctgc gcgggtacag cttgaagctg accgccgaga acgcattcga ttccgactca    240

cccgataaga agatgttgcc atgctattcc accgcccgca tcccactgcc caacctcaac    300

gaagacttga catgcggcaa cctgctgatg tgggaagccg tcaccgtgaa gaccgaagtc    360

atcggcatca cctccatgtt gaatctgcac gccggaagcc aaaaggtgca cgagaacggc    420

ggcgggaagc ccgtccaggg gtcaaacttc catttcttcg ccgtcggcgg cgatccactc    480

gagatgcaag gcgtgttgat gaactatcgc accaagtatc cccaaggcac catcacaccc    540

aagaacccaa ccgcccaaag tcaggtcatg aacaccgatc acaaagcata tctcgataag    600

aataacgcct accccgtcga gtgttggatc cccgatccat cccggaacga gaacacccgc    660

tacttcggca cctataccgg cggcgagaac gtcccacccg tgttgcacgt gacaaatacc    720

gccacaaccg tcctgctcga cgagcaaggc gtcggcccac tctgcaaggc agacagcctc    780

tacgtcagcg ccgccgacat ctgcggactg ttcaccaatt caagcggcac ccagcaatgg    840

cgcgggttgg cccgctactt caaaatcagg ctccgcaagc gcagcgtgaa gaatccctat    900
```

-continued ccaatcagtt tcctgctgtc cgatttgatc aatcgccgca cacaaaaggt cgacggccag 960
cccatgtacg gcatggaaag ccaagtcgaa gaagtgcgcg tcttcgacgg gaccgagcag 1020
ttgcccggcg atcccgacat gatccgctac atcgatcgcc aaggccagct ccaaaccaag 1080
atggtctga 1089

<210> SEQ ID NO 46
<211> LENGTH: 1089
<212> TYPE: DNA
<213> ORGANISM: Artificial Sequence
<220> FEATURE:
<223> OTHER INFORMATION: Codon-optimized BKV-III VP1

<400> SEQUENCE: 46
atggcaccca caaagcgcaa gggcgaatgc cccggcgccg ccccaaagaa acccaaggag 60
ccagtccagg tccccaagtt gctgatcaag ggcggcgtgg aggtcctgga ggtcaagacc 120
ggcgtggacg ccatcaccga ggtggagtgt ttcttgaacc ccgagatggg cgaccccgac 180
gaccatctgc gcgggtacag ccagcacctg accgccgaga acgcattcga ttccgactca 240
cccgataaga agatgttgcc atgctattcc accgcccgca tcccactgcc caacctcaac 300
gaagacttga catgcggcaa cctgctgatg tgggaagccg tcaccgtgaa gaccgaagtc 360
atcggcatca cctccatgtt gaatctgcac gccggaagcc aaaaggtgca cgagaacggc 420
ggcgggaagc ccgtccaggg gtcaaacttc catttcttcg ccgtcggcgg cgatccactc 480
gagatgcaag gcgtgttgat gaactatcgc accaagtatc cccaaggcac catcacaccc 540
aagaacccaa ccgcccaaag tcaggtcatg aacaccgatc acaaagcata tctcgataag 600
aataacgcct accccgtcga gtgttggatc cccgatccat ccaagaacga gaacacccgc 660
tacttcggca cctataccgg cggcgagaac gtcccacccg tgttgcacgt gacaaatacc 720
gccacaaccg tcctgctcga cgagcaaggc gtcggcccac tctgcaaggc agacagcctc 780
tacgtcagcg ccgccgacat ctgcggactg ttcaccaatt caagcggcac ccagcaatgg 840
cgcgggttgg cccgctactt caaaatcagg ctccgcaagc gcagcgtgaa gaatccctat 900
ccaatcagtt tcctgctgtc cgatttgatc aatcgccgca cacaaaaggt cgacggccag 960
cccatgtacg gcatggaaag ccaagtcgaa gaagtgcgcg tcttcgacgg gaccgagcag 1020
ttgcccggcg atcccgacat gatccgctac atcgatcgcc aaggccagct ccaaaccaag 1080
atggtctga 1089

<210> SEQ ID NO 47
<211> LENGTH: 1089
<212> TYPE: DNA
<213> ORGANISM: Artificial Sequence
<220> FEATURE:
<223> OTHER INFORMATION: Codon-optimized BKV-IVb1 VP1

<400> SEQUENCE: 47
atggcaccca caaagcgcaa gggcgaatgc cccggcgccg ccccaaagaa acccaaggag 60
ccagtccagg tccccaagtt gctgatcaag ggcggcgtgg aggtcctgga ggtcaagacc 120
ggcgtggacg ccatcaccga ggtggagtgt ttcttgaacc ccgagatggg cgaccccgac 180
aacgatctgc gcgggtacag cttgcgcctg accgccgaga ccgcattcaa ttccgactca 240
cccgatcgca agatgttgcc atgctattcc accgcccgca tcccactgcc caacctcaac 300
gaagacttga catgcggcaa cctgctgatg tgggaagccg tcaccgtgaa gaccgaagtc 360
atcggcatca cctccatgtt gaatctgcac gccggaagcc aaaaggtgca cgacaacggc 420
ggcgggaagc ccatccaggg gtcaaacttc catttcttcg ccgtcggcgg cgatccactc 480
gagatgcaag gcgtgttgat gaactatcgc accaagtatc ccgagggcac cgtgacaccc 540
aagaacccaa ccgcccaaag tcaggtcatg aacaccgatc acaaagcata tctcgataag 600
aataacgcct accccgtcga gtgttggatc cccgatccat cccgaaacga gaacacccgc 660
tacttcggca cctataccgg cggcgagaac gtcccacccg tgttgcacgt gacaaatacc 720
gccacaaccg tcctgctcga cgagcaaggc gtcggcccac tctgcaaggc agacagcctc 780
tacgtcagcg ccgccgacat ctgcggactg ttcaccaatt caagcggcac ccagcaatgg 840
cgcgggttgc cccgctactt caaaatcagg ctccgcaagc gcagcgtgaa gaatccctat 900
ccaatcagtt tcctgctgtc cgatttgatc aatcgccgca cacaacgcgt cgacggccag 960
cccatgtacg gcatggaaag ccaagtcgaa gaagtgcgcg tcttcgacgg gaccgagaag 1020
ttgcccggcg atcccgacat gatccgctac atcgatcgcc aaggccagct ccaaaccaag 1080
atggtctga 1089

<210> SEQ ID NO 48
<211> LENGTH: 1065
<212> TYPE: DNA
<213> ORGANISM: Artificial Sequence
<220> FEATURE:
<223> OTHER INFORMATION: Codon-optimized JCV-2A VP1

<400> SEQUENCE: 48
atggcaccca caaagcgcaa gggcgaacgc aaggacccag tccaggtccc caagttgctg 60
atcaggggcg gcgtggaggt cctggaggtc aagaccggcg tggactccat caccgaggtg 120
gagtgtttct tgacacccga gatgggcgac cccgacgagc acctgcgcgg gttcagcaag 180
agcatcagca tcagcgacac attcgagtcc gactcaccca ataaggacat gttgccatgc 240
tattccgtcg cccgcatccc actgcccaac ctcaacgaag acttgacatg cggcaacatc 300
ctgatgtggg aagccgtcac actgaagacc gaagtcatcg gcgtcaccac cctgatgaat 360
gtgcactcca acggccaagc gacgcacgac aacggcgccg ggaagccagt ccaggggaca 420
agcttccatt tcttcagcgt cggcggcgag gcactcgagc tgcaaggcgt ggtgttcaac 480
tatcgcacca agtatcccga cggcaccata ttccccaaga acgcaaccgt ccaaagtcag 540
gtcatgaaca ccgagcacaa agcatatctc gataagaata aggcctaccc cgtcgagtgt 600
tgggtccccg atccaaccag gaacgagaac acccgctact tcggcaccct gaccggcggc 660
gagaacgtcc cacccgtgtt gcacatcaca aataccgcca caaccgtcct gctcgacgag 720
ttcggcgtcg gcccactctg caagggagac aacctctacc tgagcgccgt cgacgtctgc 780
ggaatgttca ccaatcgaag cggcagccag caatggcgcg ggttgtcccg ctacttcaaa 840
gtccagctcc gcaagcgccg cgtgaagaat ccctatccaa tcagtttcct gctgaccgat 900
ttgatcaatc gccgcacacc acgcgtcgac ggccagccca tgtacggcat ggacgcccaa 960
gtcgaagaag tgcgcgtatt cgaggggacc gaggagttgc ccggcgatcc cgacatgatg 1020
cgctacgtcg atcgctacgg ccagctccaa accaagatgc tatga 1065

<210> SEQ ID NO 49
<211> LENGTH: 1065
<212> TYPE: DNA
<213> ORGANISM: Artificial Sequence
<220> FEATURE:
<223> OTHER INFORMATION: Codon-optimzed JCV-3B VP1

<400> SEQUENCE: 49
atggcaccca caaagcgcaa gggcgaacgc aaggacccag tccaggtccc caagttgctg 60
atcaggggcg gcgtggaggt cctggaggtc aagaccggcg tggactccat caccgaggtg 120
gagtgtttct tgacacccga gatgggcgac cccgacgagc acttccgcgg gttcagcaag 180
agcatcagca tcagcgacac attcgagtcc gactcaccca ataaggacat gttgccatgc 240
tattccgtcg cccgcatccc actgcccaac ctcaacgaag acttgacatg cggcaacatc 300
ctgatgtggg aagccgtcac actgaagacc gaagtcatcg gcgtcaccac cctgatgaat 360
gtgcactcca acggccaagc gacgcacgac aacggcgccg cgaagccagt ccaggggaca 420
agcttccatt tcttcagcgt cggcggcgag gcactcgagc tgcaaggcgt ggtgttcaac 480
tatcgcacca cgtatcccga cggcaccata ttccccaaga acgcaaccgt ccaaagtcag 540
gtcatgaaca ccgagcacaa agcatatctc gataagaata aggcctaccc cgtcgagtgt 600
tgggtccccg atccaaccag gaacgagaac acccgctact tcggcaccct gaccggcggc 660
gagaacgtcc cacccgtgtt gcacatcaca aataccgcca caaccgtcct gctcgacgag 720
ttcggcgtcg gcccactctg caagggagac aacctctacc tgagcgccgt cgacgtctgc 780
ggaatgttca ccaatcgaag cggcagccag caatggcgcg ggttgtcccg ctacttcaaa 840
gtccagctcc gcaagcgccg cgtgaagaat ccctatccaa tcagtttcct gctgaccgat 900
ttgatcaatc gccgcacacc acgcgtcgac ggccagccca tgtacggcat ggacgcccaa 960
atcgaagaag tgcgcgtatt cgaggggacc gagcagttgc ccggcgatcc cgacatgatg 1020
cgctacgtcg atcgctacgg ccagctccaa accaagatgc tatga 1065

<210> SEQ ID NO 50
<211> LENGTH: 1035
<212> TYPE: DNA
<213> ORGANISM: Artificial Sequence
<220> FEATURE:
<223> OTHER INFORMATION: Codon-optimized JCV VP2 consensus

<400> SEQUENCE: 50
atgggcgcag ctctggcctt gctcggcgat ctggtcgcca ccgtcagcga agccgcagcc 60
gcaaccggat tcagcgtggc cgagatcgca gccggagaag ctgcagccac aatcgaggtc 120
gagatcgcca gtttggccac tgtggaaggc atcacctcca caagcgaagc catcgctgcc 180
atcggactga cacccgagac ctacgccgtg atcactggcg cacccggagc cgtggcagga 240
ttcgccgcac tcgtccaaac cgtgaccggc ggctccgcca tcgcccaact cgggtaccgg 300
ttcttcgccg attgggacca caaggtcagc accgtcggct tgttccaaca acccgcaatg 360
gcactgcagc tgttcaaccc cgaggactac tacgacatcc tgttcccggg cgtcaacgca 420
ttcgtcaaca acatccatta cctggaccca cgccactggg ggcccagcct gttttcgacc 480
attagtcaag cattctggaa cttggtccgc gacgacctgc caagcctgac cagccaagag 540
atccagcgcc gcacacagaa gttgttcgtc gagtccctgg cccgcttcct ggaagagaca 600
acctgggcca tcgtcaacag ccccgtcaat ctgtacaact acatcagcga ttactactcg 660
cgactcagcc ccgtccgccc aagcatggtc cgccaagtcg cacagcgcga aggcacatac 720
atcagtttcg ggcatagcta tacacagtcc atcgacgacg ccgattcaat ccaggaggtc 780
acacagcgct tggacctgaa gacacccaac gtccagagcg gcgagttcat cgaaaagtcc 840
atcgcccctg gcggagcaaa ccagcgcagc gcaccacaat ggatgctgcc actgttgctg 900
ggcctctatg gcaccgtgac cccagcactg gaggcctacg aggacggacc aaacaagaaa 960
aagcgccgca aggaaggccc aagggcatcc agcaagacca gctacaaacg tcggtccagg 1020
tccagccgct cctga 1035

<210> SEQ ID NO 51
<211> LENGTH: 678
<212> TYPE: DNA
<213> ORGANISM: Artificial Sequence
<220> FEATURE:
<223> OTHER INFORMATION: Codon-optimized JCV VP3 consensus

<400> SEQUENCE: 51
atggcactgc agctgttcaa ccccgaggac tactacgaca tcctgttccc gggcgtcaac 60
gcattcgtca acaacatcca ttacctggac ccacgccact gggggcccag cctgttttcg 120
accattagtc aagcattctg gaacttggtc cgcgacgacc tgccaagcct gaccagccaa 180
gagatccagc gccgcacaca gaagttgttc gtcgagtccc tggcccgctt cctggaagag 240
acaacctggg ccatcgtcaa cagccccgtc aatctgtaca actacatcag cgattactac 300
tcgcgactca gccccgtccg cccaagcatg gtccgccaag tcgcacagcg cgaaggcaca 360
tacatcagtt tcgggcatag ctatacacag tccatcgacg acgccgattc aatccaggag 420
gtcacacagc gcttggacct gaagacaccc aacgtccaga gcggcgagtt catcgaaaag 480
tccatcgccc ctggcggagc aaaccagcgc agcgcaccac aatggatgct gccactgttg 540
ctgggcctct atggcaccgt gaccccagca ctggaggcct acgaggacgg accaaacaag 600
aaaaagcgcc gcaaggaagg cccaagggca tccagcaaga ccagctacaa acgtcggtcc 660
aggtccagcc gctcctga 678

<210> SEQ ID NO 52
<211> LENGTH: 362
<212> TYPE: PRT
<213> ORGANISM: BK virus

<400> SEQUENCE: 52

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Ala Glu Asn Asp Phe Ser Ser Asp Ser
65 70 75 80

Pro Glu Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Asp Gly
165 170 175

```
Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 53
<211> LENGTH: 362
<212> TYPE: PRT
<213> ORGANISM: BK virus

<400> SEQUENCE: 53

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
```

-continued

```
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 54
<211> LENGTH: 362
<212> TYPE: PRT
<213> ORGANISM: BK virus

<400> SEQUENCE: 54

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Ile Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190
```

-continued

```
Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 55
<211> LENGTH: 362
<212> TYPE: PRT
<213> ORGANISM: BK virus

<400> SEQUENCE: 55

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Pro Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205
```

```
Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 56
<211> LENGTH: 362
<212> TYPE: PRT
<213> ORGANISM: BK virus

<400> SEQUENCE: 56

Met Ala Pro Thr Lys Arg Lys Gly Glu Cys Pro Gly Ala Ala Pro Lys
1               5                   10                  15

Lys Pro Glu Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
```

```
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 57
<211> LENGTH: 362
<212> TYPE: PRT
<213> ORGANISM: BK virus

<400> SEQUENCE: 57

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Leu Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220
```

```
Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 58
<211> LENGTH: 362
<212> TYPE: PRT
<213> ORGANISM: BK virus

<400> SEQUENCE: 58

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240
```

```
Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 59
<211> LENGTH: 362
<212> TYPE: PRT
<213> ORGANISM: BK virus

<400> SEQUENCE: 59

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Ser Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
```

-continued

```
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 60
<211> LENGTH: 362
<212> TYPE: PRT
<213> ORGANISM: BK virus

<400> SEQUENCE: 60

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255
```

-continued

```
Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Arg Gln Gly Gln Leu Gln Thr Lys Met Leu
        355                 360


<210> SEQ ID NO 61
<211> LENGTH: 362
<212> TYPE: PRT
<213> ORGANISM: BK virus

<400> SEQUENCE: 61

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270
```

```
Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Thr Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 62
<211> LENGTH: 362
<212> TYPE: PRT
<213> ORGANISM: BK virus

<400> SEQUENCE: 62

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Glu Pro Leu
145                 150                 155                 160

Glu Met Gln Gly Val Leu Met Asn Tyr Arg Ser Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Ala Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
```

275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Arg Leu Pro Gly Asp Pro Asp Met Ile Arg Tyr Ile Asp
340 345 350

Lys Gln Gly Gln Leu Gln Thr Lys Met Leu
355 360

<210> SEQ ID NO 63
<211> LENGTH: 362
<212> TYPE: PRT
<213> ORGANISM: BK virus

<400> SEQUENCE: 63

Met Ala Pro Ala Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Ala Glu Asn Asp Phe Ser Ser Asp Ser
65 70 75 80

Pro Glu Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Asp Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Val Pro Asp Pro Ser Arg Asn Glu Asn Thr Arg Tyr Phe Gly Thr
210 215 220

Phe Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Arg
275 280 285

-continued

```
Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Gly Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 64
<211> LENGTH: 362
<212> TYPE: PRT
<213> ORGANISM: BK virus

<400> SEQUENCE: 64

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Leu Ile Ser Phe
    290                 295                 300
```

```
Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 65
<211> LENGTH: 362
<212> TYPE: PRT
<213> ORGANISM: BK virus

<400> SEQUENCE: 65

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Thr Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Gly Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Thr Arg Leu Arg Lys Arg Ser Val Lys Asn Pro Tyr Pro Ile Ser Ser
    290                 295                 300

Leu Leu Ser Asp Leu Ile Asn Arg Arg Thr Gln Arg Val Asp Gly Gln
```

-continued

```
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 66
<211> LENGTH: 362
<212> TYPE: PRT
<213> ORGANISM: BK virus

<400> SEQUENCE: 66

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Gln Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Arg Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Ser Leu Ser Asp Leu Ile Asn Arg Arg Thr Gln Arg Val Asp Gly Gln
305                 310                 315                 320
```

-continued

```
Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 67
<211> LENGTH: 362
<212> TYPE: PRT
<213> ORGANISM: BK virus

<400> SEQUENCE: 67

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335
```

```
Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 68
<211> LENGTH: 362
<212> TYPE: PRT
<213> ORGANISM: BK virus

<400> SEQUENCE: 68

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Tyr Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Tyr Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
```

```
            340                 345                 350

Lys Gln Gly Gln Leu Gln Thr Lys Met Leu
        355                 360


<210> SEQ ID NO 69
<211> LENGTH: 362
<212> TYPE: PRT
<213> ORGANISM: BK virus

<400> SEQUENCE: 69

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asn Glu Asn Leu Arg
    50                  55                  60

Gly Phe Ser Leu Met Leu Ser Ala Glu Asn Asp Phe Asn Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350
```

```
Lys Gln Gly Gln Leu Gln Thr Lys Met Leu
        355                 360


<210> SEQ ID NO 70
<211> LENGTH: 362
<212> TYPE: PRT
<213> ORGANISM: BK virus

<400> SEQUENCE: 70

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asn Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 71
<211> LENGTH: 362
<212> TYPE: PRT
<213> ORGANISM: BK virus

<400> SEQUENCE: 71

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Gln Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

-continued

```
<210> SEQ ID NO 72
<211> LENGTH: 362
<212> TYPE: PRT
<213> ORGANISM: BK virus

<400> SEQUENCE: 72

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Gln Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Trp Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 73
<211> LENGTH: 362
```

<212> TYPE: PRT
<213> ORGANISM: BK virus

<400> SEQUENCE: 73

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Lys Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 74
<211> LENGTH: 362
<212> TYPE: PRT
<213> ORGANISM: BK virus

-continued

<400> SEQUENCE: 74

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Asp Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Val Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 75
<211> LENGTH: 362
<212> TYPE: PRT
<213> ORGANISM: BK virus

<400> SEQUENCE: 75

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Lys Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

```
<210> SEQ ID NO 76
<211> LENGTH: 362
<212> TYPE: PRT
<213> ORGANISM: BK virus

<400> SEQUENCE: 76

Met Ala Pro Thr Lys Arg Lys Gly Glu Cys Pro Gly Ala Ala Pro Lys
```

-continued

```
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Gln Asn Asp Phe Asn Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360
```

```
<210> SEQ ID NO 77
<211> LENGTH: 362
<212> TYPE: PRT
<213> ORGANISM: BK virus

<400> SEQUENCE: 77

Met Ala Pro Thr Lys Arg Lys Gly Glu Cys Pro Gly Ala Ala Pro Lys
1               5                   10                  15
```

-continued

```
Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 78
<211> LENGTH: 362
<212> TYPE: PRT
<213> ORGANISM: BK virus

<400> SEQUENCE: 78

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30
```

```
Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360
```

```
<210> SEQ ID NO 79
<211> LENGTH: 362
<212> TYPE: PRT
<213> ORGANISM: BK virus

<400> SEQUENCE: 79

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
```

-continued

```
        35                  40                  45

Glu Cys Phe Leu Asn Pro Glu Met Gly Asp Pro Asn Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 80
<211> LENGTH: 362
<212> TYPE: PRT
<213> ORGANISM: BK virus

<400> SEQUENCE: 80

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45
```

-continued

Glu Cys Phe Leu Asn Pro Glu Met Gly Asp Pro Asp Glu Asn Leu Arg
50 55 60

Gly Phe Ser Leu Lys Leu Ser Ala Glu Asn Asp Phe Ser Ser Asp Ser
65 70 75 80

Pro Glu Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Ile Thr Pro Lys Asn Pro Thr Ala Gln Ser Gln Val Met Asn Thr
180 185 190

Asp His Met Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Phe Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Lys Leu Pro Gly Asp Pro Asp Met Ile Arg Tyr Ile Asp
340 345 350

Lys Gln Gly Gln Leu Gln Thr Lys Met Leu
355 360

<210> SEQ ID NO 81
<211> LENGTH: 362
<212> TYPE: PRT
<213> ORGANISM: BK virus

<400> SEQUENCE: 81

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Leu Asp Ala Ile Thr Glu Val
35 40 45

Glu Cys Phe Leu Asn Pro Glu Met Gly Asp Pro Asp Glu Asn Leu Arg
50 55 60

-continued

```
Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Thr Arg Asn Glu Asn Thr Arg Tyr Phe Gly Thr
    210                 215                 220

Phe Thr Gly Gly Glu Asn Val Pro Pro Val Leu His Ile Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 82
<211> LENGTH: 362
<212> TYPE: PRT
<213> ORGANISM: BK virus

<400> SEQUENCE: 82

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
```

```
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Ser Ser Arg Asp Pro Asp Met Ile Arg Tyr Ile Asp
            340                 345                 350

Lys Gln Gly Gln Leu Gln Thr Lys Met Leu
        355                 360


<210> SEQ ID NO 83
<211> LENGTH: 362
<212> TYPE: PRT
<213> ORGANISM: BK virus

<400> SEQUENCE: 83

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80
```

-continued

```
Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360
```

<210> SEQ ID NO 84
<211> LENGTH: 362
<212> TYPE: PRT
<213> ORGANISM: BK virus

<400> SEQUENCE: 84

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95
```

-continued

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Phe Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Arg Leu Pro Gly Asp Pro Asp Met Ile Arg Tyr Ile Asp
340 345 350

Lys Gln Gly Gln Leu Gln Thr Lys Met Val
355 360

<210> SEQ ID NO 85
<211> LENGTH: 362
<212> TYPE: PRT
<213> ORGANISM: BK virus

<400> SEQUENCE: 85

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Leu Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Ala Glu Asn Asp Phe Ser Ser Asp Ser
65 70 75 80

Pro Glu Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu

```
            100                 105                 110

Ala Val Thr Val Gln Thr Glu Val Ile Gly Ile Thr Ser Met Leu Asn
        115                 120                 125

Leu His Ala Gly Ser Lys Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360


<210> SEQ ID NO 86
<211> LENGTH: 362
<212> TYPE: PRT
<213> ORGANISM: BK virus

<400> SEQUENCE: 86

Met Ala Pro Thr Lys Arg Lys Gly Glu Cys Pro Gly Ala Ala Pro Lys
1               5                   10                  15

Lys Pro Lys Glu Pro Met Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110
```

-continued

```
Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360
```

```
<210> SEQ ID NO 87
<211> LENGTH: 362
<212> TYPE: PRT
<213> ORGANISM: BK virus

<400> SEQUENCE: 87

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125
```

-continued

```
Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asn Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360


<210> SEQ ID NO 88
<211> LENGTH: 362
<212> TYPE: PRT
<213> ORGANISM: BK virus

<400> SEQUENCE: 88

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
```

```
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Gly Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Val
        355                 360


<210> SEQ ID NO 89
<211> LENGTH: 362
<212> TYPE: PRT
<213> ORGANISM: BK virus

<400> SEQUENCE: 89

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140
```

```
Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360
```

<210> SEQ ID NO 90
<211> LENGTH: 362
<212> TYPE: PRT
<213> ORGANISM: BK virus

<400> SEQUENCE: 90

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160
```

```
Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 91
<211> LENGTH: 362
<212> TYPE: PRT
<213> ORGANISM: BK virus

<400> SEQUENCE: 91

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Arg Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
```

```
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 92
<211> LENGTH: 362
<212> TYPE: PRT
<213> ORGANISM: BK virus

<400> SEQUENCE: 92

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Val Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175
```

```
Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 93
<211> LENGTH: 362
<212> TYPE: PRT
<213> ORGANISM: BK virus

<400> SEQUENCE: 93

Met Ala Pro Thr Lys Lys Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Leu Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190
```

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Phe Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Arg Leu Pro Gly Asp Pro Asp Met Ile Arg Tyr Ile Asp
340 345 350

Lys Gln Gly Gln Leu Gln Thr Lys Met Leu
355 360

<210> SEQ ID NO 94
<211> LENGTH: 362
<212> TYPE: PRT
<213> ORGANISM: BK virus

<400> SEQUENCE: 94

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Ala Glu Asn Asp Phe Ser Ser Asp Ser
65 70 75 80

Pro Asp Lys Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys

```
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 95
<211> LENGTH: 362
<212> TYPE: PRT
<213> ORGANISM: BK virus

<400> SEQUENCE: 95

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Lys Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205
```

-continued

```
Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 96
<211> LENGTH: 362
<212> TYPE: PRT
<213> ORGANISM: BK virus

<400> SEQUENCE: 96

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220
```

```
Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 97
<211> LENGTH: 362
<212> TYPE: PRT
<213> ORGANISM: BK virus

<400> SEQUENCE: 97

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asn Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
```

```
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 98
<211> LENGTH: 362
<212> TYPE: PRT
<213> ORGANISM: BK virus

<400> SEQUENCE: 98

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Gln Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240
```

-continued

```
Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 99
<211> LENGTH: 362
<212> TYPE: PRT
<213> ORGANISM: BK virus

<400> SEQUENCE: 99

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255
```

```
Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 100
<211> LENGTH: 362
<212> TYPE: PRT
<213> ORGANISM: BK virus

<400> SEQUENCE: 100

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Leu Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
```

```
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 101
<211> LENGTH: 362
<212> TYPE: PRT
<213> ORGANISM: BK virus

<400> SEQUENCE: 101

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270
```

```
Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Lys Gln Gly Gln Leu Gln Thr Lys Met Leu
        355                 360


<210> SEQ ID NO 102
<211> LENGTH: 362
<212> TYPE: PRT
<213> ORGANISM: BK virus

<400> SEQUENCE: 102

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285
```

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Lys Leu Pro Gly Asp Pro Asp Met Ile Arg Tyr Ile Asp
340 345 350

Lys Gln Gly Gln Leu Gln Thr Lys Met Leu
355 360

<210> SEQ ID NO 103
<211> LENGTH: 362
<212> TYPE: PRT
<213> ORGANISM: BK virus

<400> SEQUENCE: 103

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Glu Asn Leu Arg
50 55 60

Gly Phe Ser Leu Lys Leu Ser Val Glu Asn Asp Phe Ser Ser Asp Ser
65 70 75 80

Pro Gln Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Gln Thr Glu Val Ile Gly Ile Thr Ser Met Leu Asn
115 120 125

Leu His Ala Gly Ser Gln Lys Val His Glu His Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Leu Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe 290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Lys Leu Pro Gly Asp Pro Asp Met Ile Arg Tyr Ile Asp
340 345 350

Lys Gln Gly Gln Leu Gln Thr Lys Met Leu
355 360

<210> SEQ ID NO 104
<211> LENGTH: 362
<212> TYPE: PRT
<213> ORGANISM: BK virus

<400> SEQUENCE: 104

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Glu Asn Leu Arg
50 55 60

Gly Tyr Ser Leu Lys Leu Thr Ala Glu Asn Ala Phe Asp Ser Asp Ser
65 70 75 80

Pro Asp Lys Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Glu Asn Gly Gly Gly Lys Pro
130 135 140

Val Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Gln Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

-continued

Leu Leu Ser Asp Leu Ile Asn Arg Arg Thr Gln Lys Val Asp Gly Gln
305 310 315 320

Pro Met Tyr Gly Met Glu Ser Gln Val Glu Glu Val Arg Val Phe Asp
325 330 335

Gly Thr Glu Gln Leu Pro Gly Asp Pro Asp Met Ile Arg Tyr Ile Asp
340 345 350

Arg Gln Gly Gln Leu Gln Thr Lys Met Val
355 360

<210> SEQ ID NO 105
<211> LENGTH: 362
<212> TYPE: PRT
<213> ORGANISM: BK virus

<400> SEQUENCE: 105

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asn Asp Leu Arg
50 55 60

Gly Tyr Ser Leu Lys Leu Thr Ala Glu Asn Ala Phe Asp Ser Asp Ser
65 70 75 80

Pro Asp Lys Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Glu Asn Gly Gly Gly Lys Pro
130 135 140

Val Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Gln Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Lys Val Asp Gly Gln
305 310 315 320

```
Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 106
<211> LENGTH: 362
<212> TYPE: PRT
<213> ORGANISM: BK virus

<400> SEQUENCE: 106

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asp Asn Leu Arg
    50                  55                  60

Gly Tyr Ser Leu Lys Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
```

-continued 325 330 335

Gly Thr Glu Gln Leu Pro Gly Asp Pro Asp Met Ile Arg Tyr Ile Asp
340 345 350

Arg Gln Gly Gln Leu Gln Thr Lys Met Val
355 360

<210> SEQ ID NO 107
<211> LENGTH: 362
<212> TYPE: PRT
<213> ORGANISM: BK virus

<400> SEQUENCE: 107

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asp His Leu Arg
50 55 60

Gly Tyr Ser Gln His Leu Thr Ala Glu Asn Ala Phe Asp Ser Asp Ser
65 70 75 80

Pro Asp Lys Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Glu Asn Gly Gly Gly Lys Pro
130 135 140

Val Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Gln Gly
165 170 175

Thr Ile Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Lys Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Ala Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Lys Val Asp Gly Gln
305 310 315 320

Pro Met Tyr Gly Met Glu Ser Gln Val Glu Glu Val Arg Val Phe Asp
325 330 335

```
Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 108
<211> LENGTH: 362
<212> TYPE: PRT
<213> ORGANISM: BK virus

<400> SEQUENCE: 108

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asp Asn Leu Arg
    50                  55                  60

Gly Tyr Ser Gln His Leu Ser Ala Glu Asn Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350
```

```
Arg Gln Gly Gln Leu Gln Thr Lys Met Val
        355                 360


<210> SEQ ID NO 109
<211> LENGTH: 362
<212> TYPE: PRT
<213> ORGANISM: BK virus

<400> SEQUENCE: 109

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Tyr Ser Gln His Leu Ser Ala Glu Asn Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
```

355 360

<210> SEQ ID NO 110
<211> LENGTH: 362
<212> TYPE: PRT
<213> ORGANISM: BK virus

<400> SEQUENCE: 110

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asn Asp Leu Arg
50 55 60

Gly Tyr Ser Leu Arg Leu Thr Ala Glu Thr Ala Phe Asp Ser Asp Ser
65 70 75 80

Pro Asp Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Glu Asn Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Val Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Pro Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Gln Leu Pro Gly Asp Pro Asp Met Ile Arg Tyr Ile Asp
340 345 350

Arg Gln Gly Gln Leu Gln Thr Lys Met Val
355 360

<210> SEQ ID NO 111
<211> LENGTH: 362
<212> TYPE: PRT
<213> ORGANISM: BK virus

<400> SEQUENCE: 111

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asn Asp Leu Arg
50 55 60

Gly Tyr Ser Leu Arg Leu Thr Ala Glu Thr Ala Phe Asp Ser Asp Ser
65 70 75 80

Pro Asp Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Asp Asn Gly Gly Gly Lys Pro
130 135 140

Ile Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Val Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Pro Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Lys Leu Pro Gly Asp Pro Asp Met Ile Arg Tyr Ile Asp
340 345 350

Arg Gln Gly Gln Leu Gln Thr Lys Met Val
355 360

<210> SEQ ID NO 112

<211> LENGTH: 362
<212> TYPE: PRT
<213> ORGANISM: BK virus

<400> SEQUENCE: 112

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Met Gly Ile Thr Ser Met Leu Asn
        115                 120                 125

Leu His Ala Gly Ser Gln Lys Val His Asp Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360
```

<210> SEQ ID NO 113
<211> LENGTH: 362
<212> TYPE: PRT

```
<213> ORGANISM: BK virus

<400> SEQUENCE: 113

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Met Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 114
<211> LENGTH: 362
<212> TYPE: PRT
<213> ORGANISM: BK virus
```

<400> SEQUENCE: 114

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Met Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Ile
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360

<210> SEQ ID NO 115
<211> LENGTH: 362
<212> TYPE: PRT
<213> ORGANISM: BK virus

<400> SEQUENCE: 115

-continued

Met Ala Pro Thr Lys Arg Lys Gly Glu Cys Pro Gly Ala Ala Pro Lys
1 5 10 15

Lys Pro Lys Glu Pro Val Gln Val Pro Lys Leu Leu Ile Lys Gly Gly
20 25 30

Val Glu Val Leu Glu Val Lys Thr Gly Val Asp Ala Ile Thr Glu Val
35 40 45

Glu Cys Phe Leu Asn Pro Glu Met Gly Asp Pro Asp Asn Asp Leu Arg
50 55 60

Gly Tyr Ser Leu Arg Leu Thr Ala Glu Thr Ala Phe Asp Ser Asp Ser
65 70 75 80

Pro Asp Arg Lys Met Leu Pro Cys Tyr Ser Thr Ala Arg Ile Pro Leu
85 90 95

Pro Asn Leu Asn Glu Asp Leu Thr Cys Gly Asn Leu Leu Met Trp Glu
100 105 110

Ala Val Thr Val Lys Thr Glu Val Ile Gly Ile Thr Ser Met Leu Asn
115 120 125

Leu His Ala Gly Ser Gln Lys Val His Gln Asn Gly Gly Gly Lys Pro
130 135 140

Val Gln Gly Ser Asn Phe His Phe Phe Ala Val Gly Gly Asp Pro Leu
145 150 155 160

Glu Met Gln Gly Val Leu Met Asn Tyr Arg Thr Lys Tyr Pro Glu Gly
165 170 175

Thr Val Thr Pro Lys Asn Pro Thr Ala Gln Ser Gln Val Met Asn Thr
180 185 190

Asp His Lys Ala Tyr Leu Asp Lys Asn Asn Ala Tyr Pro Val Glu Cys
195 200 205

Trp Ile Pro Asp Pro Ser Arg Asn Glu Asn Thr Arg Tyr Phe Gly Thr
210 215 220

Tyr Thr Gly Gly Glu Asn Val Pro Pro Val Leu His Val Thr Asn Thr
225 230 235 240

Ala Thr Thr Val Leu Leu Asp Glu Gln Gly Val Gly Pro Leu Cys Lys
245 250 255

Ala Asp Ser Leu Tyr Val Ser Ala Ala Asp Ile Cys Gly Leu Phe Thr
260 265 270

Asn Ser Ser Gly Thr Gln Gln Trp Arg Gly Leu Pro Arg Tyr Phe Lys
275 280 285

Ile Arg Leu Arg Lys Arg Ser Val Lys Asn Pro Tyr Pro Ile Ser Phe
290 295 300

Leu Leu Ser Asp Leu Ile Asn Arg Arg Thr Gln Arg Val Asp Gly Gln
305 310 315 320

Pro Met Tyr Gly Met Glu Ser Gln Val Glu Glu Val Arg Val Phe Asp
325 330 335

Gly Thr Glu Gln Leu Pro Gly Asp Pro Asp Met Ile Arg Tyr Ile Asp
340 345 350

Arg Gln Gly Gln Leu Gln Thr Lys Met Val
355 360

<210> SEQ ID NO 116
<211> LENGTH: 362
<212> TYPE: PRT
<213> ORGANISM: BK virus

<400> SEQUENCE: 116

Met Ala Pro Thr Lys Arg Lys Gly Glu Cys Pro Gly Ala Ala Pro Lys
1 5 10 15

```
Lys Pro Lys Asp Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 117
<211> LENGTH: 362
<212> TYPE: PRT
<213> ORGANISM: BK virus

<400> SEQUENCE: 117

Met Ala Pro Thr Lys Arg Lys Gly Glu Cys Pro Gly Ala Ala Pro Lys
1               5                   10                  15

Lys Pro Lys Asp Pro Val Gln Val Pro Lys Leu Leu Ile Lys Gly Gly
```

-continued

```
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 118
<211> LENGTH: 362
<212> TYPE: PRT
<213> ORGANISM: BK virus

<400> SEQUENCE: 118

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30
```

-continued

```
Val Glu Val Leu Glu Val Lys Thr Gly Val Asp Ala Ile Thr Glu Val
        35                  40                  45

Glu Cys Phe Leu Asn Pro Glu Met Gly Asp Pro Asp Ser Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 119
<211> LENGTH: 362
<212> TYPE: PRT
<213> ORGANISM: BK virus

<400> SEQUENCE: 119

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45
```

```
Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 120
<211> LENGTH: 362
<212> TYPE: PRT
<213> ORGANISM: BK virus

<400> SEQUENCE: 120

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
```

```
    50                  55                  60

Gly Tyr Ser Leu Arg Leu Thr Ala Glu Thr Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 121
<211> LENGTH: 362
<212> TYPE: PRT
<213> ORGANISM: BK virus

<400> SEQUENCE: 121

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60
```

-continued

```
Gly Tyr Ser Leu Arg Leu Thr Ala Glu Thr Ala Phe Lys Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360
```

<210> SEQ ID NO 122
<211> LENGTH: 362
<212> TYPE: PRT
<213> ORGANISM: BK virus

<400> SEQUENCE: 122

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80
```

-continued

```
Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Met Arg Lys Arg Ser Val Lys Asn Pro Tyr Pro Ile Ser Phe
    290                 295                 300

Phe Ile Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Met Pro Asp Leu Ile Arg Tyr Ile Asp
            340                 345                 350

Arg Gln Gly Gln Leu Gln Thr Lys Met Val
        355                 360


<210> SEQ ID NO 123
<211> LENGTH: 362
<212> TYPE: PRT
<213> ORGANISM: BK virus
<220> FEATURE:
<221> NAME/KEY: misc_feature
<222> LOCATION: (186)..(186)
<223> OTHER INFORMATION: Xaa can be any naturally occurring amino acid

<400> SEQUENCE: 123

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60
```

```
Gly Tyr Ser Leu Arg Leu Thr Ala Glu Thr Ala Phe Asn Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Xaa Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 124
<211> LENGTH: 362
<212> TYPE: PRT
<213> ORGANISM: BK virus

<400> SEQUENCE: 124

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asp Ser Asp Ser
65                  70                  75                  80
```

-continued

```
Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Lys Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 125
<211> LENGTH: 362
<212> TYPE: PRT
<213> ORGANISM: BK virus

<400> SEQUENCE: 125

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asn Asp Leu Arg
    50                  55                  60

Gly Tyr Ser Leu Arg Leu Thr Ala Glu Thr Ala Phe Asn Ser Asp Ser
65                  70                  75                  80

Pro Asp Arg Lys Met Leu Pro Cys Tyr Ser Thr Ala Arg Ile Pro Leu
```

-continued

```
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Asp Asn Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Pro Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Lys Leu Pro Gly Asp Pro Asp Met Ile Arg Tyr Ile Asp
            340                 345                 350

Arg Gln Gly Gln Leu Gln Thr Lys Met Val
        355                 360


<210> SEQ ID NO 126
<211> LENGTH: 144
<212> TYPE: PRT
<213> ORGANISM: BK virus

<400> SEQUENCE: 126

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95
```

```
Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 127
<211> LENGTH: 144
<212> TYPE: PRT
<213> ORGANISM: BK virus

<400> SEQUENCE: 127

Gly Gly Val Glu Val Leu Glu Val Lys Thr Gly Leu Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 128
<211> LENGTH: 144
<212> TYPE: PRT
<213> ORGANISM: BK virus

<400> SEQUENCE: 128

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Asp Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140
```

<210> SEQ ID NO 129
<211> LENGTH: 144
<212> TYPE: PRT
<213> ORGANISM: BK virus

<400> SEQUENCE: 129

Gly Gly Val Glu Val Leu Glu Val Lys Thr Gly Val Asp Ala Ile Thr
1 5 10 15

Glu Val Glu Cys Phe Leu Asn Pro Glu Met Gly Asp Pro Asp Asn Asp
20 25 30

Leu Arg Gly Tyr Ser Leu Arg Leu Thr Ala Glu Thr Ala Phe Glu Ser
35 40 45

Asp Ser Pro Asp Arg Lys Met Leu Pro Cys Tyr Ser Thr Ala Arg Ile
50 55 60

Pro Leu Pro Asn Leu Asn Glu Asp Leu Thr Cys Gly Asn Leu Leu Met
65 70 75 80

Trp Glu Ala Val Thr Val Lys Thr Glu Val Ile Gly Ile Thr Ser Met
85 90 95

Leu Asn Leu His Ala Gly Ser Gln Lys Val His Glu Asn Gly Gly Gly
100 105 110

Lys Pro Ile Gln Gly Ser Asn Phe His Phe Phe Ala Val Gly Gly Asp
115 120 125

Pro Leu Glu Met Gln Gly Val Leu Met Asn Tyr Arg Thr Ser Tyr Pro
130 135 140

<210> SEQ ID NO 130
<211> LENGTH: 144
<212> TYPE: PRT
<213> ORGANISM: BK virus

<400> SEQUENCE: 130

Gly Gly Val Glu Val Leu Glu Val Lys Thr Gly Val Asp Ala Ile Thr
1 5 10 15

Glu Val Glu Cys Phe Leu Asn Pro Glu Met Gly Asp Pro Asp Asn Asp
20 25 30

Leu Arg Gly Tyr Ser Leu Arg Leu Thr Ala Glu Thr Ala Phe Glu Ser
35 40 45

Asp Ser Pro Asp Arg Lys Met Leu Pro Cys Tyr Ser Thr Ala Arg Ile
50 55 60

Pro Leu Pro Asn Leu Asn Glu Asp Leu Thr Cys Gly Asn Leu Leu Met
65 70 75 80

Trp Glu Ala Val Thr Val Lys Thr Glu Val Ile Gly Ile Thr Ser Met
85 90 95

Leu Asn Leu His Ala Gly Ser Gln Lys Val His Glu Asn Gly Gly Gly
100 105 110

Lys Pro Ile Gln Gly Ser Asn Phe His Phe Phe Ala Val Gly Gly Asp
115 120 125

Pro Leu Glu Met Gln Gly Val Leu Met Asn Tyr Arg Thr Lys Tyr Pro
130 135 140

<210> SEQ ID NO 131
<211> LENGTH: 144
<212> TYPE: PRT
<213> ORGANISM: BK virus

<400> SEQUENCE: 131

Gly Gly Val Glu Val Leu Glu Val Lys Thr Gly Val Asp Ala Ile Thr

```
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 132
<211> LENGTH: 144
<212> TYPE: PRT
<213> ORGANISM: BK virus

<400> SEQUENCE: 132

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 133
<211> LENGTH: 144
<212> TYPE: PRT
<213> ORGANISM: BK virus

<400> SEQUENCE: 133

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Ser Asp
            20                  25                  30

Leu Arg Gly Tyr Arg Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
```

```
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 134
<211> LENGTH: 144
<212> TYPE: PRT
<213> ORGANISM: BK virus

<400> SEQUENCE: 134

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Trp Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 135
<211> LENGTH: 144
<212> TYPE: PRT
<213> ORGANISM: BK virus

<400> SEQUENCE: 135

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
```

```
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 136
<211> LENGTH: 144
<212> TYPE: PRT
<213> ORGANISM: BK virus

<400> SEQUENCE: 136

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Leu His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 137
<211> LENGTH: 144
<212> TYPE: PRT
<213> ORGANISM: BK virus

<400> SEQUENCE: 137

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140
```

```
<210> SEQ ID NO 138
<211> LENGTH: 144
<212> TYPE: PRT
<213> ORGANISM: BK virus

<400> SEQUENCE: 138

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Ala Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 139
<211> LENGTH: 144
<212> TYPE: PRT
<213> ORGANISM: BK virus

<400> SEQUENCE: 139

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Arg Tyr Pro
    130                 135                 140


<210> SEQ ID NO 140
<211> LENGTH: 144
<212> TYPE: PRT
<213> ORGANISM: BK virus

<400> SEQUENCE: 140

Gly Gly Val Glu Val Leu Glu Val Lys Thr Gly Val Asp Ala Ile Thr
1               5                   10                  15
```

```
Glu Val Glu Cys Phe Leu Asn Pro Glu Met Gly Asp Pro Asp Asp Asn
            20                  25                  30

Leu Arg Gly Tyr Ser Leu Lys Leu Thr Ala Glu Asn Ala Phe Asp Ser
        35                  40                  45

Asp Ser Pro Asp Lys Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Val Gln Gly Ser Asn Phe His Phe Phe Ala Val Gly Gly Asp
        115                 120                 125

Pro Leu Glu Met Gln Gly Val Leu Met Asn Tyr Arg Thr Arg Tyr Pro
    130                 135                 140


<210> SEQ ID NO 141
<211> LENGTH: 144
<212> TYPE: PRT
<213> ORGANISM: BK virus

<400> SEQUENCE: 141

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 142
<211> LENGTH: 144
<212> TYPE: PRT
<213> ORGANISM: BK virus

<400> SEQUENCE: 142

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60
```

```
Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Ser Tyr Pro
    130                 135                 140


<210> SEQ ID NO 143
<211> LENGTH: 144
<212> TYPE: PRT
<213> ORGANISM: BK virus

<400> SEQUENCE: 143

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Asp Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 144
<211> LENGTH: 144
<212> TYPE: PRT
<213> ORGANISM: BK virus

<400> SEQUENCE: 144

Gly Gly Val Glu Val Leu Glu Val Lys Thr Gly Leu Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110
```

```
Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Arg Tyr Pro
    130                 135                 140


<210> SEQ ID NO 145
<211> LENGTH: 144
<212> TYPE: PRT
<213> ORGANISM: BK virus

<400> SEQUENCE: 145

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 146
<211> LENGTH: 144
<212> TYPE: PRT
<213> ORGANISM: BK virus

<400> SEQUENCE: 146

Gly Gly Val Glu Val Leu Glu Val Lys Thr Gly Leu Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 147
```

<211> LENGTH: 144
<212> TYPE: PRT
<213> ORGANISM: BK virus

<400> SEQUENCE: 147

Gly Gly Val Glu Val Leu Glu Val Lys Thr Gly Leu Asp Ala Ile Thr
1 5 10 15

Glu Val Glu Cys Phe Leu Asn Pro Glu Met Gly Asp Pro Asp Glu Asn
20 25 30

Leu Arg Gly Phe Ser Leu Lys Leu Ser Ala Glu Asn Asp Phe Ser Ser
35 40 45

Asp Ser Pro Glu Arg Lys Met Leu Pro Cys Tyr Ser Thr Ala Arg Ile
50 55 60

Pro Leu Pro Asn Leu Asn Glu Asp Leu Thr Cys Gly Asn Leu Leu Met
65 70 75 80

Trp Glu Ala Val Thr Val Gln Thr Glu Val Ile Gly Ile Thr Ser Met
85 90 95

Leu Asn Leu His Ala Gly Ser Gln Lys Val His Glu His Gly Gly Gly
100 105 110

Lys Pro Ile Gln Gly Ser Asn Phe His Phe Phe Ala Val Gly Gly Asp
115 120 125

Pro Leu Glu Met Gln Gly Val Leu Met Asn Tyr Arg Thr Asn Tyr Pro
130 135 140

<210> SEQ ID NO 148
<211> LENGTH: 144
<212> TYPE: PRT
<213> ORGANISM: BK virus

<400> SEQUENCE: 148

Gly Gly Val Glu Val Leu Glu Val Lys Thr Gly Val Asp Ala Ile Thr
1 5 10 15

Glu Val Glu Cys Phe Leu Asn Pro Glu Met Gly Asp Pro Asp Glu Asn
20 25 30

Leu Arg Gly Phe Ser Leu Lys Leu Ser Ala Glu Asn Asp Phe Ser Ser
35 40 45

Asp Ser Pro Glu Arg Lys Met Leu Pro Cys Tyr Ser Thr Ala Arg Ile
50 55 60

Pro Leu Pro Asn Leu Asn Glu Asp Leu Thr Cys Gly Asn Leu Leu Met
65 70 75 80

Trp Glu Ala Val Thr Val Gln Thr Glu Val Ile Gly Ile Thr Ser Met
85 90 95

Leu Asn Leu His Ala Gly Ser Gln Lys Val His Glu His Gly Gly Gly
100 105 110

Lys Pro Ile Gln Gly Ser Asn Phe His Phe Phe Ala Val Gly Gly Asp
115 120 125

Pro Leu Glu Met Gln Gly Val Leu Leu Asn Tyr Arg Thr Asn Tyr Pro
130 135 140

<210> SEQ ID NO 149
<211> LENGTH: 144
<212> TYPE: PRT
<213> ORGANISM: BK virus

<400> SEQUENCE: 149

Gly Gly Val Glu Val Leu Glu Val Lys Thr Gly Val Asp Ala Ile Thr
1 5 10 15

```
Glu Val Glu Cys Phe Leu Asn Pro Glu Met Gly Asp Pro Asp Ser Asp
            20                  25                  30

Leu Arg Gly Tyr Ser Leu Arg Leu Thr Ala Glu Thr Ala Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 150
<211> LENGTH: 144
<212> TYPE: PRT
<213> ORGANISM: BK virus

<400> SEQUENCE: 150

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 151
<211> LENGTH: 144
<212> TYPE: PRT
<213> ORGANISM: BK virus

<400> SEQUENCE: 151

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Tyr Ser Leu Arg Leu Thr Ala Glu Thr Ala Phe Asp Ser
        35                  40                  45

Asp Ser Pro Asn Arg Lys Met Leu Pro Cys Tyr Ser Thr Ala Arg Ile
    50                  55                  60
```

```
Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Lys Met Pro Gly Val Leu Met Asn Tyr Arg Thr Lys Tyr Pro
    130                 135                 140


<210> SEQ ID NO 152
<211> LENGTH: 144
<212> TYPE: PRT
<213> ORGANISM: BK virus

<400> SEQUENCE: 152

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Asn Asp
            20                  25                  30

Leu Arg Gly Phe Ser Leu Arg Leu Thr Ala Glu Asn Ala Phe Glu Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Leu His Ala Gly Ser Gln Lys Val His Glu Asn Gly Gly Gly
            100                 105                 110

Lys Pro Ile Gln Gly Ser Asn Phe His Phe Phe Ala Val Gly Gly Asp
        115                 120                 125

Pro Leu Glu Met Gln Gly Val Leu Met Asn Tyr Arg Thr Ser Tyr Pro
    130                 135                 140


<210> SEQ ID NO 153
<211> LENGTH: 144
<212> TYPE: PRT
<213> ORGANISM: BK virus

<400> SEQUENCE: 153

Gly Gly Val Glu Val Leu Glu Val Lys Thr Gly Leu Asp Ser Ile Thr
1               5                   10                  15

Glu Val Glu Cys Phe Leu Asn Pro Glu Met Gly Asp Pro Glu Glu Asn
            20                  25                  30

Leu Arg Gly Phe Ser Leu Arg Leu Ser Val Ala Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110
```

```
Lys Pro Ile Gln Gly Ser Asn Phe His Phe Phe Ala Val Gly Gly Asp
        115                 120                 125

Pro Leu Glu Met Gln Gly Val Leu Met Asn Tyr Lys Thr Lys Tyr Pro
    130                 135                 140


<210> SEQ ID NO 154
<211> LENGTH: 144
<212> TYPE: PRT
<213> ORGANISM: BK virus

<400> SEQUENCE: 154

Gly Gly Val Glu Val Leu Glu Val Lys Asn Gly Val Asp Ser Ile Thr
1               5                   10                  15

Glu Val Glu Ile Phe Leu Asn Pro Glu Met Gly Asp Pro Asp Asn Asp
            20                  25                  30

Leu Arg Gly Tyr Ser Leu Lys Ser Ile Ser Lys Asn Asp Phe Glu Ser
        35                  40                  45

Asp Ser Pro Asp Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Lys Thr Glu Val Ile Gly Ile Thr Ser Met
                85                  90                  95

Leu Asn Phe His Ala Gly Ser Gln Lys Ala His Glu Asn Gly Gly Gly
            100                 105                 110

Lys Pro Ile Gln Gly Ser Ser Phe His Phe Phe Ala Val Gly Gly Asp
        115                 120                 125

Pro Leu Glu Met Gln Gly Val Leu Met Asn Tyr Arg Thr Lys Tyr Pro
    130                 135                 140


<210> SEQ ID NO 155
<211> LENGTH: 144
<212> TYPE: PRT
<213> ORGANISM: BK virus

<400> SEQUENCE: 155

Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Asp Glu Asn
            20                  25                  30

Leu Arg Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Ser Ser Met
                85                  90                  95

Leu Asn Leu His Ala Gly Ser Gln Lys Glu His Glu His Gly Gly Gly
            100                 105                 110

Lys Pro Ile Gln Gly Ser His Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140


<210> SEQ ID NO 156
<211> LENGTH: 144
```

-continued

<212> TYPE: PRT
<213> ORGANISM: BK virus

<400> SEQUENCE: 156

```
Gly Gly Val Glu Val Leu Glu Val Lys Thr Gly Val Asp Ala Ile Thr
1               5                   10                  15

Glu Val Glu Cys Phe Leu Asn Pro Glu Met Gly Asp Pro Glu Glu Lys
            20                  25                  30

Leu Asn Gly Phe Ser Leu Lys Leu Ser Ala Glu Asn Asp Phe Ser Ser
        35                  40                  45

Asp Ser Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Glu His Glu His Gly Gly Gly
            100                 105                 110

Lys Pro Ile Gln Gly Ser His Phe His Phe Phe Ala Val Gly Gly Asp
        115                 120                 125

Pro Leu Glu Met Gln Gly Val Leu Leu Asn Tyr Arg Thr Lys Tyr Pro
    130                 135                 140
```

<210> SEQ ID NO 157
<211> LENGTH: 144
<212> TYPE: PRT
<213> ORGANISM: BK virus

<400> SEQUENCE: 157

```
Gly Gly Val Glu Val Leu Glu Val Lys Thr Gly Val Asp Ser Ile Thr
1               5                   10                  15

Glu Val Glu Cys Phe Leu Asn Pro Glu Met Gly Asp Pro Asp Glu Ser
            20                  25                  30

Phe Arg Gly Phe Ser Leu Lys Leu Ser Ala Glu Asn Asp Ile Ser Ser
        35                  40                  45

Asp Asn Pro Glu Arg Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Ser Ser Met
                85                  90                  95

Leu Asn Leu His Ala Gly Ser Gln Lys Val His Glu His Gly Gly Gly
            100                 105                 110

Lys Pro Ile Gln Gly Ser Asn Phe His Phe Phe Ala Val Gly Gly Asp
        115                 120                 125

Pro Leu Lys Met Gln Gly Val Leu Leu Asn Tyr Arg Thr Ser Tyr Pro
    130                 135                 140
```

<210> SEQ ID NO 158
<211> LENGTH: 144
<212> TYPE: PRT
<213> ORGANISM: BK virus

<400> SEQUENCE: 158

```
Gly Gly Val Glu Val Leu Glu Val Lys Thr Gly Val Asp Ala Ile Thr
1               5                   10                  15

Glu Val Glu Ser Phe Leu Asn Pro Glu Met Gly Asp Pro Glu Glu Thr
```

-continued

```
            20                  25                  30

Phe Arg Gly Phe Ser Leu Lys Gln Ser Ser Glu Lys Asp Ile Ser Asn
        35                  40                  45

Asp Ser Pro Lys Lys Lys Met Leu Pro Cys Tyr Ser Thr Ala Arg Ile
    50                  55                  60

Pro Leu Pro Asn Leu Asn Glu Asp Leu Thr Cys Gly Asn Leu Leu Met
65                  70                  75                  80

Trp Glu Ala Val Thr Val Gln Thr Glu Val Ile Gly Ile Thr Ser Met
                85                  90                  95

Leu Asn Leu His Ala Gly Ser Gln Lys Val His Glu His Gly Gly Gly
            100                 105                 110

Lys Pro Ile Gln Gly Ser His Val His Phe Phe Ala Val Gly Gly Asp
        115                 120                 125

Pro Leu Lys Met Gln Gly Val Val Met Asn Tyr Lys Thr Lys Tyr Pro
    130                 135                 140
```

METHODS AND COMPOSITIONS FOR INHIBITING POLYOMAVIRUS-ASSOCIATED PATHOLOGY

CROSS REFERENCE TO RELATED APPLICATIONS

This is the U.S. National Stage of International Application No. PCT/US2012/047069, filed Jul. 17, 2012, which was published in English under PCT Article 21(2), which in turn claims the benefit of U.S. Provisional Application No. 61/508,897, filed Jul. 18, 2011, which is incorporated by reference herein in its entirety.

FIELD

This disclosure relates to the field of immunology, more specifically to methods and compositions for producing an immune response to polyomavirus, particularly BK polyomavirus.

BACKGROUND

The process of organ transplantation has been revolutionized since the first successful kidney transplant in identical twins more than five decades ago (Harrison et al., *Surg. Forum* 6:432-436, 1956; Merrill et al., *J. Am. Med. Assoc.* 160:277-282, 1956). Since then, the use of immunosuppressants, such as cyclosporine, have improved the outcome of transplants (Calne, *Mt. Sinai J. Med.* 54:465-466, 1987), but the process is still fraught with many challenges, such as the management of chronic and acute rejection, nephrotoxicity from immunosuppressant and antiviral drugs, and avoiding reactivated (or novel) infectious agents that could threaten the graft. To balance these needs, clinical guidelines on the management of kidney transplant (Kasiske et al., *Am. J. Transpl.* 9:S1-S155, 2009) generally suggest the use of an immunosuppressant and an anti-proliferative agent in the initial stages of the process, followed by a lowering of dose of immunosuppressants if there is no acute rejection. However, careful monitoring of allograft function is crucial; and tests to detect increase in proteinuria, elevated serum creatinine levels, and detection of viral nucleic acids in plasma are also recommended.

One of the problems that threatens kidney allograft survival is the development of polyomavirus-associated nephropathy (PVAN) (Purighalla et al., *Am. J. Kidney Dis.* 26:671-673, 1995; also known as BKV associated nephropathy (BKVN)). Left untreated, PVAN can lead to a loss of the allograft, but early diagnosis, monitoring and intervention can prevent it. In kidney transplant recipients, current estimates of PVAN are about 1-10% (Ramos et al., *Clin. Transpl.* 2002:143-153; Hirsch et al., *Transplantation* 79:1277-1286, 2005), and graft losses range from 10-100% (Hirsch and Steiger, *Lancet Inf. Dis.* 3:611-623, 2003) depending on the drug regimen, monitoring, and interventions performed. Polyomavirus-associated pathologies such as PVAN or progressive multifocal leukoencephalopathy (PML) also cause significant morbidity or even mortality in other patients receiving immunosuppressive therapy (for example, for auto-immune disorders).

SUMMARY

Disclosed herein are methods of eliciting an immune response against a polyomavirus (for example, BKV serotype I (BKV-I), BKV serotype II (BKV-II), BKV serotype III (BKV-III), and/or BKV serotype IV (BKV-IV)) and methods of treating or inhibiting polyomavirus-associated pathology (such as PVAN, BKV-associated hemorrhagic cystitis, or JC virus-associated PML). Further disclosed are immunogenic compositions of use in the disclosed methods. In some embodiments, the immunogenic composition includes at least one capsid polypeptide (or a nucleic acid encoding such polypeptides) from two or more BKV serotypes (e.g., a multivalent immunogenic composition).

Also disclosed are methods of selecting a transplant donor and/or transplant recipient (for example a renal transplant donor or recipient) including detecting whether the prospective donor and/or recipient has BKV serotype-specific (such as BKV-IV-specific) neutralizing antibodies.

The foregoing and other features of the disclosure will become more apparent from the following detailed description, which proceeds with reference to the accompanying figures.

Figure 5:
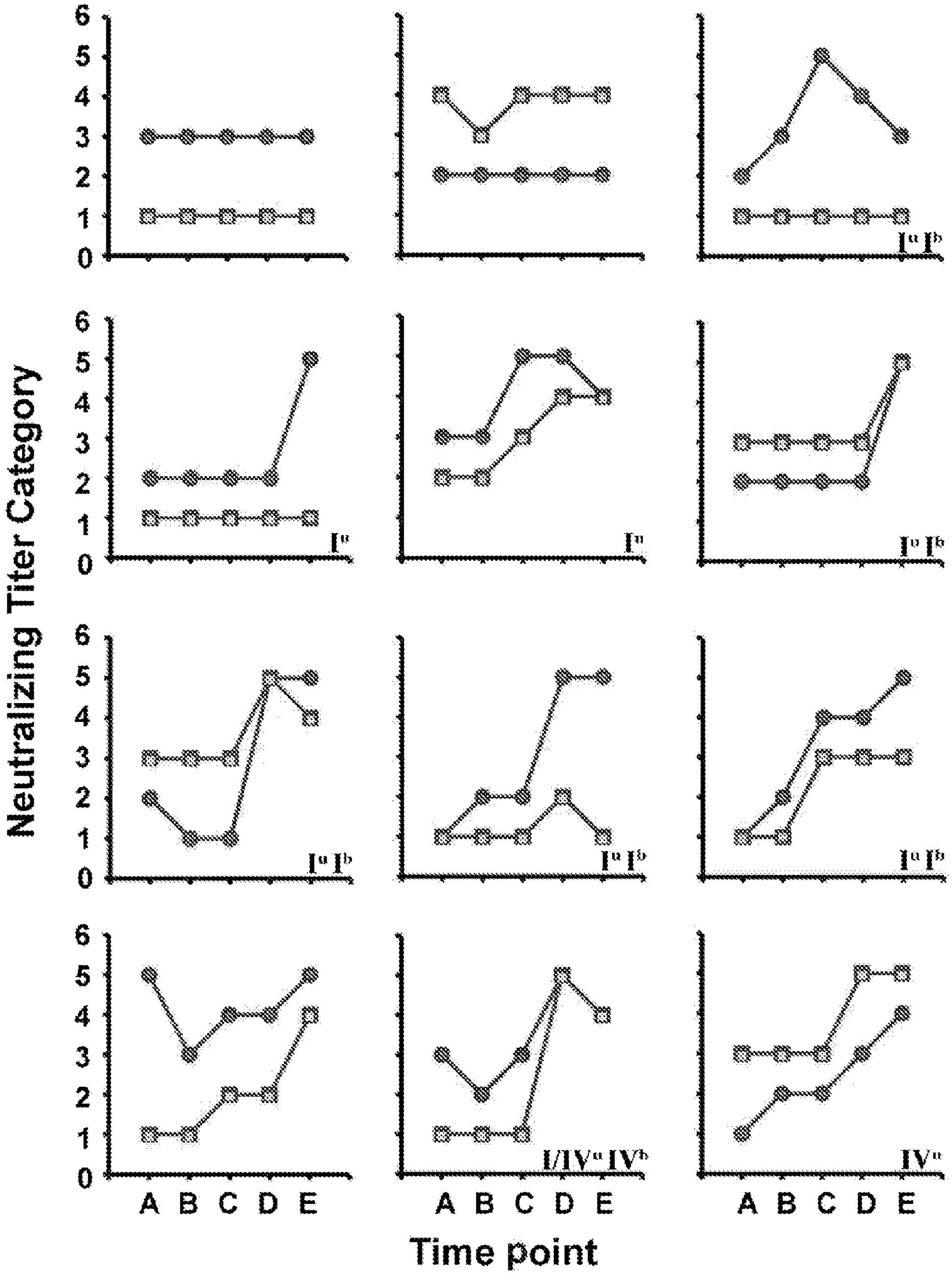
FIG. 5 is a series of graphs showing BKV-I and BKV-IV serological patterns in sera from individual kidney transplant recipients. Sera from kidney transplant recipients were titered for the presence of BKV-I (circles) or BKV-IV (squares) type-specific neutralizing titers (y axis). The neutralizing titer categories shown on the y axis are defined as: 1)<95% neutralization at a serum dilution of 1:100; 2)≥95% neutralization at 1:100; 3)≥95% neutralization at 1:500; 4)≥95% neutralization at 1:5000; and 5)≥95% neutralization at 1:50,000. Sera were collected at five different time points (x axis) spanning roughly 1, 4, 12, 26, and 52 weeks post-transplantation, designated A-E. In each panel, the notations in the bottom right corner represent the BKV genotype (I or IV) observed in the patient's urine (superscript u) or blood (superscript b). The subject denoted I/IV$^u$ showed urinary shedding of BKV-I at week 5 and urinary shedding of BKV-IV at week 16. The patterns of 12 representative patients are shown.
Figure 6:
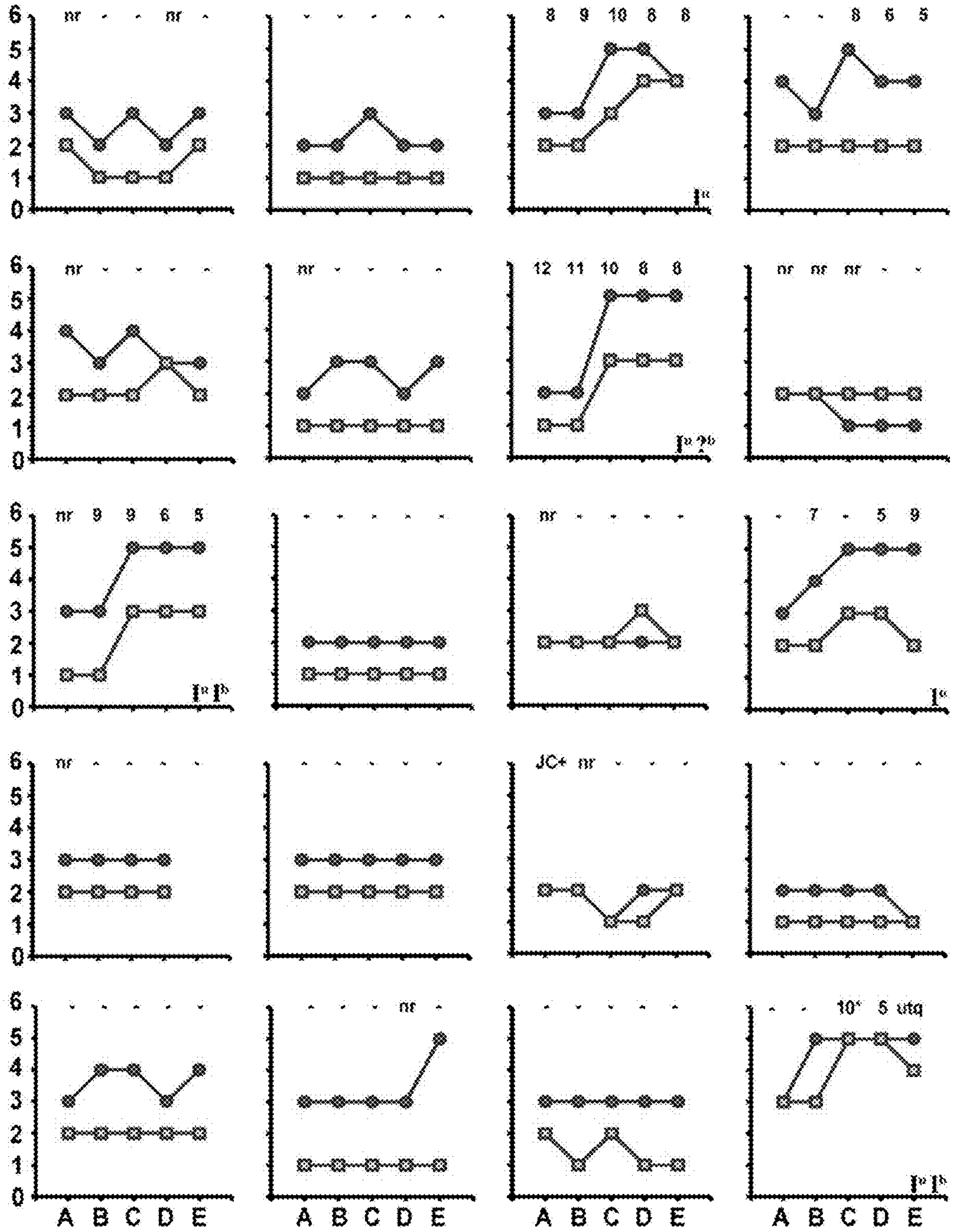
Figure 6:
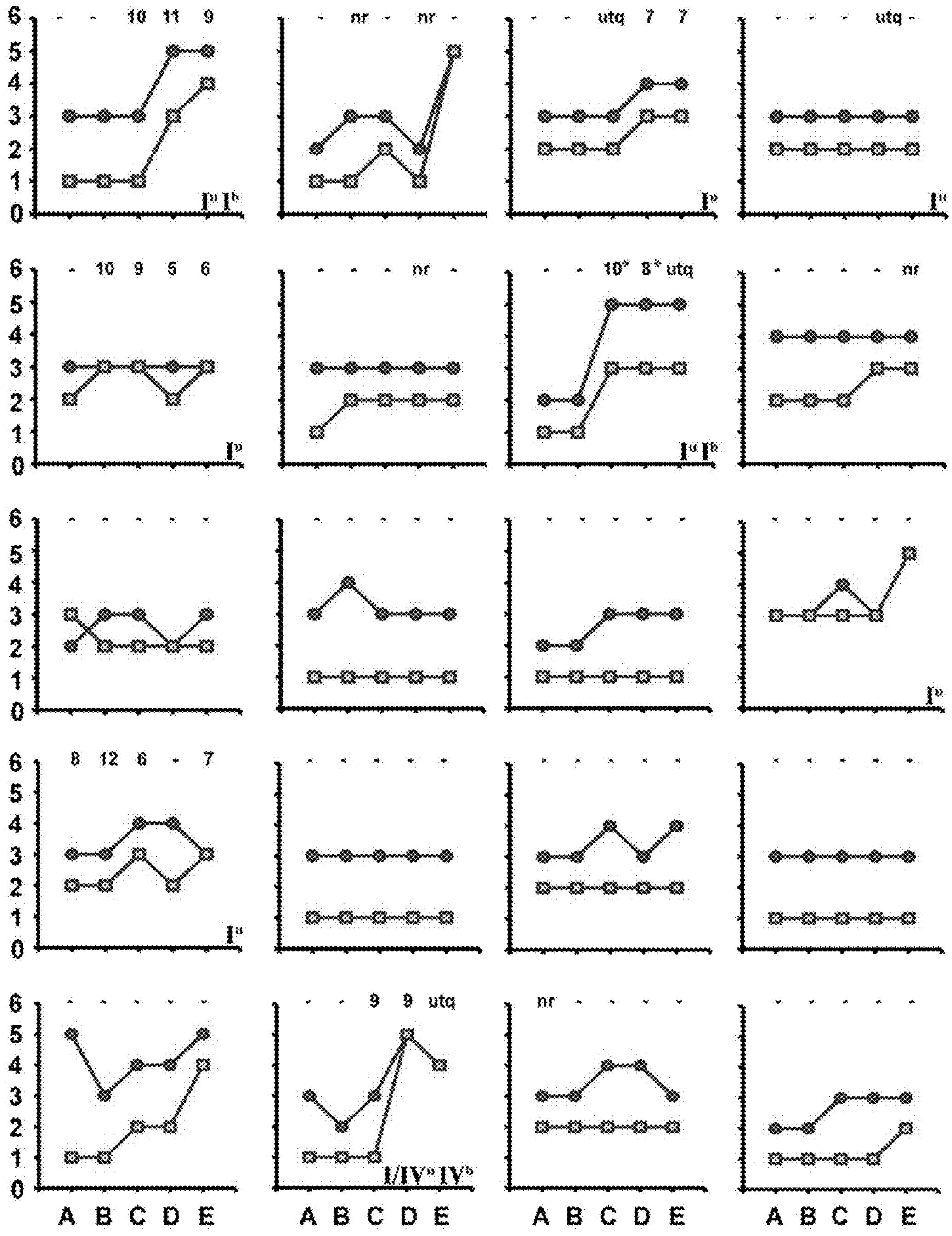
Figure 6:
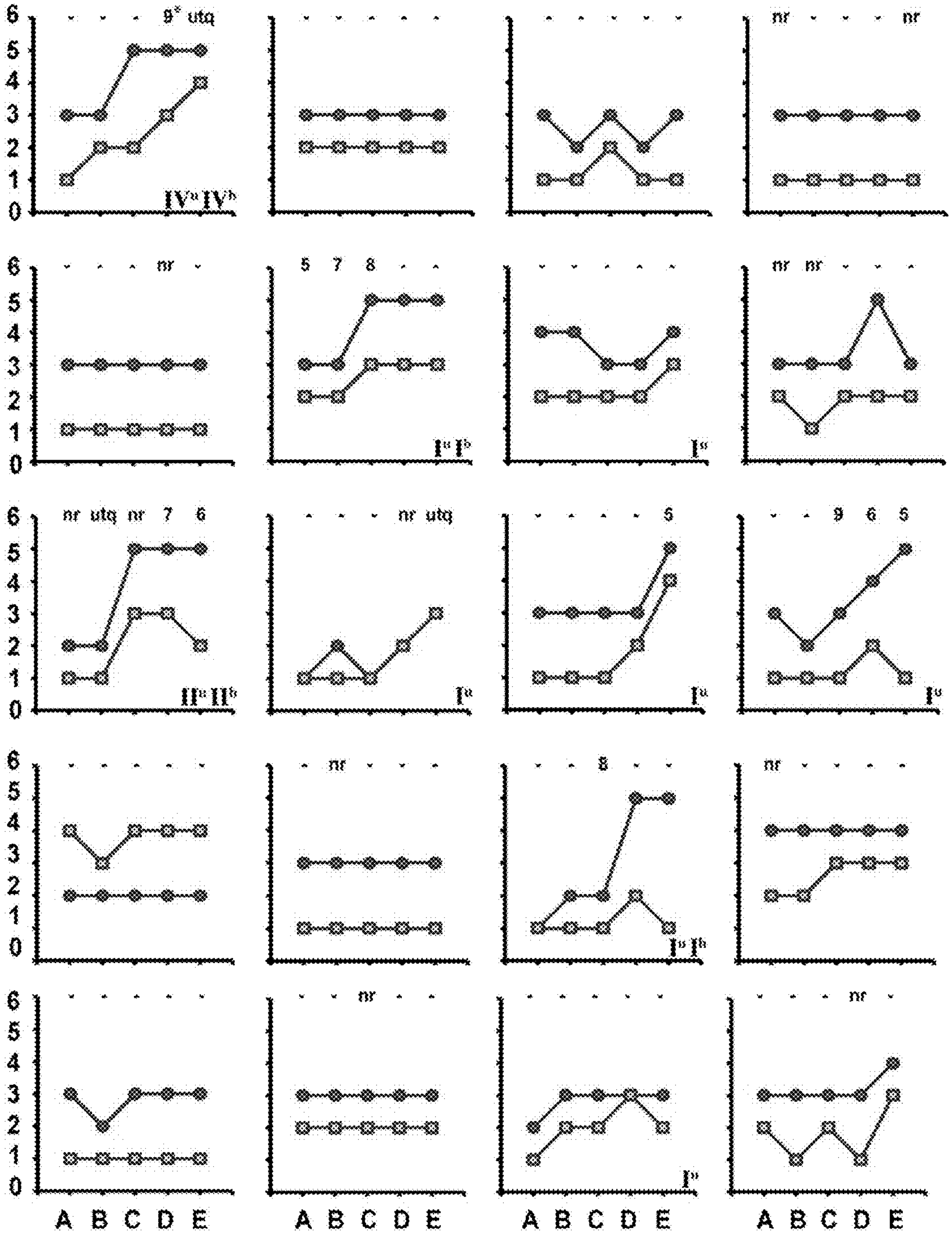
Figure 6:
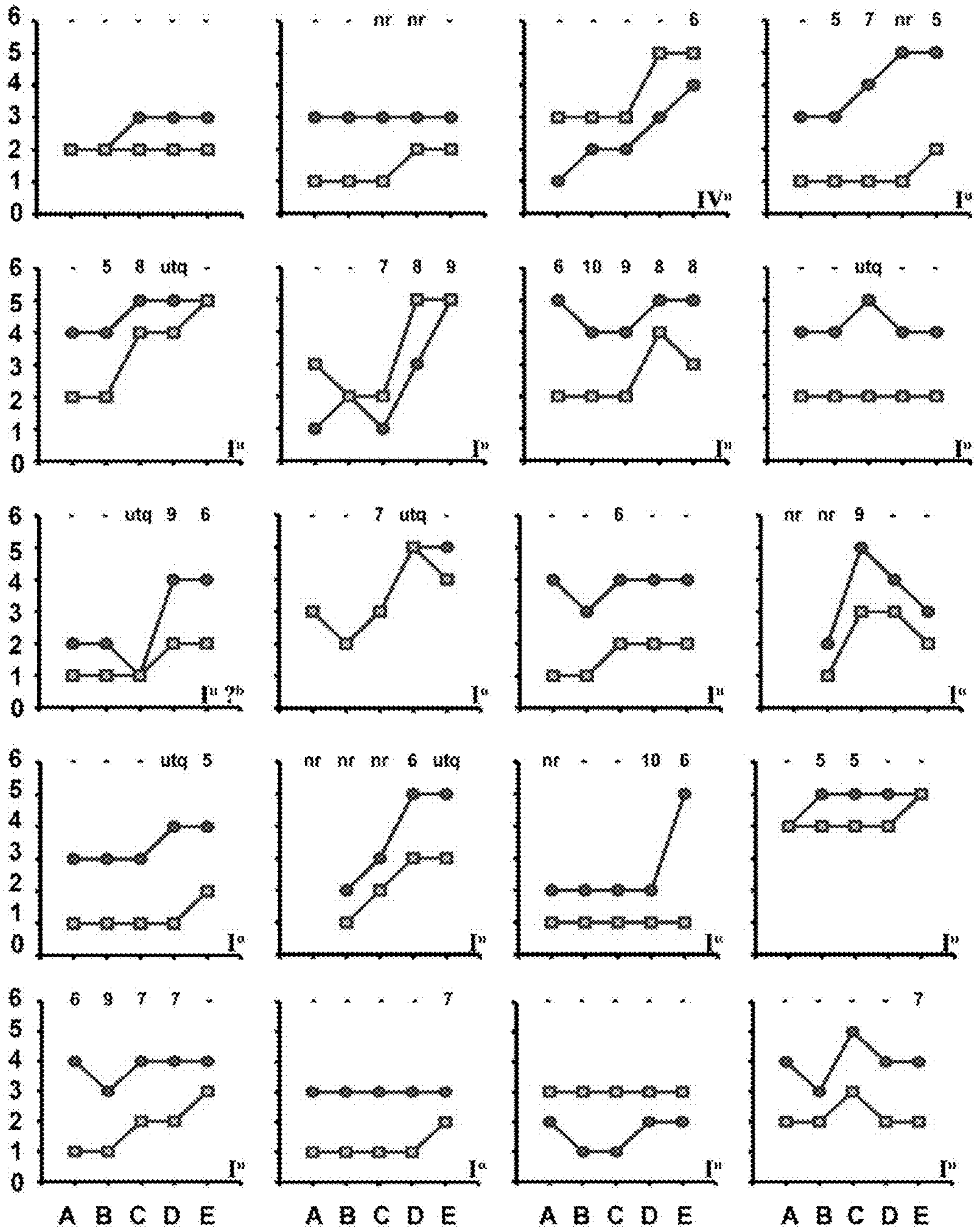
Figure 6:
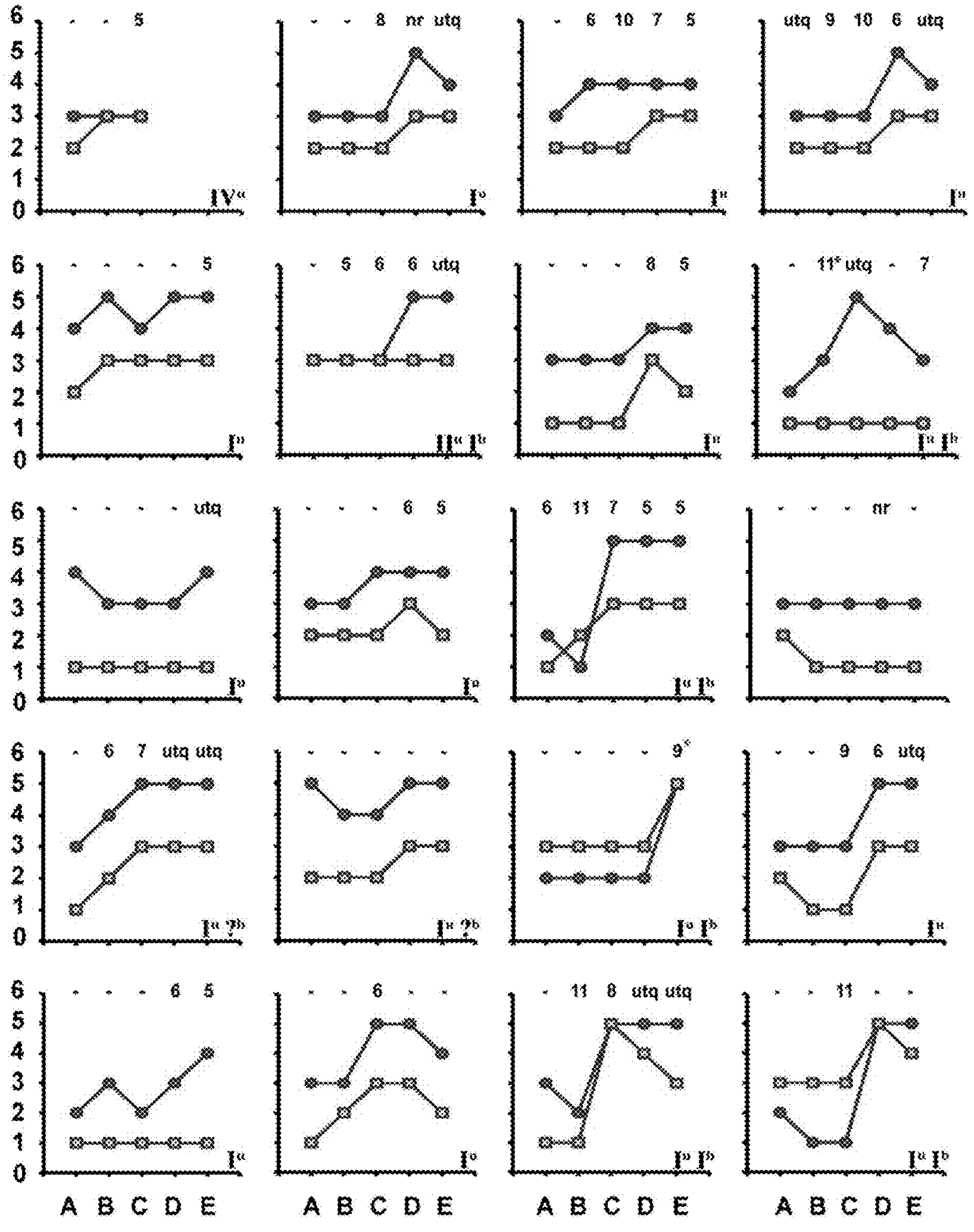
Figure 6:
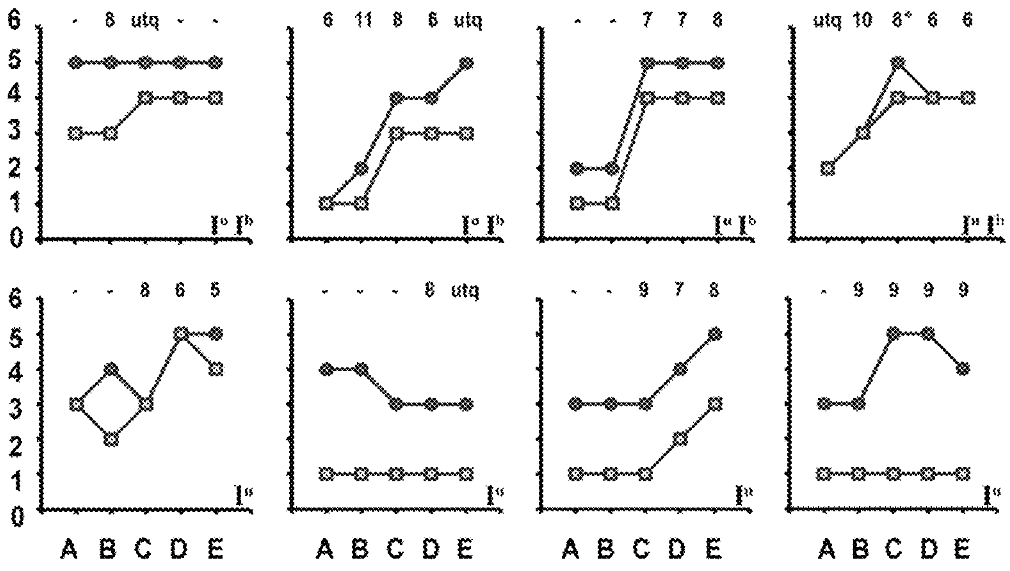

FIG. 6 is a series of graphs showing BKV-I and BKV-IV serological profiles in all 108 kidney transplant patients analyzed. Neutralizing titer categories (y-axis) and time points (x-axis) are as described for FIG. 5. The numbers at the top of each graph denote quantitation of BKV viruria (log 10 BKV DNA copies per ml) at each time point. Dashes indicate that BKV DNA was not detected in the urine. The symbol "nr" indicates no results for the time point. The symbol "utq" indicates that the BKV viruria signal was too low for accurate quantitation. Asterisks mark time points at which BKV viremia was quantitated. The symbol JC+ indicates that JC virus DNA was detected.

Figure 7:
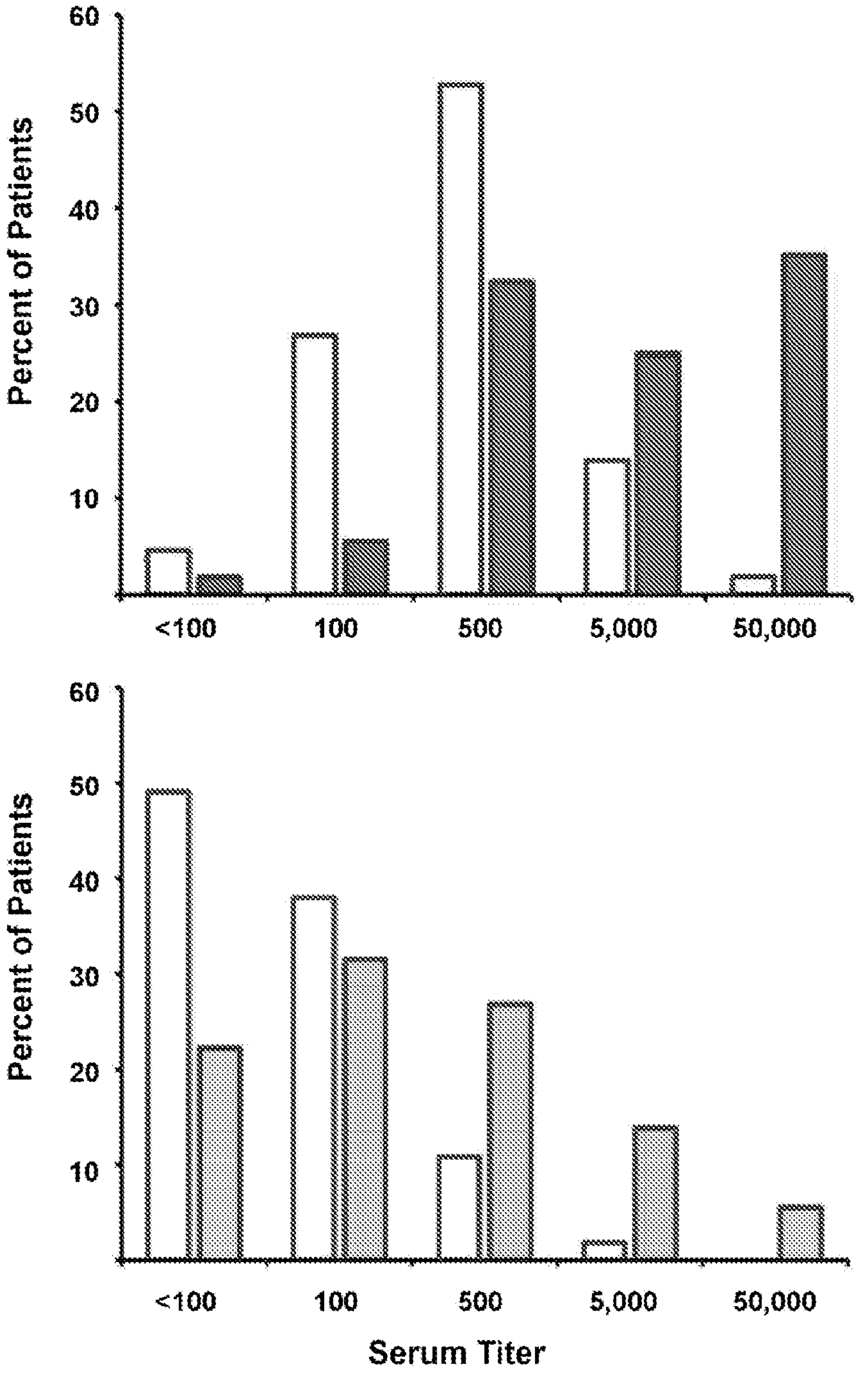

FIG. 7 is a pair of graphs showing BKV-I and BKV-IV neutralizing titers in kidney transplant recipients at study entry and exit. Sera from 108 kidney transplant recipients were titered for the presence of BKV-I (top panel) or BKV-IV (bottom panel) type-specific neutralizing antibodies. The percentages of patients at a particular titer cut-off at study entry (one week after transplantation) are depicted as open bars, while the percentages of patients at a particular titer cut-off at study exit (one year post-transplantation) are depicted as filled bars.

Figure 8:
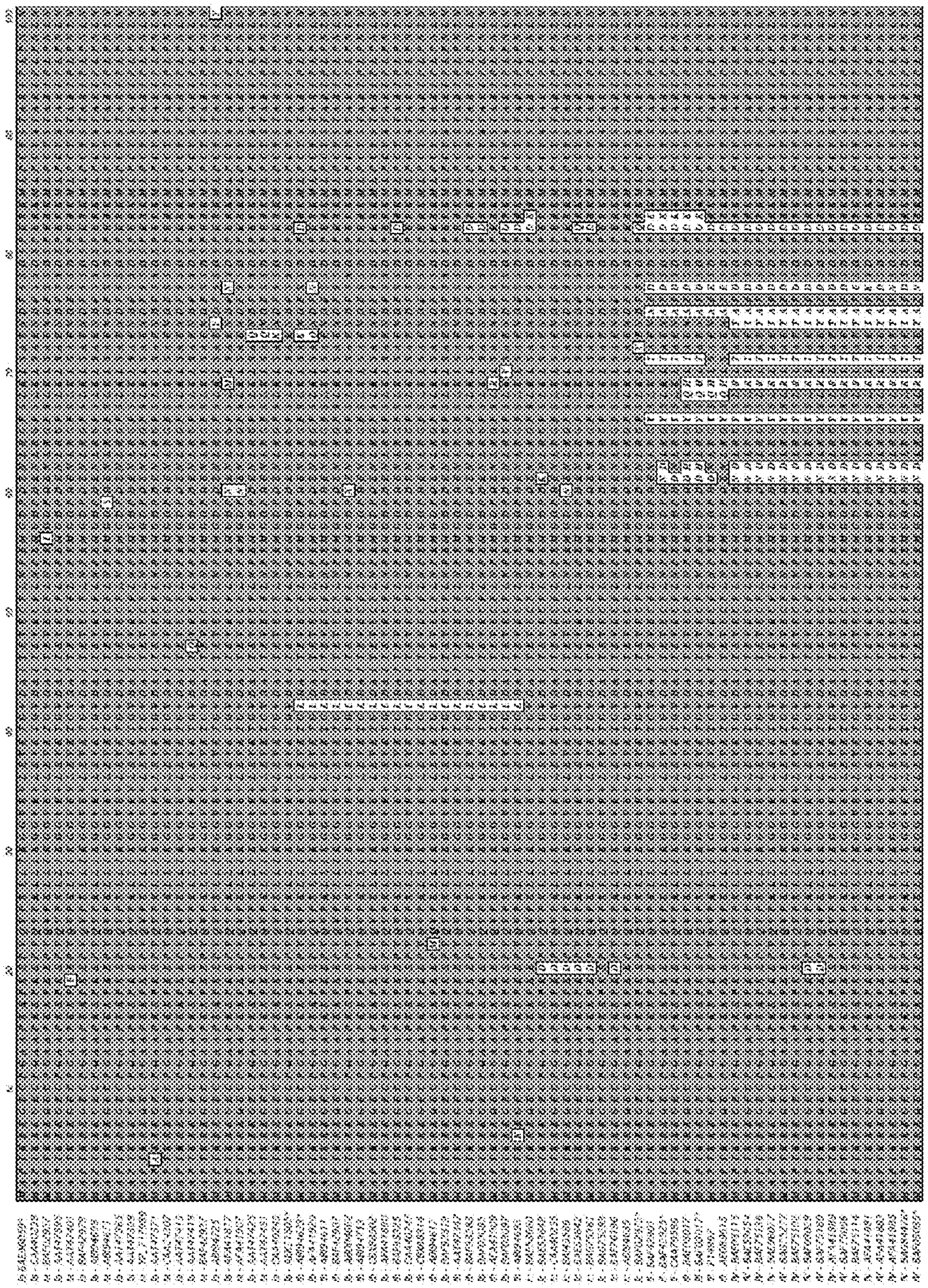
Figure 8:
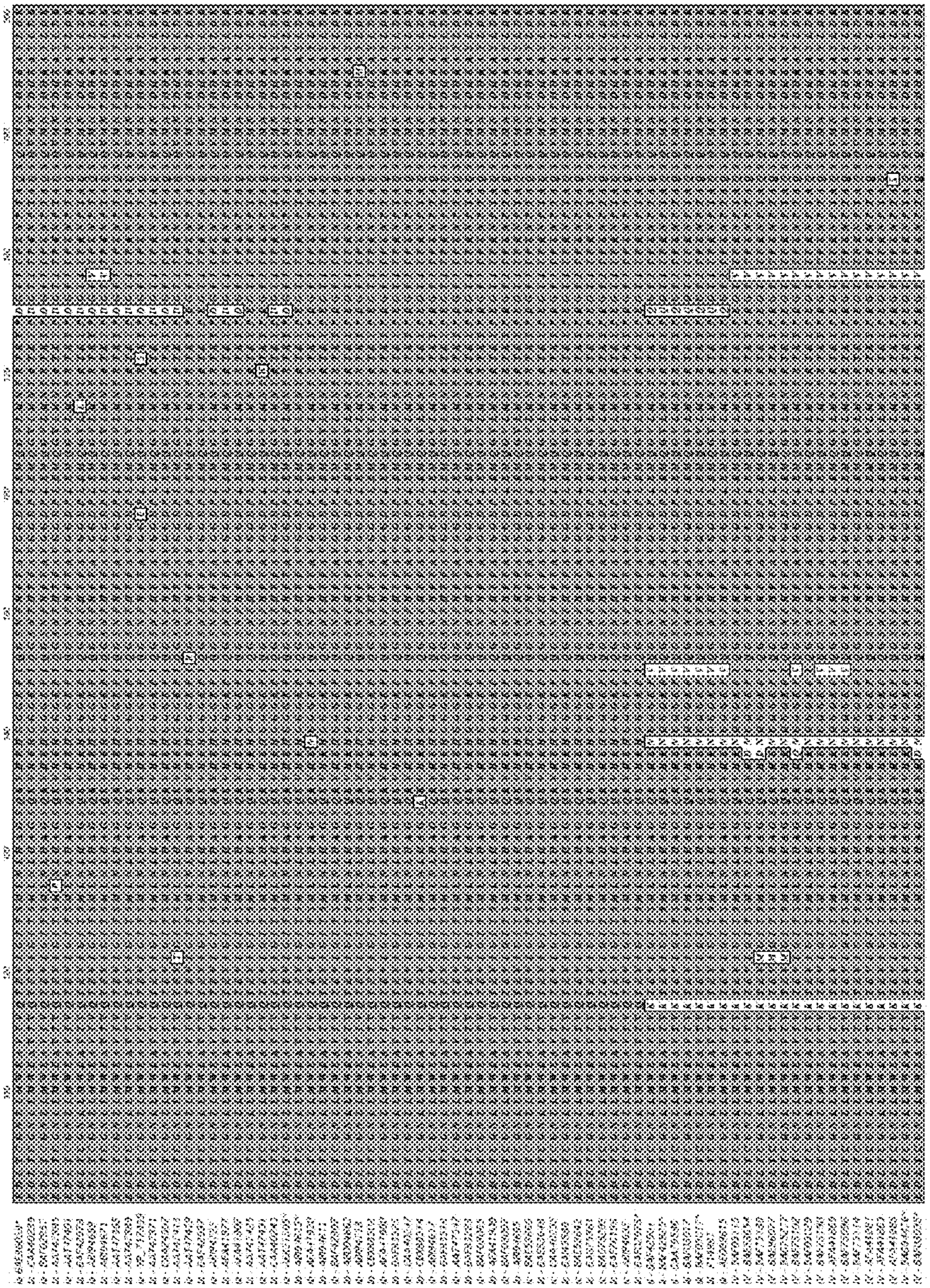
Figure 8:
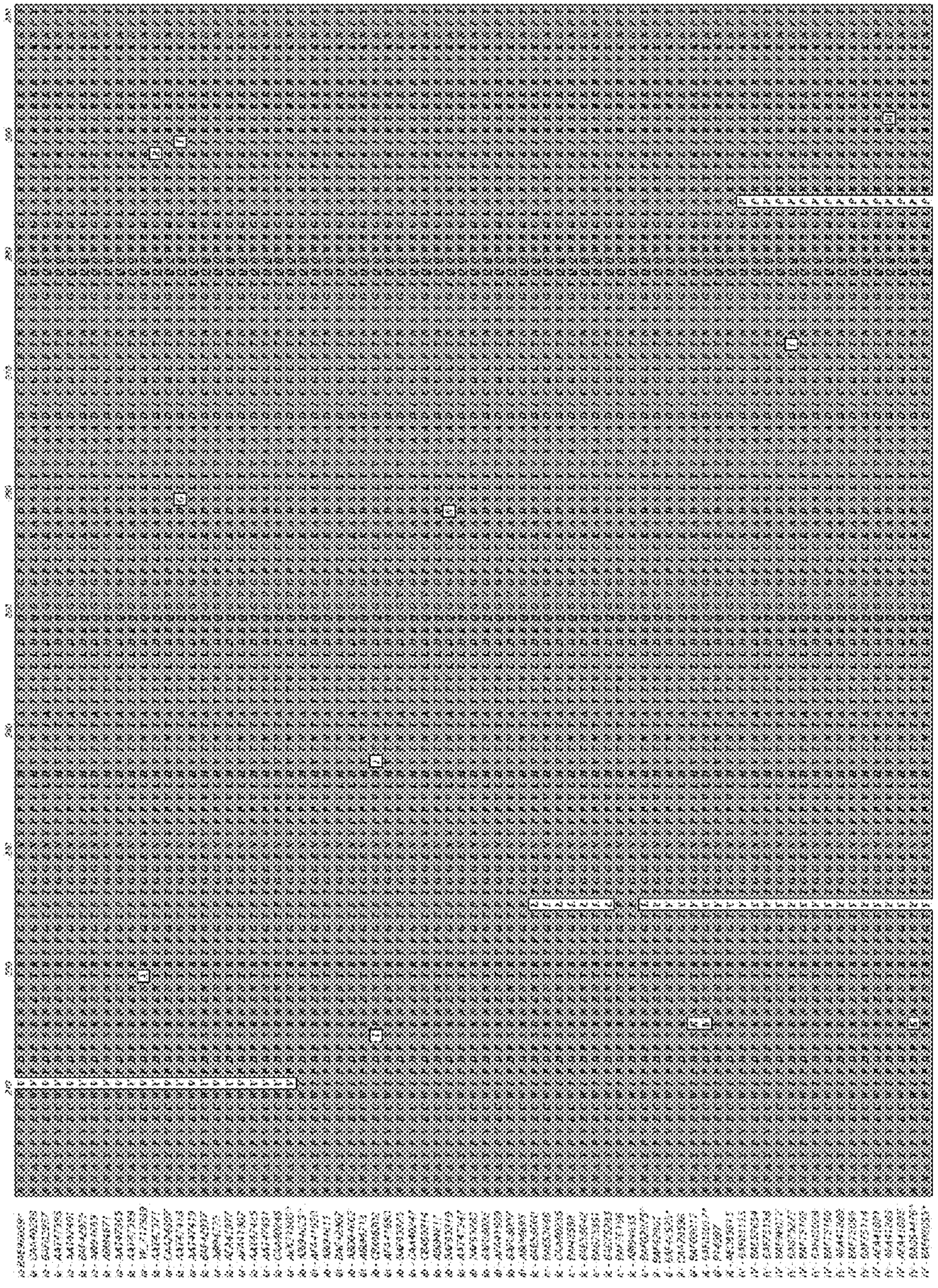
Figure 8:
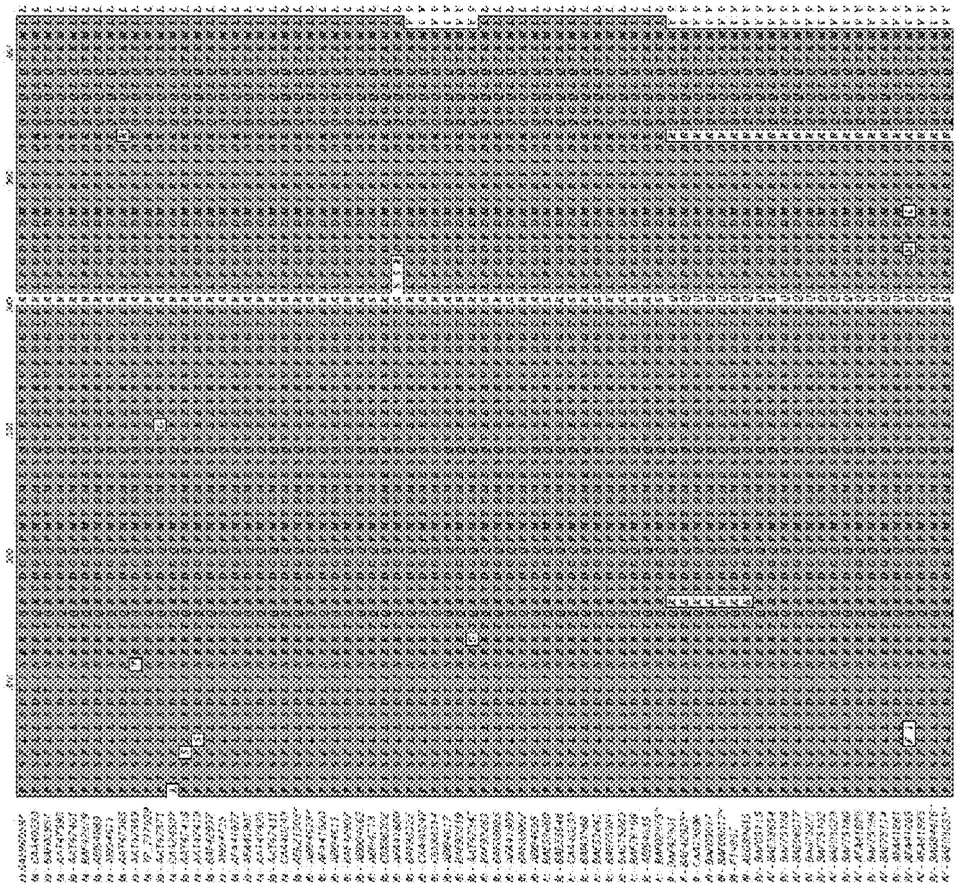

FIG. 8 is a sequence alignment of BKV VP1 polypeptides. Because it is not possible to distinguish between Ia and Ib1 subtypes based on VP1 amino acid sequences, BKV-Ia indicates genotypes Ia/Ib1 and BKV-Ib indicates genotype Ib2. It is also not possible to distinguish between BKV-IV subtypes based on VP1 amino acid sequences. Therefore, BKV-IV indicates genotypes IV-b1/IV-c2. Amino acids that are completely conserved among all BKV types are shaded. Sequence identifiers for the amino acid sequences are provided in Table 5 (below).

Figure 9:
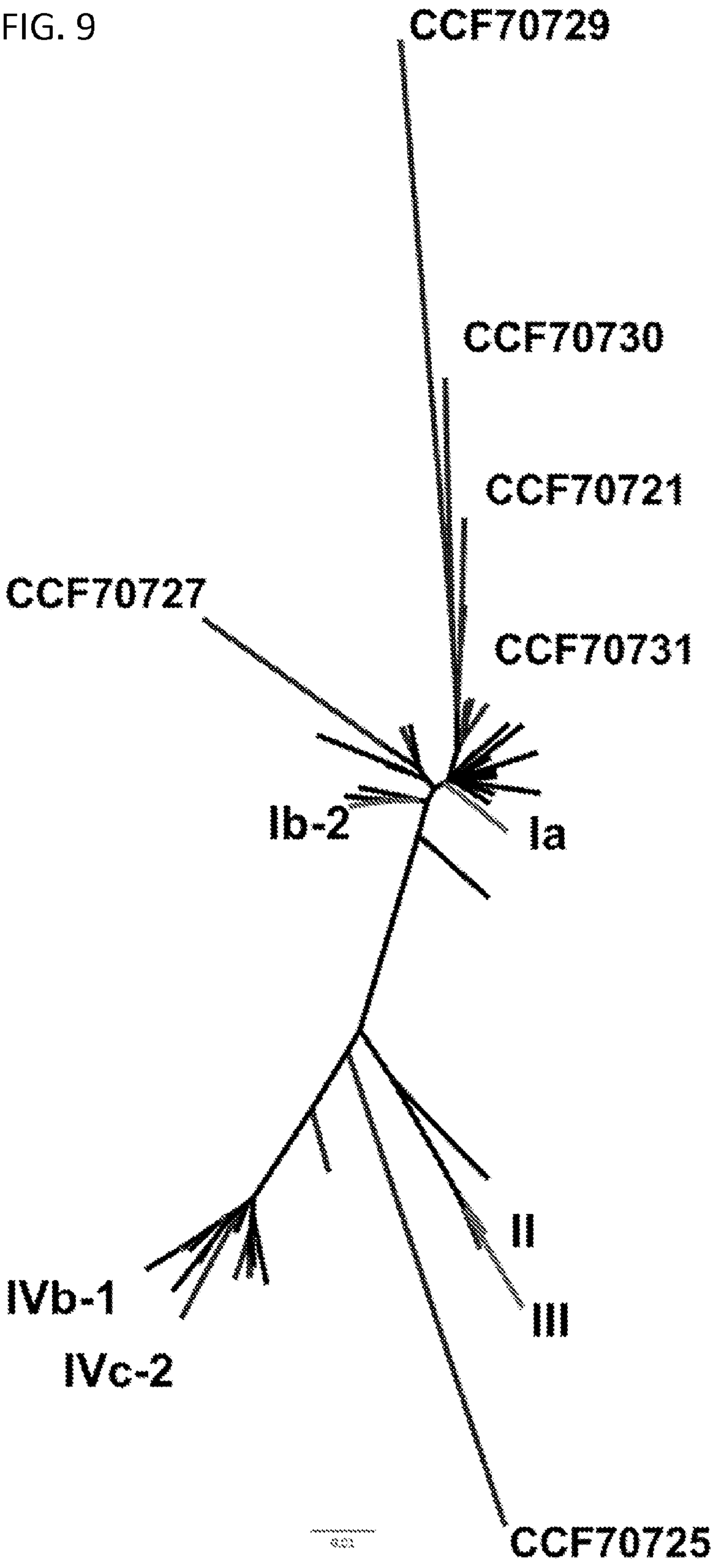
Figure 10:
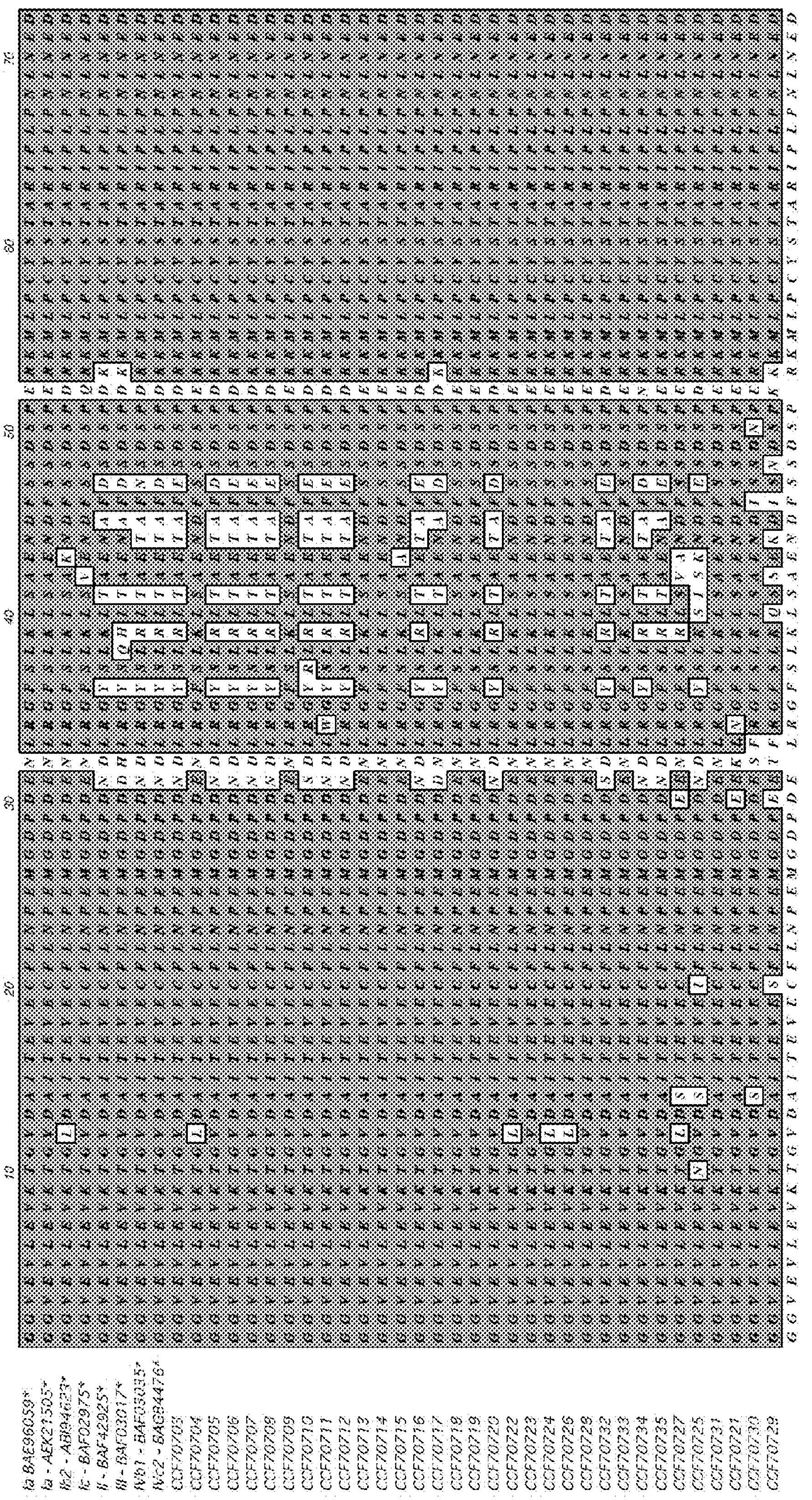
Figure 10:
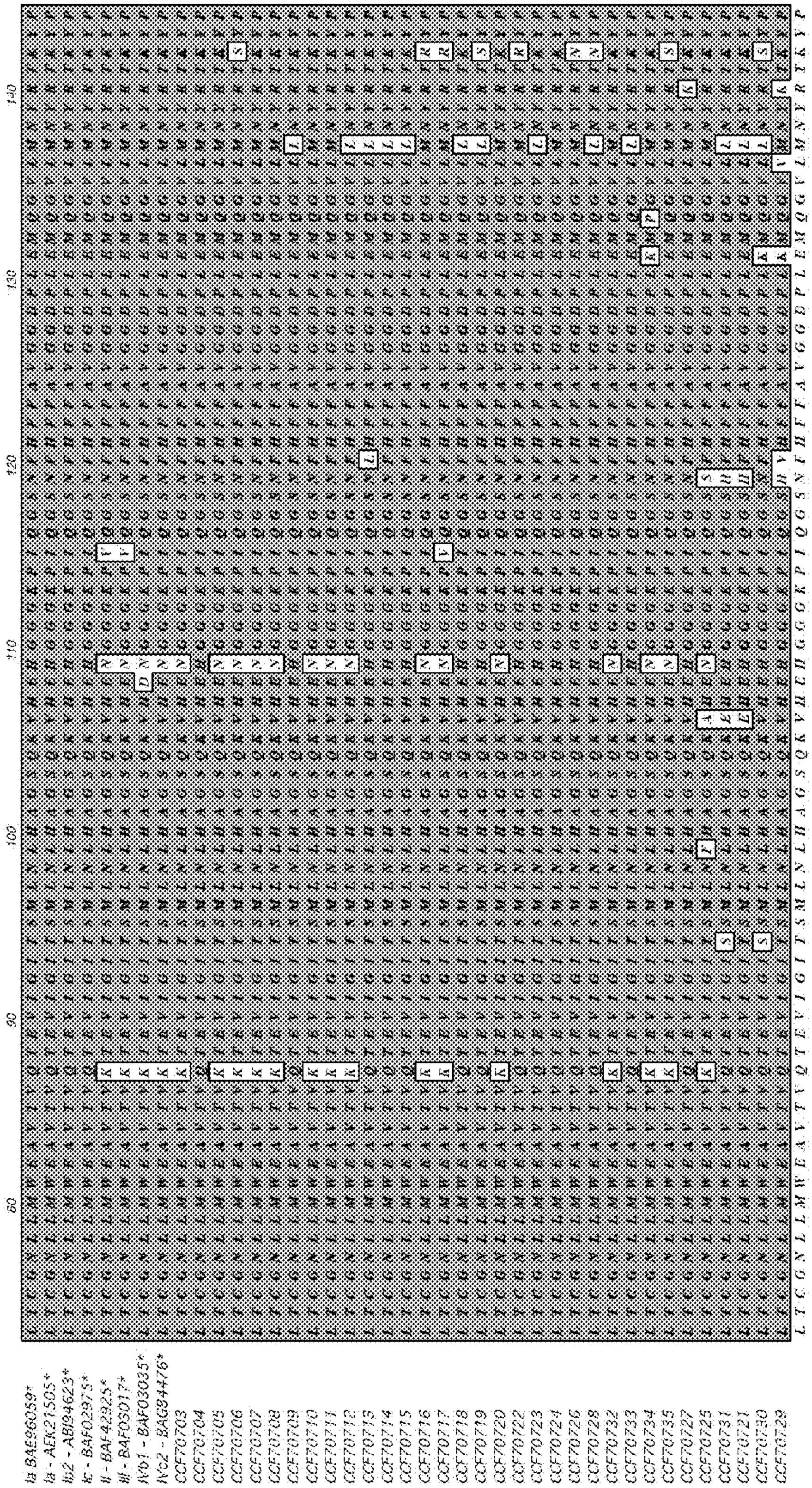

FIG. 9 is a phylogenetic tree showing the relationship of additional partial BKV VP1 sequences with selected BKV-I to BKV-IV VP1 sequences FIG. 10 is a sequence alignment of BKV partial VP1 polypeptides (SEQ ID NOs: 126-158) with amino acids 31-174 of BKV-Ia (SEQ ID NO; 52), BKV-Ia (SEQ ID NO: 75), BKV-Ib2 (SEQ ID NO: 75), BKV-Ic (SEQ ID NO: 103), BKV-II (SEQ ID NO: 105), BKV-III (SEQ ID NO: 107), BKV-IVb1 (SEQ ID NO: 125), and BKV-IVc2 (SEQ ID NO: 124) polypeptides.

SEQUENCE LISTING

Any nucleic acid and amino acid sequences listed herein or in the accompanying sequence listing are shown using standard letter abbreviations for nucleotide bases and amino acids, as defined in 37 C.F.R. 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jan. 13, 2014, and is 380,460 bytes, which is incorporated by reference herein.

SEQ ID NOs: 1-3 are amino acid sequences of exemplary BKV-Ib1 VP1, VP2, and VP3 proteins, respectively.

SEQ ID NOs: 4-6 are amino acid sequences of exemplary BKV-IVc2 VP1, VP2, and VP3 proteins, respectively.

SEQ ID NOs: 7-9 are amino acid sequences of exemplary BKV-II VP1, VP2, and VP3 proteins, respectively.

SEQ ID NOs: 10-12 are amino acid sequences of exemplary BKV-III VP1, VP2, and VP3 proteins, respectively.

SEQ ID NO: 13 is an exemplary BKV-Ia VP1 amino acid sequence.

SEQ ID NO: 14 is an exemplary BKV-Ib2 VP1 amino acid sequence.

SEQ ID NO: 15 is an exemplary BKV-Ic VP1 amino acid sequence.

SEQ ID NO: 16 is an exemplary BKV-IV-b1 VP1 amino acid sequence.

SEQ ID NOs: 17-19 are amino acid sequences of exemplary JCV-1A VP1, VP2, and VP3 proteins, respectively.

SEQ ID NO: 20 is an exemplary JCV-2A VP1 amino acid sequence.

SEQ ID NO: 21 is an exemplary JCV-3B VP1 amino acid sequence.

SEQ ID NOs: 22-23 are exemplary JCV consensus VP2 and VP3 amino acid sequences, respectively.

SEQ ID NOs: 24-26 are exemplary BKV-Ib1 VP1, VP2, and VP3 encoding nucleic acid sequences, respectively.

SEQ ID NOs: 27-29 are exemplary BKV-IVc2 VP1, VP2, and VP3 encoding nucleic acid sequences, respectively.

SEQ ID NOs: 30-32 are exemplary BKV-II VP1, VP2, and VP3 encoding nucleic acid sequences, respectively.

SEQ ID NOs: 33-35 are exemplary BKV-III VP1, VP2, and VP3 encoding nucleic acid sequences, respectively.

SEQ ID NOs: 36-38 are exemplary JCV-1A VP1, VP2, and VP3 encoding nucleic acid sequences, respectively.

SEQ ID NOs: 39-41 are exemplary codon-optimized BKV-IVc2 VP1, VP2, and VP3 polypeptide encoding nucleic acid sequences, respectively.

SEQ ID NO: 42 is an exemplary codon-optimized BKV-Ia VP1 polypeptide encoding nucleic acid sequence.

SEQ ID NO: 43 is an exemplary codon-optimized BKV-Ib2 VP1 polypeptide encoding nucleic acid sequence.

SEQ ID NO: 44 is an exemplary codon-optimized BKV-Ic VP1 polypeptide encoding nucleic acid sequence.

SEQ ID NOs: 45 and 46 are exemplary codon-optimized BKV-II and BKV-III VP1 polypeptide encoding nucleic acid sequences, respectively.

SEQ ID NO: 47 is an exemplary codon-optimized BKV-IVb1 VP1 polypeptide encoding nucleic acid sequence.

SEQ ID NO: 48 is an exemplary codon-optimized JCV-2A VP1 polypeptide encoding nucleic acid sequence.

SEQ ID NO: 49 is an exemplary codon-optimized JCV-3B VP1 polypeptide encoding nucleic acid sequence.

SEQ ID NOs: 50 and 51 are exemplary codon-optimized JCV consensus VP2 and VP3 polypeptide encoding nucleic acid sequences, respectively.

SEQ ID NOs: 52-125 are exemplary BKV VP1 polypeptide amino acid sequences.

SEQ ID NOs: 126-160 are exemplary partial BVK VP1 polypeptide amino acid sequences.

DETAILED DESCRIPTION

BKV is a ubiquitous DNA virus and up to 90% of healthy individuals are seropositive. This virus is believed to initiate infection in the urinary tract and then remain latent without disturbing its host, with occasional reactivation in the form of low-level shedding of virions in the urine (viruria).

However, in immunocompromised individuals BKV (and the related JC polyomavirus) can cause significant morbidity or even mortality.

In pediatric kidney transplants, being seronegative for BKV by a serological test before the procedure has been associated with developing PVAN. In adult kidney transplant recipients, it has been suggested that the role of donor BKV status plays a role in developing PVAN. However, pre-transplant BKV serology is not usually monitored; both because nearly all adults are believed to be seropositive for BKV, and because it has been generally believed that seropositivity for BKV is associated with protection against development of PVAN. Furthermore, the role of intravenous immunoglobulin (IVIG) in treating PVAN has been unclear.

BKV consists of four subgroups (or types; BKV-I, BKV-II, BKV-III, and BKV-IV) that have been equated with separate serotypes and have limited cross-reactivity as measured by hemagglutination inhibition (HI) and neutralization assays. However, the high BKV prevalence rates in humans, as measured by polymerase chain reaction or BKV seropositivity generally refer to serotype I only. The incidence of the other BKV types in patients prior to kidney or bone marrow transplant in Caucasians has been estimated to be about 3% for BKV-II, 6-7% for BKV-IV and undetectable for BKV-III. However, the present inventors have found a panel of sera from 48 healthy adults to be substantially higher than expected for genotypes II, III, and IV. In a few cases, the inventors have demonstrated that kidney transplant patients who initially had only BKV-I viruria later developed viruria and viremia (presence of virus in the bloodstream) with BKV-IV.

The cross-reactivity of anti-BKV antibodies between types has not been revisited since 1989; and it may have important implications in the development of PVAN in transplant patients, especially if the organ donor is positive for a less common BKV type. The present inventors have demonstrated that 23-43% of renal transplant patients with undetectable levels of BKV-IV neutralizing antibodies at the time of transplant seroconverted (changed from a negative result to a positive result in a serologic test) within one year, irrespective of their BKV-I serostatus. The small number of initially BKV-I seronegative renal transplant recipients all seroconverted for BKV-I, irrespective of their BKV-IV serostatus.

Thus, the inventors have demonstrated that presence of neutralizing antibodies against one BKV serotype does not protect from infection with other BKV serotypes, as was previously believed. Furthermore, the presence of neutralizing antibodies to BKV-Ib2 does not provide neutralization of BKV-Ia, demonstrating that not all BKV-I neutralizing antibodies can provide protection from all BKV-I subtypes. This indicates that vaccination of individuals (such as organ transplant recipients or other immunocompromised individuals) with a vaccine to a single BKV serotype or subtype may not effectively elicit an immune response to all serotypes or subtypes and may not provide adequate protection from polyomavirus-associated pathologies such as PVAN or PML. Furthermore, it indicates that the prevalence of BKV-I in the general population does not protect at risk individuals from infection with other BKV serotypes (such as BKV-IV).

I. Abbreviations

BKV BK polyomavirus
BKV-I BKV serotype I
BKV-II BKV serotype II
BKV-III BKV serotype III
BKV-IV BKV serotype IV
ELISA enzyme-linked immunosorbant assay
IVIG intravenous immunoglobulin
JCV JC polyomavirus
PML progressive multifocal leukoencephalopathy
PVAN polyomavirus-associated nephropathy
SV40 simian virus 40
VLP virus-like particle II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics,* 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a polypeptide" includes single or plural polypeptides and is considered equivalent to the phrase "comprising at least one polypeptide." As used herein, "comprises" means "includes." Thus, "comprising A or B," means "including A, B, or A and B," without excluding additional elements.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A neutralizing antibody is an antibody which, on mixture with the homologous infectious agent (such as a polyomavirus), reduces the infectious titer. In some examples, a neutralizing antibody is an antibody that blocks the ability of its antigen to perform a physiological function.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

BK polyomavirus (BKV): A polyomavirus originally isolated from patient B.K. after renal transplantation (Gardner et al., *Lancet* 1:1253-1257, 1971). Four BKV serotypes are known (serotypes I-IV; e.g., Knowles et al., *J. Med. Virol.* 28:118-123, 1989). BKV is nearly ubiquitous, and up to 90% of healthy individuals are seropositive for BKV. Acute infection is generally asymptomatic and proceeds to latent infection, primarily in the urogenital tract. BKV can be reactivated in immunocompromised individuals, and can cause significant morbidity, particularly in renal transplant patients.

BKV nucleic acid and amino acid sequences are publicly available. For example, GenBank Accession Nos. AB211374, AB263920, AB211386, and AB369093 disclose exemplary BKV-I, BKV-II, BKV-III, and BKV-IV nucleic acid sequences, respectively, all of which are incorporated by reference as present in GenBank on Jul. 15, 2011.

Capsid polypeptide: One of three structural proteins that forms the polyomavirus capsid. The polyomavirus capsid is formed from viral protein 1 (VP1), viral protein 2 (VP2), and viral protein 3 (VP3).

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells, bacteria or yeast. Codon optimization does not alter the amino acid sequence of the encoded protein.

Conservative variants: A substitution of an amino acid residue for another amino acid residue having similar biochemical properties. "Conservative" amino acid substitutions include those substitutions that do not substantially affect or decrease an activity or antigenicity of a polypeptide. A peptide can include one or more amino acid substitutions, for example 1-10 conservative substitutions, 2-5 conservative substitutions, 4-9 conservative substitutions, such as 1, 2, 5 or 10 conservative substitutions. Specific, non-limiting examples of a conservative substitution include the following examples (Table 1).

TABLE 1

Exemplary conservative amino acid substitutions

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against the unsubstituted polypeptide. Thus, in one embodiment, non-conservative substitutions are those that reduce an activity or antigenicity.

Immune response: A response of a cell of the immune system, such as a B-cell, T-cell, macrophage or polymorphonucleocyte, to a stimulus such as an antigen. An immune response can include any cell of the body involved in a host defense response, for example, an epithelial cell that secretes an interferon or a cytokine. An immune response includes, but is not limited to, an innate immune response or inflammation.

Immunocompromised: An immunocompromised subject is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms.

Those who can be considered to be immunocompromised include, but are not limited to, subjects with AIDS (or HIV positive), subjects with severe combined immunodeficiency (SCID), diabetics, subjects who have had transplants and who are taking immunosuppressants, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids or other immune suppressing therapy on a frequent basis within the last year.

Immunosuppressant: Any compound that decreases the function or activity of one or more aspects of the immune system, such as a component of the humoral or cellular immune system or the complement system. Immunosuppressants are also referred to as "immunosuppressive agents" or "immunosuppressive therapies."

In some examples, an immunosuppressant includes, but is not limited to: (1) antimetabolites, such as purine synthesis inhibitors (such as inosine monophosphate dehydrogenase (IMPDH) inhibitors, e.g., azathioprine, mycophenolate, and mycophenolate mofetil), pyrimidine synthesis inhibitors (e.g., leflunomide and teriflunomide), and antifolates (e.g., methotrexate); (2) calcineurin inhibitors, such as tacrolimus, cyclosporine A, pimecrolimus, and voclosporin; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus, and biolimus A9; (6) corticosteroids, such as prednisone; and (7) antibodies to any one of a number of cellular or serum targets (including anti-lymphocyte globulin and anti-thymocyte globulin).

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., rituximab, afutuzumab, ocrelizumab, pascolizumab); CD23 (e.g., lumiliximab); CD40 (e.g., teneliximab, toralizumab); CD52 (e.g., alemtuzumab); CD62L/L-selectin (e.g., aselizumab); CD80 (e.g., galiximab); CD147/basigin (e.g., gavilimomab); CD154 (e.g., ruplizumab); BLyS (e.g., belimumab); CTLA-4 (e.g., ipilimumab, tremelimumab); CAT (e.g., bertilimumab, lerdelimumab, metelimumab); integrin (e.g., natalizumab); IL-6 receptor (e.g., tocilizumab); LFA-1 (e.g., odulimomab); and IL-2 receptor/CD25 (e.g., basiliximab, daclizumab, inolimomab).

Inhibiting or treating a disease: "Inhibiting" a disease refers to inhibiting the full development of a disease, for example, PVAN, PML, or BKV-associated hemorrhagic cystitis. Inhibition of a disease can span the spectrum from partial inhibition to substantially complete inhibition (e.g., including, but not limited to prevention) of the disease. In some examples, the term "inhibiting" refers to reducing or delaying the onset or progression of a disease. A subject to be administered with a therapeutically effective amount of the disclosed immunogenic compositions can be identified by standard diagnosing techniques for such a disorder, for example, basis of family history, or risk factor to develop the disease or disorder. "Treatment" refers to a therapeutic intervention that ameliorates a sign or symptom of a disease or pathological condition after it has begun to develop.

Isolated: An "isolated" or "purified" biological component (such as a nucleic acid, peptide, protein, protein complex, or virus-like particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

JC polyomavirus (JCV): A polyomavirus originally isolated from a patient (J.C.) with progressive multifocal leukoencephalopathy (Padgett et al., *Lancet* 1:1257-1260, 1971). JCV is genetically similar to BKV and simian virus 40 (SV40). JCV is very common in the general population, with 70-90% of individuals seropositive for JCV. The initial site of infection may be the tonsils or gastrointestinal tract. The primary sites of JC infection are thought to be tubular epithelial cells in the kidney, the lining of the ureters and bladder, and oligodendrocytes and astrocytes in the central nervous system.

JCV can reactivate in immunocompromised individuals and can cause JCV-associated progressive multifocal leukoencephalopathy (PML), which is usually fatal. PML occurs in about 10% of patients suffering from HIV-induced AIDS and can also occur in other immunosuppressed patients, including but not limited to patients treated with rituximab, natalizumab, alemtuzumab, or efalizumab. JCV can also cause urinary tract pathology in some organ transplant recipients.

JCV nucleic acid and amino acid sequences are publicly available. For example, GenBank Accession Nos. NC_001699, AB038251, and AF281600 disclose exemplary JCV nucleic acid sequences, all of which are incorporated by reference as present in GenBank on Jul. 15, 2011. JCV isolates have been classified into eight distinct genotypes, based in part on the amino acid sequences of VP1 proteins of individual isolates (Cubitt et al., *J. Neurovirol.* 7:339-344, 2001).

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic compositions, such as one or more polyomavirus capsid polypeptides or fragments thereof, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polyomavirus: A genus of nonenveloped viruses having an icoshedral capsid. The genome of polyomaviruses includes non-structural proteins (large T-antigen and small t-antigen), a non-coding region including an origin of replication and promoters, and structural proteins (VP1, VP2, and VP3). Polyomaviruses include but are not limited to BK polyomavirus, JC polyomavirus, Merkel cell polyomavirus, and simian virus 40 (SV40). Related human polyomaviruses WU virus (Gaynor et al., *PLoS Pathog.* 3:e64, 2007) and KI virus (Allander et al., *J. Virol.* 81:4130-4136, 2007) have recently been reported in clinical samples Polyomavirus infection is generally asymptomatic in healthy subjects. However, polyomavirus infection can occur or be reactivated in immunocompromised individuals and can cause significant morbidity. Polyomavirus-associated nephropathy (PVAN; also called BK polyomavirus-associated nephropathy or BK virus nephritis) occurs in up to 10% of renal transplant recipients and is believed to be caused by BKV infection or reactivation of latent BKV infection. It causes kidney allograft dysfunction and may lead to loss of the allograft. Polyomavirus-associated hemorrhagic cystitis is characterized by inflammation of the bladder leading to dysuria, hematuria, and hemorrhage. It can occur in bone marrow transplant recipients and other individuals who are receiving immunosuppressants or other therapies which decrease immune system function.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman, *Adv. Appl. Math.* 2: 482, 1981; Needleman & Wunsch, *J. Mol. Biol.* 48: 443, 1970; Pearson & Lipman, *Proc. Natl. Acad. Sci. USA* 85: 2444, 1988; Higgins & Sharp, *Gene,* 73: 237-244, 1988; Higgins & Sharp, *Comput. Appl. Biosci.* 5: 151-153, 1989; Corpet et al., *Nucl. Acids Res.* 16, 10881-90, 1988; Huang et al., *Comput. Appl. Biosci.* 8, 155-65, 1992; and Pearson, *Methods Mol. Biol.* 24:307-331, 1994. Altschul et al. (*J. Mol. Biol.* 215:403-410, 1990) presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent sufficient to achieve a desired effect in a subject being treated with that agent. For example, this may be the amount of a polyomavirus capsid polypeptide or nucleic acid (or fragment thereof) useful for eliciting an immune response in a subject and/or for inhibiting or preventing infection or pathology by a polyomavirus (such as BKV or JCV). Ideally, in the context of the present disclosure, a therapeutically effective amount of a polyomavirus polypeptide or nucleic acid (or fragment thereof) is an amount sufficient to increase resistance to, prevent, ameliorate, and/or treat infection caused by a polyomavirus in a subject without causing a substantial cytotoxic effect in the subject. The effective amount of a polyomavirus polypeptide or nucleic acid (or fragment thereof) useful for increasing resistance to, preventing, ameliorating, and/or treating infection in a subject will be dependent on, for example, the subject being treated, the manner of administration of the therapeutic composition, and other factors.

Virus-like particle (VLP): A non-replicating viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

III. Immune Response to Polyomavirus

Disclosed herein are methods of eliciting an immune response against a polyomavirus (for example, BKV or JCV). The disclosed methods utilize one or more capsid polypeptides (or a fragment thereof) of a polyomavirus to elicit an immune response in a subject. In some examples, the methods are of use to treat, inhibit, or even prevent infection of a subject with a polyomavirus or to treat, inhibit, or even prevent polyomavirus-associated disorders (for example, PVAN, BKV-associated hemorrhagic cystitis, and/or JCV-associated PML). In some embodiments, the methods include administering at least one capsid polypeptide (or a fragment thereof) from each of two or more BKV serotypes (such as a multivalent BKV serotype immunogenic composition) to a subject. In some embodiments, the multivalent immunogenic composition includes at least one capsid polypeptide (or a fragment thereof) from two or more BKV-I subtypes (such as BKV-Ia, BKV-Ib1, BKV-Ib2, and/or BKV-Ic subtypes). In additional embodiments, the methods further include administering at least one JCV capsid polypeptide (or a fragment thereof) to the subject. Also disclosed are methods of identifying a transplant donor and/or transplant recipient (such as a renal transplant donor or recipient) who does not have antibodies for one or more BKV serotypes (for example, BKV-IV or BKV-I), such as a donor and/or recipient who does not have detectable levels of antibodies capable of neutralizing one or more BKV serotypes (for example, BKV-I or BKV-IV).

A. Methods of Eliciting an Immune Response to BKV

In some embodiments, the methods include eliciting an immune response against a BKV in a subject (such as one or more BKV serotypes). The methods include administering to a subject in need of enhanced immunity to BKV a therapeutically effective amount of at least one isolated BKV-I capsid polypeptide (or a fragment thereof) or a nucleic acid encoding the at least one BKV-I capsid polypeptide (such as at least one BKV-Ia VP1 polypeptide, BKV-Ib1 VP1 polypeptide, BKV-Ib2 VP1 polypeptide, and/or BKV-Ic VP1 polypeptide) and a therapeutically effective amount of at least one isolated BKV-IV capsid polypeptide (or a fragment thereof) or a nucleic acid encoding the at least one BKV-IV capsid polypeptide (such as at least one BKV-IVb1 VP1 polypeptide and/or BKV-IVc2 VP1 polypeptide). In some examples, the at least one BKV-I capsid polypeptide (or fragment thereof) and the at least one BKV-IV capsid polypeptide (or fragment thereof) are different from one another. The BKV-I and BKV-IV capsid polypeptides include one or more of VP1, VP2, and VP3 (such as SEQ ID NOs: 1-6 and 13-16), and are discussed in detail in Section IV, below. In particular examples, administering the at least one isolated BKV-I capsid polypeptide includes administering a VLP including the BKV-I capsid polypeptide(s) and/or administering the at least one BKV-IV capsid polypeptide includes administering a VLP including the BKV-IV capsid polypeptide(s). In particular examples, the subject does not have BKV-IV neutralizing antibodies. In other examples, the subject does not have BKV-I neutralizing antibodies.

In one non-limiting example, the methods include administering to a subject in need of enhanced immunity to BKV a therapeutically effective amount of at least one BKV-Ia VP1 polypeptide, at least one BKV-Ib2 VP1 polypeptide, and at least one BKV-IV VP1 polypeptide (such as at least one BKV-IVb1 VP1 polypeptide and/or BKV-IVc2 VP1 polypeptide). In other examples, the methods may also include administering to a subject in need of enhanced immunity to BKV a therapeutically effective amount of at least one BKV-Ic VP1 polypeptide. In some examples, the BKV-Ia/Ib1 VP1 polypeptide includes a glutamic acid at amino acid position 73 and/or a glutamic acid at amino acid position 82 (such as SEQ ID NO: 1 or SEQ ID NO: 13). In additional examples, the BKV-Ib2 VP1 polypeptide includes a lysine residue at amino acid position 73 and/or an aspartic acid at amino acid position 82 (such as SEQ ID NO: 14).

In some examples, the methods further include administering to the subject a therapeutically effective amount of at least one isolated BKV-II capsid polypeptide (or a fragment thereof) or a nucleic acid encoding the at least one BKV-II capsid polypeptide and/or a therapeutically effective amount of at least one BKV-III capsid polypeptide (or a fragment thereof) or a nucleic acid encoding the at least one BKV-III capsid polypeptide. In some examples, the BKV-II capsid polypeptide (or fragment thereof) and the BKV-III capsid polypeptide (or fragment thereof) are different from one another and are also different from the BKV-I and BKV-IV capsid polypeptides (or fragments thereof). The BKV-II and BKV-III capsid polypeptides include one or more of VP1, VP2, and VP3 (such as SEQ ID NOs: 7-12), and are discussed in detail in Section IV, below. In particular examples, administering the at least one isolated BKV-II capsid polypeptide includes administering a VLP including the BKV-II capsid polypeptide(s) and/or administering the at least one BKV-III capsid polypeptide includes administering a VLP including the BKV-III capsid polypeptide(s).

In some embodiments, the methods further include selecting a subject in need of enhanced immunity to BKV. In some examples, a subject in need of enhanced immunity to BKV is a subject at risk of BKV infection or at risk of BKV-associated disorders, such as PVAN or BKV-associated hemorrhagic cystitis. Subjects in need of enhanced immunity to BKV include subjects who are immunocompromised, for example subjects who are infected with human immunodeficiency virus (HIV), subjects with SCID, diabetics, subjects who are receiving chemotherapy for cancer, and subjects who are receiving immunosuppressive therapy (such as corticosteroids, a calcineurin inhibitor, such as tacrolimus, cyclosporine, or pimecrolimus, or other therapies that decrease immune system function, such as rituximab, natalizumab, efalizumab, or alemtuzumab). In some examples, subjects who are receiving immunosuppressive therapy include individuals who have received an organ transplant (such as a renal transplant or other solid organ transplant or a bone marrow transplant). In a particular example, a subject in need of enhanced immunity to BKV is a renal transplant recipient. In another example, a subject in need of enhanced immunity to BKV is a bone marrow transplant recipient. In other examples, subjects in need of enhanced immunity to BKV include those who are candidates for organ or bone marrow transplantation or those who are candidates for immunosuppressive therapy. In a particular example, the subject has renal failure or is otherwise a candidate for a renal transplant. In further examples, a subject in need of enhanced immunity to BKV may include a subject who has or is at risk for cancer (for example, prostate cancer or bladder carcinoma).

In additional embodiments, the methods further include administering to the subject a therapeutically effective amount of at least one JCV capsid polypeptide (or a fragment thereof) or a nucleic acid encoding the at least one JCV capsid polypeptide. The JCV capsid polypeptides include one or more of VP1, VP2, and VP3 (for example, SEQ ID NOs: 17-23), and are discussed in detail in Section IV, below. In particular examples, administering the at least one isolated JCV capsid polypeptide includes administering a VLP including the JCV capsid polypeptide(s).

In some examples, the subject who is administered the at least one JCV capsid polypeptide or nucleic acid encoding the JCV capsid polypeptide is a subject in need of enhanced immunity to JCV or a subject at risk of a JCV-associated disorder (for example, JCV-associated PML). In particular examples, the subject is an immunocompromised subject, for example a subject who is infected with HIV, a subject with SCID, a diabetic subject, a subject who is receiving chemotherapy for cancer, or a subject who is receiving immunosuppressive therapy (such as corticosteroids, a calcineurin inhibitor, such as tacrolimus, cyclosporine, or pimecrolimus, or other therapies that decrease immune system function, such as rituximab, natalizumab, efalizumab, or alemtuzumab). In some examples, a subject who is receiving immunosuppressive therapy includes a subject who has received an organ transplant (such as a renal transplant or other solid organ transplant or a bone marrow transplant). In a particular example, a subject in need of enhanced immunity to JCV is a renal transplant recipient or a bone marrow transplant recipient. In another example, a subject in need of enhanced immunity to JCV is a subject who is receiving rituximab therapy (or a subject who will or has received rituximab therapy). In other examples, subjects in need of enhanced immunity to JCV include those who are candidates for organ or bone marrow transplantation or those who are candidates for immunosuppressive therapy.

B. Methods of Treating or Inhibiting Polyomavirus-Associated Disorders

In some embodiments, the methods include treating or inhibiting (or in some examples, even preventing) a polyomavirus-associated disorder, such as PVAN, BKV-associated hemorrhagic cystitis, or JCV-associated PML. In some examples, the methods include administering to a subject in need of treatment for or inhibition of a polyomavirus-associated disorder a therapeutically effective amount of at least one isolated BKV-IV capsid polypeptide (or a fragment thereof) or a nucleic acid encoding the at least one BKV-IV capsid polypeptide to the selected subject (such as at least one BKV-IVb1 VP1 polypeptide and/or at least one BKV-IVc2 VP1 polypeptide). In some examples, administering the one or more BKV-IV capsid polypeptides (such as VP1, VP2, or VP3, for example, SEQ ID NOs: 4-6 and/or SEQ ID NO: 16) includes administering a VLP including the capsid polypeptide(s).

In some embodiments, the methods further include selecting a subject in need of treatment for inhibition of a polyomavirus-associated disorder. In some examples, a subject is need of treating or inhibiting PVAN or BK-associated hemorrhagic cystitis, (such as a subject who has had an organ or bone marrow transplant or a candidate for an organ or bone marrow transplant). In one example, the subject is a candidate for a kidney transplant. In other examples, the subject is a candidate for a bone marrow transplant. In further examples, the subject is immunocompromised (such as a transplant recipient, a subject who is infected with HIV, or a subject treated with an immunosuppressant), or is a candidate for treatment with an immunosuppressant (such as an organ or bone marrow transplant candidate). In particular examples, the subject does not have BKV-IV neutralizing antibodies and/or BKV-I neutralizing antibodies.

In some examples, the methods further include administering to the subject a therapeutically effective amount of at least one isolated BKV-I capsid polypeptide (or a fragment thereof) or a nucleic acid encoding the at least one BKV-I capsid polypeptide, at least one isolated BKV-II capsid polypeptide (or a fragment thereof) or a nucleic acid encoding the at least one BKV-II capsid polypeptide, at least one isolated BKV-III capsid polypeptide (or a fragment thereof) or a nucleic acid encoding the at least one BKV-III capsid polypeptide, at least one isolated JCV capsid polypeptide (or a fragment thereof) or a nucleic acid encoding the at least one JCV capsid polypeptide, or a combination of two or more thereof (for example, one or more of SEQ ID NOs: 1-23). In particular non-limiting examples, the methods include administering to the subject a therapeutically effective amount of at least one BKV-Ia VP1 polypeptide and at least one BKV-Ib2 VP1 polypeptide (such as SEQ ID NOs: 1, 14, or 15). In some examples, administering the one or more BKV and/or JCV capsid polypeptides (such as VP1, VP2, or VP3) includes administering a VLP including the capsid polypeptide(s).

In particular examples, the subject is a candidate for organ transplant (for example, renal transplant or bone marrow transplant) and the therapeutically effective amount of the BKV-IV capsid polypeptide or nucleic acid encoding the capsid polypeptide is administered to the subject a sufficient time prior to the organ transplant to produce an immune response to the BKV-IV capsid polypeptide in the subject. One of skill in the art can identify the time required to produce an immune response in the subject based on factors such as the general state of the subject's health, and the robustness of the subject's immune system. In some examples, the at least one isolated BKV-IV capsid polypeptide or nucleic acid encoding the BKV-IV capsid polypeptide is administered to the subject at least about six months (for example, at least about 6 months, 5 months, 4 months, 3 months, 2 months, 6 weeks, 5 weeks, 4 weeks, 3 weeks, 2 weeks, or even 1 week) prior to the organ transplant. In some examples, the BKV-IV capsid polypeptide is administered to the subject at least about 2 weeks prior to the organ transplant. In other examples, the BKV-IV capsid polypeptide is administered to the subject at least about 6 weeks prior to the organ transplant, with a booster dose about 2 weeks prior to transplant. In some examples, a BKV-I, BKV-II, BKV-III, and/or JCV capsid polypeptide (or fragment thereof) is further administered to the subject prior to the organ transplant.

In additional embodiments, the methods include administering to the subject a therapeutically effective amount of a purified human gamma globulin preparation that has been found to contain antibodies capable of neutralizing BKV-I, BKV-II, BKV-III and/or BKV-IV. Subjects include those described above. Methods of identifying serum containing BKV-I, BKV-II, BKV-III, and/or BKV-IV neutralizing antibodies are known to one of skill in the art and include the methods discussed in Section VI, below. In some examples, the gamma globulin preparations that may be used include commercially available preparations of intact gamma globulin and preparations of the Fc, $F(ab')_2$ fragments of gamma globulin or combinations thereof. Methods of preparing gamma globulin, for example, for administration to a subject are known to one of ordinary skill in the art. See, e.g., U.S. Pat. Nos. 5,177,194; 6,504,012; and 7,879,331.

The dosage of gamma globulin and the method of administration will vary with the severity and nature of the particular condition being treated, the duration of treatment, the adjunct therapy used, the age and physical condition of the subject of treatment and similar factors. In some examples, dosages for intravenous administration are from 100 mg/kg to 2.5 g/kg (such as about 400 mg/kg to 2 g/kg or 1 g/kg to 2 g/kg). The dosage can be varied based on the frequency of administration, for example, 400 mg/kg/day for 5 consecutive days per month or 2 g/kg/day once a month. In another example, the gamma globulin preparation is administered subcutaneously or intramuscularly. In some examples, the dosage for subcutaneous or intramuscular administration is from about 1 mg/kg to 30 mg/kg body weight (such as about 4 mg/kg to 20 mg/kg or about 10 mg/kg to 20 mg/kg). The gamma globulin is administered as a pharmaceutical composition containing a pharmaceutically acceptable carrier. Pharmaceutically acceptable carriers of use for gamma globulin compositions include those described in section V, below.

C. Methods of Selecting a Renal Transplant Donor and/or Recipient

In further embodiments, the methods include selecting a candidate organ transplant donor and/or organ transplant recipient. In some examples, the candidate donor is a candidate renal transplant donor and the candidate transplant recipient is a candidate renal transplant recipient. The methods include screening a candidate donor and/or recipient for presence of BKV serotype-specific antibodies (including, but not limited to BKV-IV-specific neutralizing antibodies).

In some embodiments, the methods include selecting a subject as a renal transplant donor if BKV serotype-specific (such as BKV-IV or BKV-I) neutralizing antibodies are not present in the subject. In some examples, the methods further include selecting a subject as a renal transplant recipient if BKV serotype-specific (such as BKV-IV or BKV-I) neutralizing antibodies are not present in the subject who is a candidate transplant recipient. In some examples, the methods include detecting presence of BKV-IV neutralizing antibodies in a subject (for example, in a sample from a subject) and selecting the subject as a transplant donor or recipient if BKV-IV neutralizing antibodies are not present in the sample. The sample can include any suitable biological sample from the subject, including a blood sample or serum sample.

Methods of detecting neutralizing antibodies in a subject (such as in a blood or serum sample from a subject) are known to one of ordinary skill in the art. Such methods are discussed in Section VI, below.

IV. Polyomavirus Capsid Polypeptides

Polyomavirus nucleic acid and polypeptide sequences are publicly available and can be identified by one of skill in the art. Exemplary BKV genomic nucleic acid sequences include, but are not limited to, GenBank Accession Nos. JF894228, AB211374, DQ989796, AB211377, AB263920, AB211386, AB211390, and AB369093, each of which is incorporated herein by reference as present in GenBank on Jul. 15, 2011.

It is disclosed herein that several BKV capsid polypeptides (or fragments thereof) can be used to elicit an immune response to BKV. In several embodiments, the BKV capsid polypeptide comprises or consists of the amino acid sequence set forth as SEQ ID NOs: 1-12. Additional BKV VP1 polypeptides are disclosed herein, for example from additional BKV subtypes. In some embodiments, the BKV VP1 polypeptide comprises or consists of the amino acid sequence set forth as SEQ ID NOs: 13-16.

Exemplary JCV genomic nucleic acid sequences include, but are not limited to, GenBank Accession Nos. NC_001699, AF300945, and AY536541, each of which is incorporated herein by reference as present in GenBank on Jul. 15, 2011.

It is also disclosed herein that several JCV capsid polypeptides (or fragments thereof) can be used to elicit an immune response to JCV, for example, in combination with one or more BKV capsid polypeptides. In several embodiments, the JCV capsid polypeptide comprises or consists of the amino acid sequence set forth as SEQ ID NOs: 17-23.

In some embodiments, the polyomavirus capsid polypeptides (such as BKV or JCV capsid polypeptides) of use in the methods disclosed herein have a sequence at least 90%, 91%, 92%, 93%, 94%, 95%, 96%, 97%, 98%, or 99%, such as 100% identical to the amino acid sequence set forth in one of SEQ ID NOs: 1-23 or 52-125. In other examples, the polyomavirus capsid polypeptides (such as BKV VP1 polypeptides) comprise a sequence at least 90%, 91%, 92%, 93%, 94%, 95%, 96%, 97%, 98%, or 99%, such as 100% identical to the amino acid sequence set forth in one of SEQ ID NOs: 126-158. In some examples, the BKV subtype or serotype of the polypeptide is known. In other examples, the BKV subtype or serotype of the polypeptide is not known. One of ordinary skill in the art can determine the BKV subtype or serotype of an unknown BKV capsid polypeptide, for example by sequence analysis and ELISA or neutralizing assays (such as those described in Examples 1-3, below). Exemplary sequences can be obtained using computer programs that are readily available on the internet and the amino acid sequences set forth herein. In one example, the polypeptide retains a function of the polyomavirus capsid polypeptide, such as binding to an antibody that specifically binds the polyomavirus epitope.

Minor modifications of a polyomavirus capsid polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of a polyomavirus capsid polypeptide is a conservative variant of the polyomavirus capsid polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided herein. Substitutions of the amino acids sequence shown in SEQ ID NOs: 1-23 or 52-158 can be made based on this table.

An "epitope" or "antigenic determinant" refers to a site on an antigen to which B and/or T cells respond. T cells can respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as 5, 6, 7, 8, 9, 10, 11, 12, 13, 14, or 15 amino acids. In some examples, the immunogenic compositions disclosed herein include a fragment (such as an immunogenic fragment) or antigenic determinant of a polyomavirus capsid protein. One of skill in the art can identify predicted antigenic determinants, for example using an HLA peptide binding prediction program, such as BIMAS (www-bimas.cit.nih.gov/molbio/hla_bind/) or IEDB analysis resource (immuneeptiope.org). In some examples, the polyomavirus capsid polypeptide includes, consists essentially of, or consists of five or more amino acids (for example, 5, 6, 7, 8, 9, 10, 11, 12, 13, 14, 15, 16, 17, 18, 19, 20, 21, 22, or 23 amino acids) of the VP1 BC loop (e.g., amino acids 61-83 of a BKV VP1 polypeptide; see, e.g., Tremolada et al., *Virus Res.* 149:190-196, 2010).

The polyomavirus capsid polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding at least one polyomavirus capsid polypeptide or an epitope thereof into an expression vector, introducing the expression vector into a host cell, and isolating the polypeptide. Any suitable cell can be utilized to express the disclosed polypeptides, including bacteria (e.g., *E. coli*), yeast, insect cells (e.g., Sf9 cells), or mammalian cells (e.g., 293 cells). In some examples, the polypeptide spontaneously assembles into a virus-like particle (VLP).

In some examples, the disclosed polyomavirus capsid polypeptides (or fragments thereof), for example a capsid polypeptide comprising the amino acid sequence of one or more of SEQ ID NOs: 1-23 or 52-125, are a part of a VLP, such as a BKV-I VLP, BKV-II VLP, BKV-III VLP, BKV-IV VLP, or JCV VLP. Immunogens are typically presented multimerically (e.g., about 72 pentamers or about 360 capsid polypeptides per VLP particle) to immune cells such as B cells and antigen presenting cells. This results in effectively inducing immune responses against the immunogen, in particular, antibody responses. In some examples, the VLP includes one or more of VP1, VP2, and VP3 (such as 1, 2, or all 3) from BKV-I (such as BKV-Ia, BKV-Ib1, BKV-Ib2, and/or BKV-Ic), BKV-II, BKV-III, BKV-IV (such as BKV-IVb1 and/or BKV-IVc2), or JCV.

In specific embodiments, the antigen that is part of the disclosed VLPs includes one or more of the amino acid sequences set forth as SEQ ID NOs: 1-23 or 52-158 (or fragments thereof) and have the ability to spontaneously assemble into VLPs. In some examples, a VLP includes a BKV-I VP1 polypeptide (such as one of SEQ ID NOs: 1, 13, 14, or 15) and a BKV-I VP2 polypeptide (such as SEQ ID NO: 2) and/or BKV-I VP3 polypeptide (such as SEQ ID NO: 3). In other examples, a VLP includes a BKV-I VP1 polypeptide (such as one of SEQ ID NOs: 1, 13, 14, or 15) and a BKV-IV VP2 polypeptide (such as SEQ ID NO: 5) and/or BKV-IV VP3 polypeptide (such as SEQ ID NO: 6). In other examples, a VLP includes a BKV-II VP1 polypeptide (such as SEQ ID NO: 7) and a BKV-II VP2 polypeptide (such as SEQ ID NO: 8) and/or BKV-II VP3 polypeptide (such as SEQ ID NO: 9). In other examples, a VLP includes a BKV-II VP1 polypeptide (such as SEQ ID NO: 7) and a BKV-IV VP2 polypeptide (such as SEQ ID NO: 5) and/or BKV-IV VP3 polypeptide (such as SEQ ID NO: 6). In additional examples, a VLP includes a BKV-III VP1 polypeptide (such as SEQ ID NO: 10) and a BKV-III VP2 polypeptide (such as SEQ ID NO: 11) and/or BKV-III VP3 polypeptide (such as SEQ ID NO: 12). In other examples, a VLP includes a BKV-III VP1 polypeptide (such as SEQ ID NO: 10) and a BKV-IV VP2 polypeptide (such as SEQ ID NO: 5) and/or BKV-IV VP3 polypeptide (such as SEQ ID NO: 6). In still further examples, a VLP includes a BKV-IV VP1 polypeptide (such as one of SEQ ID NOs: 4 and 16) and a BKV-IV VP2 polypeptide (such as SEQ ID NO: 5) and/or BKV-IV VP3 polypeptide (such as SEQ ID NO: 6). In another example, a VLP includes a JCV VP1 polypeptide (such as one of SEQ ID NOs: 17, 20, or 21) and a JCV VP2 polypeptide (such as SEQ ID NO: 22) and/or JCV VP3 polypeptide (such as SEQ ID NO: 23).

In further examples, a fragment of a disclosed polyomavirus capsid polypeptide retains the ability to spontaneously assemble into VLPs. Fragments (such as immunogenic fragments) and variants can be of varying length. For example, a fragment may consist of six or more, 25 or more, 50 or more, 75 or more, 100 or more, or 200 or more amino acid residues of a polyomavirus capsid amino acid sequence. This includes, for example, any polypeptide six or more amino acid residues in length that is capable of spontaneously assembling into VLPs. Methods to assay for VLP formation and isolation of VLPs are well known in the art (see, for example, Pastrana et al., *PLoS Pathogens* 5(9): e1000578, 2009, herein incorporated by reference in its entirety).

Polynucleotides encoding the BKV capsid polypeptides disclosed herein are also provided. Exemplary nucleic acid sequences are set forth as SEQ ID NOs: 24-35. Polynucleotides encoding the JCV capsid polypeptides disclosed herein are also provided. Exemplary nucleic acid sequences are set forth as SEQ ID NOs: 36-38.

In some embodiments, the nucleic acids encoding the BKV capsid polypeptides are codon-optimized for expression in a heterologous system (such as mammalian cells, bacteria or yeast). Exemplary nucleic acid sequences codon-optimized for mammalian cells are set forth as SEQ ID NOs: 39-51 (although the codon-optimized sequences can still be expressed in other systems, such as bacteria).

In some embodiments, the nucleic acid sequences encoding polyomavirus capsid polypeptides (such as BKV or JCV capsid polypeptides) of use in the methods disclosed herein have a sequence at least 85%, 90%, 95%, 96%, 97%, 98%, or 99%, such as 100% identical to the nucleic acid sequence set forth in one of SEQ ID NOs: 24-51. Exemplary sequences can be obtained using computer programs that are readily available on the internet and the nucleic acid sequences set forth herein. In one example, the polypeptide encoded by the nucleic acid sequence retains a function of the polyomavirus capsid polypeptide, such as binding to an antibody that specifically binds the polyomavirus epitope.

V. Pharmaceutical Compositions and Modes of Administration

The polyomavirus capsid polypeptides (or fragments thereof) disclosed herein, or nucleic acids encoding the polyomavirus capsid polypeptides, can be used to elicit an immune response in a subject. In several examples, the subject is infected with at least one BKV serotype or is at risk of being infected with a BKV serotype (such as one or more of BKV-I, BKV-II, BKV-III, or BKV-IV) and/or JCV. Thus, in several embodiments, the methods include administering to a subject a therapeutically effective amount of one or more of the polyomavirus capsid polypeptides (or fragments thereof) disclosed herein (or polynucleotides encoding these polypeptides) in order to elicit an immune response, such as, but not limited to, a protective immune response.

In the disclosed methods, compositions are administered to a subject in an amount sufficient to produce an immune response to a polyomavirus (for example, BKV). The disclosed BKV polypeptides, VLPs including the BKV polypeptides, or polynucleotides encoding these polypeptides, are of use to inhibit (or even prevent) an infection with BKV in a subject, inhibit (or even prevent) progression to disease in a subject having a latent BKV infection, or to inhibit or treat BKV-associated disorders (for example, PVAN or BKV-associated hemorrhagic cystitis) in a subject infected with BKV. In several examples, administration of a therapeutically effective amount of a composition including one or more BKV serotype-specific capsid polypeptides (or fragments thereof) disclosed herein (or polynucleotides encoding these polypeptides) induces a sufficient immune response to decrease a symptom of a disease due to BKV infection, to inhibit the development of one or more symptoms of BKV or a BKV-associated disorder, or to inhibit infection with BKV (such as a BKV serotype, for example, BKV-I, BKV-II, BKV-III, and/or BKV-IV).

In some examples, the compositions are of use in inhibiting or even preventing a future infection with BKV. Thus, in some examples, a therapeutically effective amount of the composition is administered to a subject at risk of becoming infected with BKV (for example, an immunocompromised subject or a subject who has received or is a candidate for an organ transplant). The composition inhibits the development of BKV, such as latent or active BKV infection, in the subject upon subsequent exposure to BKV, or loss of immunological control over an existing BKV infection (for example reactivation of a latent infection).

In some embodiments, the methods further include administering to a subject a therapeutically effective amount of one or more of the JCV capsid polypeptides (or fragment thereof) disclosed herein (or polynucleotides encoding these polypeptides) in order to elicit an immune response, such as, but not limited to, a protective immune response against JCV. In some examples, the compositions are of use in inhibiting or even preventing a future infection with JCV. Thus, in some examples, a therapeutically effective amount of the composition is administered to a subject at risk of becoming infected with JCV (for example, an immunocompromised subject or a subject who has or is a candidate for organ transplantation). The composition inhibits or prevents the development of JCV, such as latent or active JCV infection, in the subject upon subsequent exposure to JCV, or loss of immunological control over an existing JCV infection (for example reactivation of a latent infection). In some examples, the disclosed methods and compositions inhibit or treat JCV-associated disorders (for example, JCV-associated PML) in a subject infected with JCV. In particular examples, the subject is at risk of developing JCV-associated PML, such as a subject infected with HIV, a subject on immune-suppressing therapy (for example, mycophenolate, fludarabine, methotrexate, rituximab, natalizumab, alemtuzumab, or efalizumab), or a subject who has, or is a candidate for, organ transplantation (such as a bone marrow transplant).

Amounts effective for these uses will depend upon the severity of the disease, the general state of the subject's health, and the robustness of the subject's immune system. In one example, a therapeutically effective amount of the compound is that which provides either subjective relief of a symptom or an objectively identifiable improvement as noted by the clinician or other qualified observer. In other examples, a therapeutically effective amount is an amount sufficient to inhibit an infection with BKV (such as BKV-I, BKV-II, BKV-III, and/or BKV-IV) in a subject upon subsequent exposure of the subject to one or more BKV serotypes. In additional examples, a therapeutically effective amount is an amount sufficient to inhibit development of one or more symptoms in a subject infected with BKV (for example, PVAN or BKV-associated hemorrhagic cystitis).

In further examples, a therapeutically effective amount is an amount sufficient to inhibit an infection with JCV in a subject upon subsequent exposure of the subject to one or more JCV serotypes or inhibit the emergence of an existing JCV infection from asymptomatic latency in a subject. In additional examples, a therapeutically effective amount is an amount sufficient to inhibit development of one or more symptoms in a subject infected with JCV (for example, JCV-associated PML).

In some examples, one or more polyomavirus capsid polypeptides (such as BKV or JCV capsid polypeptides) or fragments thereof described herein may be covalently linked to at least one other immunogenic protein, wherein the conjugate elicits an immune response to the polyomavirus capsid polypeptide in a subject. The other immunogenic protein (sometimes referred to as a "carrier" protein) ideally has the properties of being immunogenic by itself, usable in a subject, and of a size that can be easily purified and conjugated to at least one other protein or peptide. Suitable carrier proteins are known to one of skill in the art. In particular examples, the other immunogenic protein (carrier protein) is bovine serum albumin (BSA), ovalbumin, tetanus toxoid, diphtheria toxoid, cholera toxin, *Clostridium difficile* toxin A, *C. difficile* toxin B, Shiga toxin, or *Pseudomonas aeruginosa* recombinant exoprotein A.

A polyomavirus capsid polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular injection, subcutaneous injection, intraperitoneal injection, intravenous injection, oral administration, nasal administration, transdermal administration, or even anal administration. In some embodiments, administration is by oral administration, subcutaneous injection, or intramuscular injection.

In one specific, non-limiting example, the polyomavirus capsid polypeptide is administered in a manner to direct the immune response to a cellular response (that is, a helper T cell or cytotoxic T lymphocyte (CTL) response), rather than a humoral (antibody) response.

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle, (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 4-1 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 4-1 BBL, and/or ICAM-1 are administered.

A pharmaceutical composition including one or more polyomavirus capsid polypeptide is thus provided. These compositions are of use to promote an immune response to polyomavirus, such as a BKV serotype-specific response. In some examples, the disclosed compositions include a BKV-IV capsid polypeptide (or a fragment thereof), a BKV-I capsid polypeptide (or a fragment thereof), and a pharmaceutically acceptable carrier. In particular examples, the compositions include a VLP including at least one BKV-IV capsid polypeptide, a VLP including at least one BKV-I capsid polypeptide, and a pharmaceutically acceptable carrier. In other examples, the composition includes a VLP including at least one BKV-Ia capsid polypeptide, a VLP including at least one BKV-Ib2 capsid polypeptide, a VLP including at least one BKV-IV capsid polypeptide, and a pharmaceutically acceptable carrier. In some examples, the compositions further include at least one BKV-II capsid polypeptide, at least one BKV-III capsid polypeptide and/or at least one JCV capsid polypeptide (such as one or more VLPs including at least one BKV-II capsid polypeptide, at least one BKV-III capsid polypeptide, and/or at least one JCV capsid polypeptide). In some embodiments, the compositions include one or more adjuvants.

In one embodiment, the polyomavirus capsid polypeptide is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate 80 (TWEEN® 80 surfactant) (Sorbitan-mono-9-octadecenoate-poly(oxy-1,2-ethanediyl; manufactured by ICI Americas, Wilmington, Del.), TWEEN® 40 surfactant, TWEEN® 20 surfactant, TWEEN® 60 surfactant, ZWITTERGENT® 3-12 detergent, TEEPOL® HB7 detergent, and SPAN® 85 detergent. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977; and Hunter et al., *J. Immunol.* 127:1244-1250, 1981; for example, PLURONIC® L62LF, L101, and L64 surfactants, PEG1000, and TETRONIC® 1501, 150R1, 701, 901, 1301, and 130R1 surfactants. The chemical structures of such agents are well known in the art. In one embodiment, the agent is chosen to have a hydrophile-lipophile balance (HLB) of between 0 and 2, as defined by Hunter and Bennett, *J. Immunol.* 133:3167-3175, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, squalane, eicosane, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

In one embodiment, the adjuvant is a mixture of stabilizing detergents, micelle-forming agent, and oil available under the name PROVAX® adjuvant (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding a polyomavirus capsid polypeptide or fragment thereof (for example, a BKV or JCV capsid polypeptide or fragment). A therapeutically effective amount of the BKV or JCV capsid polynucleotide can be administered to a subject in order to generate an immune response.

One approach to administration of nucleic acids is direct immunization with plasmid DNA, such as with a mammalian expression plasmid. For example, the nucleotide sequence encoding a polyomavirus capsid polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOM® antigen delivery system (negatively charged cage-like structures of 30-40 nm in size formed spontaneously on mixing cholesterol and saponin). Protective immunity has been generated in a variety of experimental models of infection, including toxoplasmosis and Epstein-Barr virus-induced tumors, using ISCOM® antigen delivery system as the delivery vehicle for antigens (Mowat and Donachie, *Immunol. Today* 12:383, 1991). Doses of antigen as low as 1 μg encapsulated in ISCOM® antigen delivery system have been found to produce Class I mediated CTL responses (Takahashi et al., *Nature* 344:873, 1990).

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 4-1 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the BKV polypeptide coding sequence, or the nucleic acid can be cloned into one or more separate vectors for co-administration.

In one embodiment, a nucleic acid encoding a polyomavirus capsid polypeptide is introduced directly into cells. For example, the nucleic acid can be loaded onto gold microspheres by standard methods and introduced into the skin by a device such as the Helios® Gene Gun system (Bio-Rad, Hercules, Calif.). The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 μg to 100 mg of immunogenic polyomavirus capsid polypeptide (or fragment thereof) per patient per day. Dosages from 0.1 to about 100 mg per patient per day (for example, about 10 mg to 50 mg) can be used, particularly if the agent is administered to a secluded site and not into the circulatory or lymph system, such as into a body cavity or into a lumen of an organ. In other non-limiting examples, the pharmaceutical composition includes one or more VLPs including the disclosed polyomavirus capsid polypeptides, for example about 1-200 μg VLP (such as about 10 μg to 200 μg, about 20 μg to 100 μg, or about 20 μg to about 40 μg).

In some examples, the compositions include pharmaceutically acceptable carriers and/or one or more adjuvants. Actual methods for preparing administrable compositions will be known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, Pa., 21$^{st}$ Edition (2005).

The administration of the polyomavirus capsid polypeptides (or fragments thereof), VLPs including the polypeptides, or nucleic acids encoding the polypeptides can be sequential, simultaneous (concurrent), or substantially simultaneous. Sequential administration can be separated by any amount of time, so long as the desired effect is achieved. In some examples a BKV-I capsid polypeptide or fragment thereof and a BKV-IV capsid polypeptide or fragment thereof are administered to a subject sequentially. In other examples, a BKV-I capsid polypeptide or fragment thereof and a BKV-IV capsid polypeptide or fragment thereof are administered to a subject simultaneously or substantially simultaneously.

In some examples, the effectiveness of the therapeutic or preventive intervention is monitored by titering the BKV or JCV neutralizing potential of the subject's serum antibody responses over time. Subjects who are found to have been poorly responsive to initial therapeutic interventions, such as but not limited to immunization with BKV or JCV capsid proteins, are given one or more booster doses of the therapeutic intervention.

Multiple administrations of the compositions described herein are also contemplated. Single or multiple administrations of the compositions are administered, depending on the dosage and frequency as required and tolerated by the subject. In one embodiment, the dosage is administered once as a bolus, but in another embodiment can be applied periodically until a therapeutic result is achieved. In one embodiment, the dose is sufficient to treat or ameliorate symptoms or signs of BKV and/or JCV without producing unacceptable toxicity to the subject. In another embodiment, the dose is sufficient to inhibit infection with BKV upon subsequent exposure to BKV. In other embodiments, the dose is sufficient to inhibit infection with JCV upon subsequent exposure to JCV. In a further embodiment, the dose is sufficient to inhibit a symptom of BKV in a subject with a latent BKV infection. In another embodiment, the dose is sufficient to inhibit a symptom of JCV in a subject with a latent JCV infection. Systemic or local administration can be utilized.

VI. Methods of Monitoring Immune Response to Polyomavirus

Also disclosed herein are methods of monitoring an immune response to polyomavirus, for example, following exposure (or potential exposure) to polyomavirus or following immunization against polyomavirus. In some examples, the methods include detecting the presence of polyomavirus antibodies in a subject that has been administered an immunogenic composition comprising at least one isolated BKV capsid polypeptide (or fragment thereof) or a nucleic acid encoding a BKV capsid polypeptide. In other examples, the methods include detecting the presence of polyomavirus antibodies in a subject that has been administered an immunogenic composition comprising at least one isolated JCV capsid polypeptide (or fragment thereof) or a nucleic acid encoding a JCV capsid polypeptide.

In some examples, the method includes detecting the presence of polyomavirus antibodies (such as neutralizing antibodies) in a sample from a subject (such as a blood sample or serum sample). The polyomavirus antibodies include one or more of BKV-I antibodies (such as BKV-Ia antibodies, BKV-Ib2 antibodies, and/or BKV-Ic antibodies), BKV-II antibodies, BKV-III antibodies, BKV-IV antibodies (such as BKV-IVb1 antibodies and/or BKV-IVc2 antibodies), or JCV antibodies. In some examples, the antibodies are neutralizing antibodies. In some non-limiting examples, the antibodies are BKV-Ia neutralizing antibodies, BKV-Ib2 neutralizing antibodies, or BKV-IV neutralizing antibodies. Monitoring immune response to polyomavirus can indicate whether a subject has developed an immune response (for example, a protective immune response) to one or more polyomaviruses, for example, following administration of an immunogenic composition (for example, as described above). Monitoring immune response to polyomavirus can also indicate whether a subject has seroconverted for one or more polyomaviruses (for example, BKV-I and/or BKV-IV) following an organ transplant or immunosuppressive therapy. In some examples, multiple samples from a subject are tested for presence of antibodies over time, for example prior to and at time points after (such as 1 week, 2 weeks, 1 month, 2 months, 3 months, 6 months, 9 months, 1 year, or more after) administration of an immunogenic composition, organ transplantation or start of immunosuppressive therapy.

Methods for detecting antibodies in a sample are known to one of skill in the art. Such methods include but are not limited to ELISA, immunofluorescence assay, radioimmunoas say, and micro-agglutination test. In some examples, the methods include detecting the presence of neutralizing antibodies (such as BKV serotype-specific neutralizing antibodies) in a sample from a subject. In some examples, assays for detecting neutralizing antibodies include plaque reduction neutralization test, cell killing, and reporter assays.

In a particular example, neutralizing antibodies are detected using a reporter assay. BKV or JCV reporter vectors (also known as pseudovirions) are produced by packaging a reporter plasmid in cells (such as 293 cells, for example 293TT cells or 293FT cells for BKV or SVG cells for JCV) expressing a BKV (such as BKV-I, BKV-II, BKV-III, or BKV-IV) or JCV capsid polypeptide (for example, VP1, VP2, and/or VP3). The reporter vector particles are then isolated and treated with serial dilutions of serum from a subject (such as a series of four-fold dilutions from 1:100 to $1{:}2.6\times10^7$ or a series of 10-fold dilutions from 1:100 to $1\times10^7$). The serum/reporter vector mixture is then applied to fresh cells (for example 293 cells for BKV or SVG cells for JCV) for a period of time (such as 72 hours). The cell culture is then assayed for production of a reporter protein encoded by the reporter plasmid packaged within the reporter vector. A decrease in reporter vector activity (for example, as compared to a control, such as a no serum control) indicates the presence of neutralizing antibodies in the sample. In one example, the reporter plasmid carries an SV40 origin of replication, which can mediate replicative amplification of the transduced plasmid in the target cell. In a specific example, the reporter vector is phGluc (*Gaussia princeps* luciferase under the control of a human elongation factor 1 alpha promoter) and activity is detected using *Gaussia* luciferase substrate (New England Biolabs). See, e.g., Pastrana et al., *PLoS Pathogens* 5(9):e1000578, 2009 (incorporated herein by reference). One of ordinary skill in the art can select additional reporters of use in neutralizing antibody assays, such as green fluorescent protein, β-galactosidase, alkaline phosphatase, and others.

The present disclosure is illustrated by the following non-limiting Examples.

Example 1

Materials and Methods

Mice:

Eight-week old female BALB/cAnNCr mice were immunized once subcutaneously with 5 μg of BKV-I or BKV-IV viral-like particles (VLPs) in complete Freund's Adjuvant (CFA, Sigma-Aldrich, St. Louis, Mo.). Sera were obtained 4 weeks after immunization. The animals were kept under pathogen-free conditions in compliance with institutional guidelines at the National Cancer Institute.

Sera:

Samples from 108 renal transplant subjects from the "Randomized Prospective Controlled Clinical and Pharmacoeconomic Study of Cyclosporine vs. Tacrolimus in Adult Renal Transplant Recipients" of the Washington University, School of Medicine were used. The patients and clinical protocols from the study have previously been described in detail (Bohl et al., *Am. J. Transplant.* 5:2213-2221; Randhawa et al., *Clin. Vaccine Immunol.* 15:1564-1571, 2008). Patients were given an immunosuppressive regimen, which was discontinued if viremia was detected. Serum samples were collected at roughly 1, 4, 12, 26 and 52 weeks post-transplantation. None of the patients were observed to suffer from PVAN during the course of the collection period. Sera from healthy subjects visiting U.S. plasma donation centers have been described in detail before (Pastrana et al., *PLoS Pathog.* 5:e1000578, 2009).

VLPs and Reporter Vectors (Pseudovirions):

BKV reporter vectors were generated as previously described (Pastrana et al., *PLoS Pathog.* 5:e1000578, 2009). BKV-I reporter vectors were produced using plasmid pCAG-BKV (Nakanishi et al., *Virology* 379:110-117, 2008), which encodes the capsid proteins of BKV isolate KOM-5 (SEQ ID NOs: 1-3). KOM-5 is classified as a BKV type I subtype b-1 (Ib-1) genotype (Nishimoto et al., *J. Mol. Evol.* 63:341-352, 2006), and was transfected into 293TT cells (Buck et al., *J. Virol.* 78:751-757, 2004) using LIPOFECTAMINE® 2000 transfection reagent (Invitrogen, Carlsbad, Calif.). Then, 48 hours after transfection the cells were suspended at >100 million cells/ml in Dulbecco's phosphate buffered saline (DPBS) and lysed by addition of 0.5% Triton X-100, 25 mM ammonium sulfate (diluted from a 1M stock adjusted to pH 9) and RNase A/T1cocktail (Ambion, Austin, Tex.). The lysate was incubated at 37° C. overnight to allow capsid maturation, then clarified by spinning twice for 10 minutes at 5,000×g, with gentle agitation of the lysate between spins. Reporter vector particles were purified out of the clarified supernatant through a 27-33-39% iodixanol (OPTIPREP® density gradient medium, Sigma-Aldrich, St. Louis, Mo.) step gradient (Buck and Thompson, *Curr. Protoc. Cell Biol. Chapter* 26, Unit 26.21, 2007).

For BKV-IV particles the sequence of BKV isolate A-66H (subtype IV-c2; Zhong et al., *J. Gen. Virol.* 90:144-152, 2009) was used to design synthetic codon-modified versions of the VP1, VP2 and VP3 genes (SEQ ID NOs: 39-41). The codon-modified genes were synthesized by Blue Heron Biotechnology (Bothell, Wash.) and cloned into Gateway (Invitrogen) adapted mammalian expression plasmids pGwf (for VP1) or phGf (for VP2 and VP3) (Buck et al., *Proc. Natl. Acad. Sci. USA* 103:1516-1521, 2006). An additional pair of plasmids, pwB2b and pwB3b, were generated by transferring the BKV-IV VP2 or VP3 (respectively) gene into the SV40 promoter-driven expression cassette of pwB. For BKV-IV reporter vector production, cells were co-transfected with pwB2b, pwB3b, ph2b, ph3b and phGluc at a 2:2:1:1:1 ratio. Initial particle stocks produced without ph2b or ph3b in the co-transfection mixture appeared to show poor VP2/3 occupancy and relatively poor infectivity. Transfection, harvesting and purification of BKV-IV reporter vectors were the same as for production of BKV-I reporter vectors.

For generation of VLPs, 293TT cells were transfected with pCAG-BKV (BKV-I) or a mixture of pwB2b and pwB3b (BKV-IV) without any reporter plasmid. Two days after transfection, the cells were lysed with 0.5% Triton X-100 in DPBS supplemented with 25 mM ammonium sulfate, BENZONASE® nuclease (Sigma-Aldrich), PLASMID-SAFE™ nuclease (Epicentre, Madison, Wis.), and 1.2 U/ml neuraminidase V (Sigma-Aldrich, Catalog No. N2876). The lysates were incubated at 37° C. overnight, then adjusted to 0.85 M NaCl, clarified as above, and subjected to purification over OPTIPREP® density medium gradients.

ELISAs:

IMMULON® H2B microtiter plates (Thermo Fisher Scientific, Waltham, Mass.) were coated with 15 ng/well of VLPs in PBS overnight. PBS with 1% non-fat dry milk (blotto) was used to block the coated plates for 2 hours at room temperature, with orbital rotation. Sera from mice and healthy human subjects were serially diluted in blotto and incubated on blocked plates at room temperature for 1 hour, with orbital rotation. Washing was performed with PBS. Horseradish peroxidase conjugated goat anti-mouse IgG (BioRad) or donkey anti-human IgG (Jackson ImmunoResearch, Wes Grove, Pa.) diluted 1:7500 in blotto was used to detect bound sera. The plates were incubated with ABTS (2,2-azino-di-[3-ethylbenzthiazoine sulfonate) substrate (Roche Applied Science, Indianapolis, Ind.) and absorbance read at 405 nm with a reference read at 490 nm. The effective concentration 10% ($EC_{10}$) was calculated using PRISM® software (GraphPad Software, La Jolla, Calif.) to fit a curve to the OD values for each serially-diluted serum sample. The top of each response curve was constrained based on the average of the calculated plateau maximum (Bmax) values for strongly reactive sera. The Bmax value was typically an OD value of around 2.0, such that the $EC_{10}$ value can be considered comparable to an OD cutoff value of 0.2.

Neutralization Assays:

Neutralization assays were performed as previously reported (Pastrana et al., *PLoS Pathog.* 5:e1000578, 2009). Briefly, 293TT cells were seeded at a density of $3\times10^4$ cells per well and allowed to attach for 3-5 hours. Sera from mice and human subjects were serially diluted, and sera from renal transplant patients were tested in separate assays at 4 different dilutions: 1:100, 1:500, 1:5,000, and 1:50,000. Dilutions were performed in cell culture medium (DMEM without phenol red supplemented with 25 mM HEPES, 10% heat-inactivated fetal bovine serum, 1% MEM non-essential amino acids, 1% GLUTAMAX™ supplement and 1% antibiotic-antimycotic, all from Invitrogen). Then 24 μl of diluted sera were mixed with 96 μl of diluted reporter vector stock and placed at 4° C. for 1 hour. Cells were incubated with 100 μl of this mixture for 72 hours. Conditioned supernatants (25 μl) were harvested into white 96-well luminometry plates (Perkin Elmer, Waltham, Mass.). *Gaussia* Luciferase Assay Kit substrate (50 μl, New England Biolabs, Ipswich, Mass.) was injected immediately prior to luminometry using a BMG Labtech POLARSTAR® Optima microplate reader.

For mice and sera from healthy individuals, 50% neutralizing titers ($EC_{50}$) were calculated based on dose-response curves with top and bottom values constrained to the average values of "no serum" and "no reporter vector" control wells, respectively. For transplant patients, the following criteria for seropositivity and seronegativity were adopted: sera were considered negative at entry if the 1:100 dilution did not mediate at least a 95% reduction in *Gaussia luciferase* activity (measured in relative light units, RLUs) relative to the no serum control condition (>95% neutralization of the reporter vector). Seroconversion refers to subjects who scored seronegative at the initial time point but whose sera were >95% neutralizing at the 1:500 dilution at any subsequent time point. A stricter definition of seroconversion, accounting for the possible low level cross-type neutralization, added the stipulation that the 95% neutralizing titer for BKV-IV differed from the BKV-I neutralizing titer by less than 1,000 fold.

Sequence Analysis:

VP1 sequences from BKV strains indicated in Table 3 (below) were downloaded from GenBank (Pastrana et al., *PLoS Pathogens* 8:e1002650, 2012; incorporated herein by reference in its entirety). ClustalW alignments were performed with MACVECTOR™ software version 11.1.2 using a Gonnet series matrix. Structural modeling of BKV VP1 amino acid variations was performed by aligning the sequences of JCV or SV40 VP1 to BKV, followed by inspection of homologous positions of interest in the JCV or SV40 VP1 X-ray crystal structures (PDB ID accession numbers 3NXD and 1SVA, respectively). Structure inspections were performed using Swiss PDB Viewer.

Example 2

BKV Cross-Neutralizing Responses in Mouse Sera

This example describes serological cross-reactivity in mice immunized with VLPs from BKV-I or BKV-IV serotypes.

Figure 1:
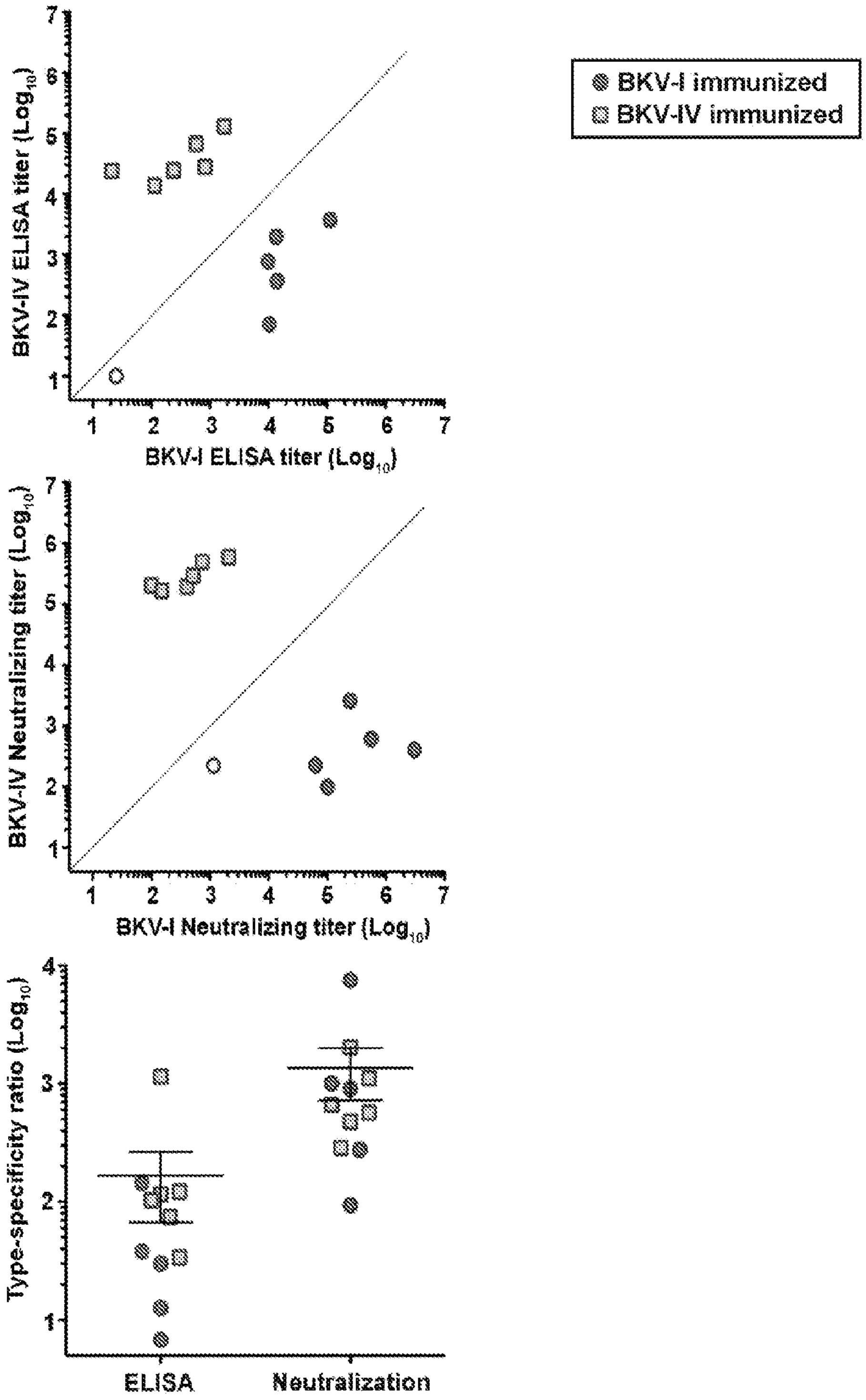
FIG. 1 is a series of graphs showing ELISA and neutralizing antibody titers in mice immunized with virus-like particles (VLPs) formed by expression of recombinant VP1 capsid proteins derived from BKV-I isolate KOM-5 (subtype BKV-Ib1) or BKV-IV isolate A-66H (subtype BKV-IVc2). Six mice were immunized with BKV-I (circles) or BKV-IV (squares) VLPs. In the top panel, sera were titered using separate BKV-I (x axis) or BKV-IV (y axis) VLP ELISAs. A data point from one relatively non-responsive animal is shown as an open circle. The middle panel depicts BKV genotype-specific neutralizing titers for the same set of mice. The bottom panel shows the ratio of the neutralizing titer for the BKV genotype administered as a vaccine versus the neutralizing titer for the heterologous BKV genotype for individual animals. The non-responsive animal was excluded from the analysis in the bottom panel. In the top and middle panels, the diagonal line shows a theoretical 1:1 correlation between BKV-I and BKV-IV titers.

To determine if reactivity to one BKV type would generate cross-reactive antibodies, mice were immunized with VLPs containing the VP1, VP2, and VP3 capsid proteins from the two most common serotypes: BKV-I (BKV-Ib1 isolate KOM-5) or BKV-IV (BKV-IVc2 isolate A-66H). A single sub-cutaneous dose in the presence of Freund's adjuvant resulted in the development of high-titer responses. As measured by ELISA, all mice but one responded with titers against BKV-I ranging from 9000 to 110,000 (FIG. 1, top panel). The response in BKV-IV immunized mice was similar, with titers ranging from 13,000 to 130,000. The sera exhibited varying amounts of cross-reactivity against the non-cognate BKV. The average ratio of homologous to heterologous titer was 21 for mice immunized with BKV-I and 110 for mice immunized with BKV-IV (FIG. 1, bottom panel). For this calculation the non-responsive mouse was eliminated, as the denominator was not a true titer, but arbitrarily set at 25, or the lowest concentration tested.

Figure 2:
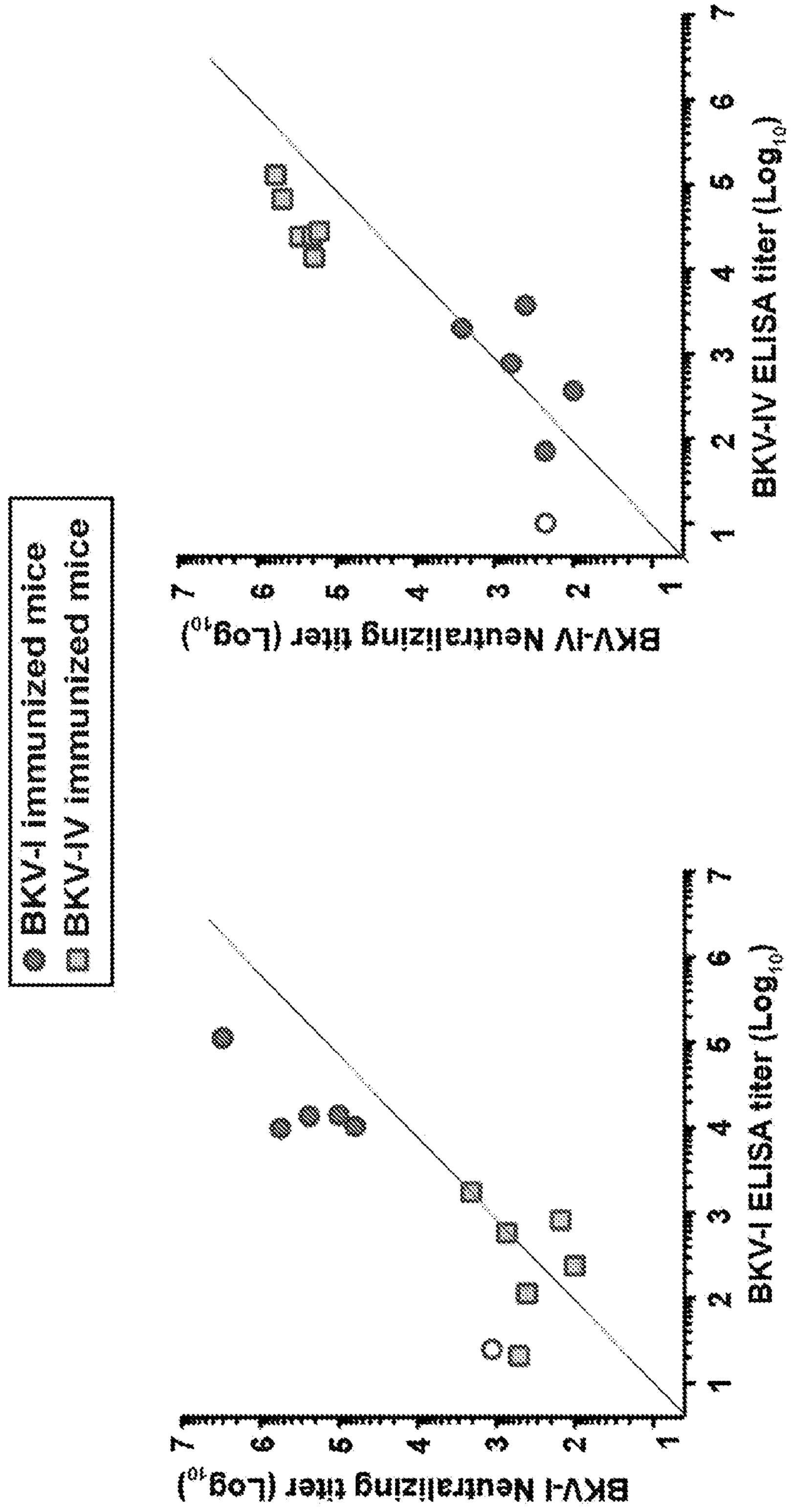
FIG. 2 is a series of graphs showing BKV-I and BKV-IV ELISA versus neutralizing titers in VLP immunized mice. ELISA (x axis) or neutralizing titers (y axis) for six BKV-I (circles) or BKV-IV (squares) VLP immunized mice are shown. Neutralizing titers against the BKV-I pseudovirus are shown in the left panel and anti-BKV-IV titers are shown in the right panel. A data point from the relatively non-responsive animal (FIG. 1) is shown as an open circle.

In order to obtain more information on the cross-neutralizing responses, a reporter-vector based neutralizing assay was also utilized. These recombinant production systems made it possible to generate infectious capsids composed of the VP1/2/3 capsid proteins of BKV primary isolates of genotypes I and IV that are not otherwise culturable. Using the reporter-based assays, the neutralizing potency of sera from BKV-I or BKV-IV vaccinated mice were titered. The neutralizing assay BKV-I, when compared to ELISAs, has been shown to have a broader linear range for detection of serum titers (Pastrana et al., *PLoS Pathog.* 5:e1000578, 2009), and a similar neutralization assay has also shown improved specificity in the context of papillomaviruses (Pastrana et al., *Virology* 321:205-216, 2004). The neutralization assays showed a significantly greater degree of BKV type-specificity compared to the ELISAs. For BKV-I immunized mice, homologous titers ranged from 1100 to 3,000,000 (FIG. 1, middle panel). The mouse that was non-reactive by ELISA showed a titer, of 1100, which was 55-fold lower than the next mouse with lower BKV-I titers. Mice immunized with BKV-IV had titers ranging from 17,000 to 600,000. The ratio of homologous to heterologous titer was 910 for mice immunized with BKV-I and 620 for mice immunized with BKV-IV. A comparison of ELISA values to neutralization assay values is shown in FIG. 2.

To test the possibility that a booster vaccination might alter the degree of cross-neutralization of the two BKV types, a second dose of cognate VLPs was administered to the mice (in incomplete Freund's adjuvant) one month after priming. Repeat serology was performed a total of two months after the initial priming dose. Hyperimmune sera from the boosted animals showed neutralizing ratios similar to the initial testing.

In addition, mice vaccinated with VLPs based on BKV-Ib2 had serum antibody responses that robustly neutralized the cognate BKV-Ib2 reporter pseudovirus but failed to effectively neutralize the BKC-Ia pseudovirus (Table 2). This result confirms that genotypes BKV-Ia and BKV-Ib2 are distinct serotypes.

TABLE 2

Single immunization of mice with BKV variants

| | | Neutralizing titer (log) | | | | | | |
|---|---|---|---|---|---|---|---|---|
| | | Ia | Ib2 | Ic | II | III | IVb1 | IVc2 |
| IMMUNIZATION | Ia | 6.6 | 3.9 | 3.6 | 2.7 | neg | 2.6 | 2.0 |
| | Ib2 | neg | 4.5 | 3.6 | neg | neg | 2.3 | neg |
| | Ic | 3.7 | 3.6 | 4.2 | neg | neg | 2.8 | neg |
| | II | 2.1 | 3.5 | 3.2 | 4.5 | 3.5 | 3.6 | 3.1 |
| | III | neg | 3.5 | 3.3 | 3.4 | 4.0 | 2.9 | 2.9 |
| | IVb1 | neg | 2.9 | 3.1 | 2.5 | neg | 4.6 | 4.1 |
| | IVc2 | neg | 3.4 | 3.5 | 3.0 | 2.2 | 3.8 | 4.2 |
| | All 7 types | 4.0 | 3.9 | 4.1 | 4.6 | 4.0 | 4.7 | 4.7 |

Taken together, the data suggest that the neutralization assay has a larger quantitative dynamic range than ELISA and the neutralization assay is on average about 10 times better at distinguishing BKV type-specific titers (FIG. 1, bottom panel). It is possible that non-neutralizing cross-reactive anti-BKV antibodies are being detected in the ELISA assay but not in the neutralization assay. However, in the context of kidney transplantation, detection of type-specific neutralizing antibodies is more relevant, as only neutralizing antibodies would inhibit de novo infections with a new serotype or suppress latent infections with an existing BKV serotype.

Example 3

BKV Titers in Healthy Adults

Sera from 48 healthy adults with a median age of 52.5 years were assessed for reactivity to BKV-I and BKV-IV in ELISAs. Seroprevalence of different BKV types in these individuals is shown in Table 3. Of these, 83% were seropositive for BKV-I (FIG. 3, top panel), a figure similar to what has been reported in the literature (Egli et al., *J. Infect. Dis.* 199:837-846, 2009; Knowles et al., *J. Med. Virol.* 71:115-123, 2003). The geometric mean titer for anti-BKV-I sera was 550 and it ranged from a low of 60 to a high of 7100. In contrast, 65% of volunteers were seropositive for BKV-IV, but their geometric mean titer was only 150, even when they had a similar range (60 to 17,000). In the BKV-IV ELISA, only 18% (9 sera) had a titer higher or equal to 500, while in the BKV-I ELISA 54% (26 sera) reached this titer. There was also a statistically significant correlation between BKV-I and BKV-IV titers (Spearman r=0.69, p<0.0001). This correlation, along with the lower geometric mean titers and the knowledge that previous studies have only found 6-7% prevalence of BKV-IV DNA (Krumbholz et al., *J. Med. Virol.* 78:1588-1598, 2006), indicates that much of the BKV-IV seropositivity is attributable to cross-reactivity in the ELISA assay. The sera were therefore evaluated in the neutralization assay.

TABLE 3

Seroprevalence of BKV types in 48 healthy individuals

| | Ia | Ib2 | Ic | II | III | IVb1 | IVc2 |
|---|---|---|---|---|---|---|---|
| % Prevalence | 79 | 52 | 63 | 58 | 28 | 17 | 28 |

Figure 3:
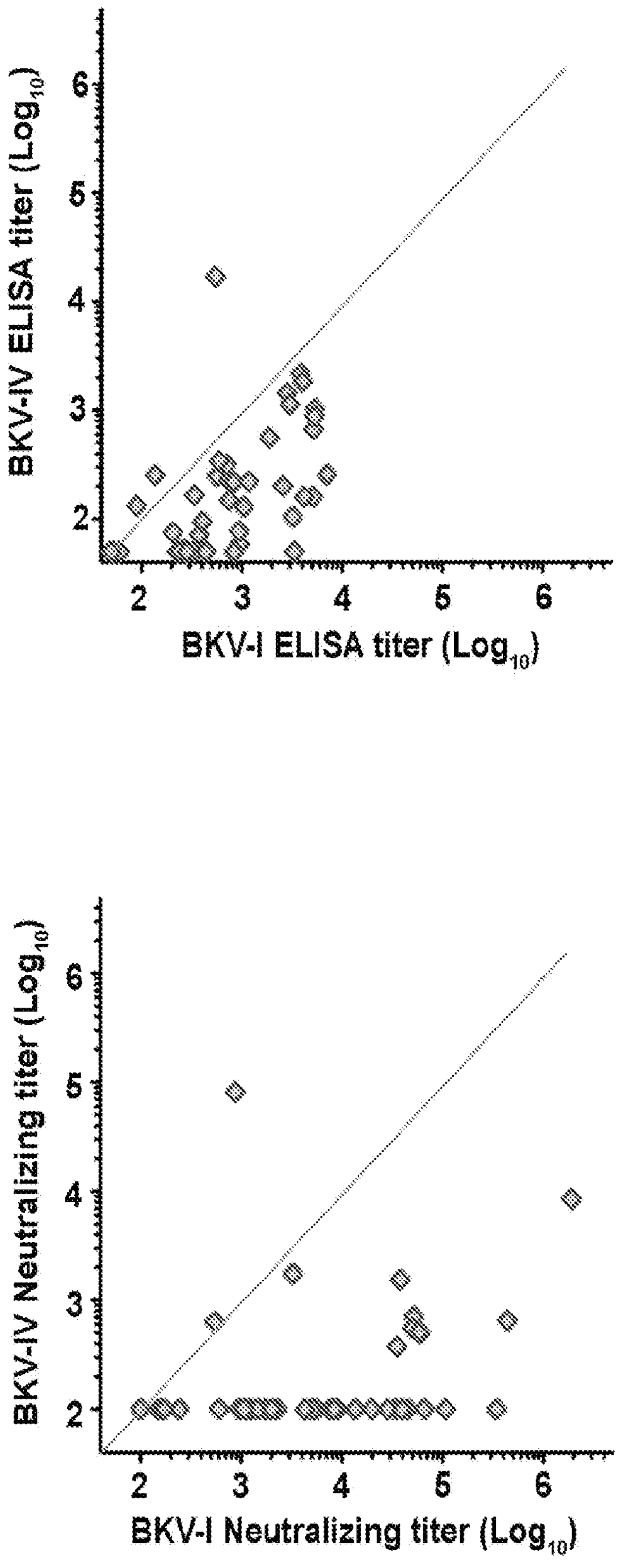
FIG. 3 is a pair of graphs showing BKV-I and BKV-IV serological titers in healthy adults. Sera from 48 healthy adults were evaluated for BKV type-specific serological titers. The upper panel shows BKV-I and BKV-IV titers evaluated by ELISA. The lower panel shows neutralizing titers. The diagonal line shows a theoretical 1:1 correlation between BKV-I and BKV-IV titers.
Figure 4:
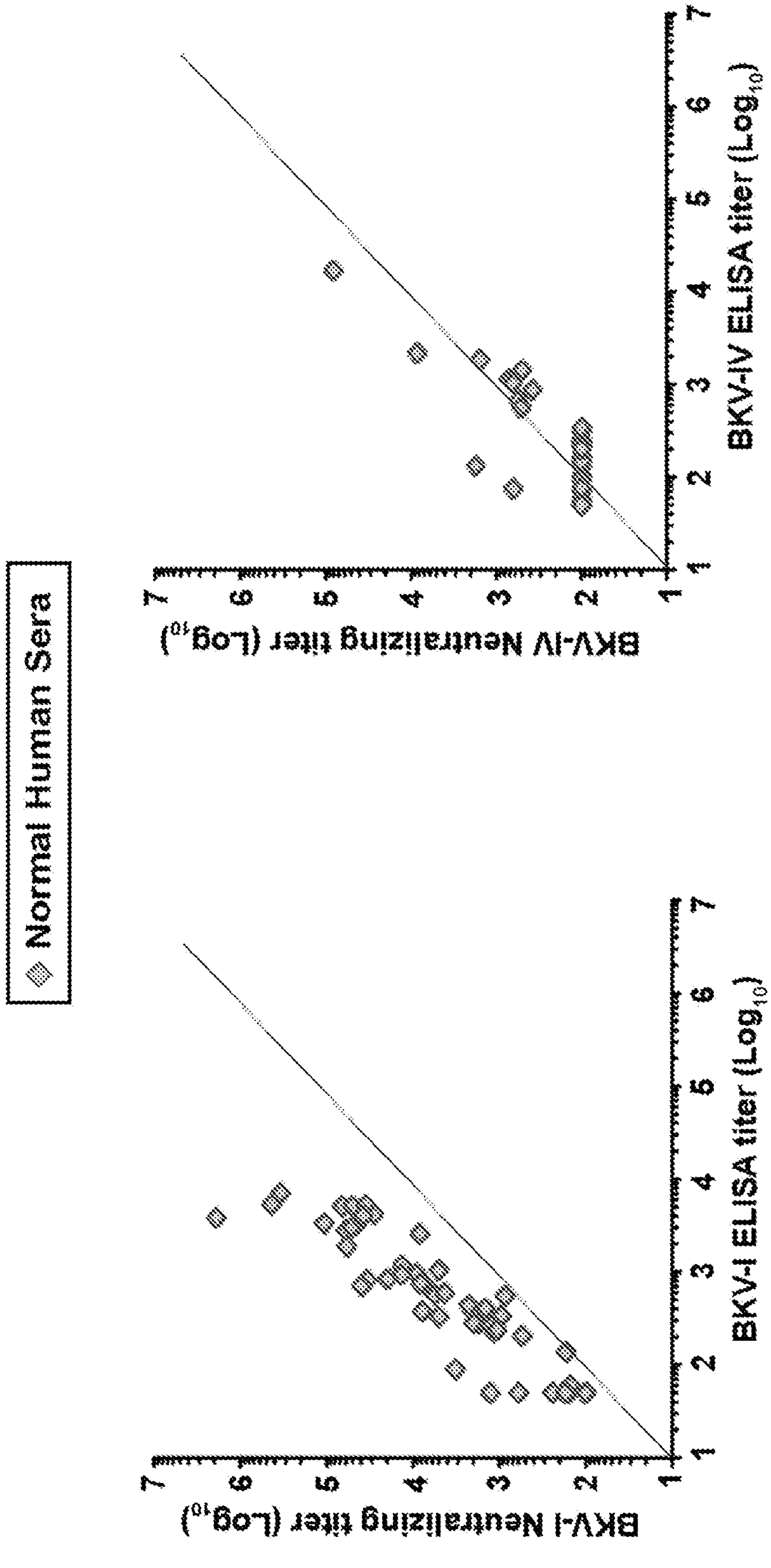
FIG. 4 is a series of graphs showing BKV-I and BKV-IV ELISA versus neutralizing titers in healthy adults. ELISA (x axis) or neutralizing titers (y axis) for BKV-I (circles) or BKV-IV (squares) are shown. Neutralizing titers against the BKV-I pseudovirus are shown in the left panel and anti-BKV-IV titers are shown in the right panel.

For the neutralization assays, serum samples were serially diluted starting at 1:100. This is the lowest naïve (rabbit) serum dilution that is consistently devoid of non-specific neutralizing activity (Pastrana et al., *PLoS Pathog.* 5:e1000578, 2009). Therefore $EC_{50}$ values below this dilution could not be accurately calculated and were arbitrarily designated to have an $EC_{50}$ of 100. Only 3 volunteers (6%) were negative for BKV-I neutralization. In contrast, 37 (77%) were negative for BKV-IV (FIG. 3, bottom panel). The geometric mean $EC_{50}$ titers for BKV-I were also significantly higher (5100) than BKV-IV titers (180). There were three individuals with titers of more than 60,000 for BKV-I that were completely negative for BKV-IV neutralization. In contrast to the ELISA results, there was not a statistically significant correlation between the subjects' BKV-I and BKV-IV neutralizing titers. There were two individuals with BKV-I neutralizing titers of >100,000 whose sera did not detectably neutralize BKV-IV at the lowest tested dilution (1:100). This indicates that these individuals displayed BKV type specificity ratios of at least 1,000. A comparison of ELISA values to neutralization assay values is shown in FIG. 4. Overall, the results for the human sera confirm the observations using murine sera, suggesting that the neutralization assays offer a significantly greater degree of sensitivity and specificity for serological analysis of exposure to BKV-I and BKV-IV.

Example 4

BKV Type-Specific Seroconversion in Kidney Transplant Recipients

The anti-BKV-I and BKV-IV titers of 108 kidney transplant recipients were determined. An archived set of sera collected at time points of roughly 1, 4, 12, 26, and 52 weeks post-transplantation were tested in the neutralization assay. Each sample was tested at four dilutions: 100, 500, 5,000, and 50,000. Because of this lack of full serial dilution, a more stringent neutralization cutoff of 95% for individual data points was utilized. Neutralization assay results for individual subjects are shown in FIGS. 5 and 6. At entry, 5 patients (5%) were seronegative (<95% neutralizing at the 1:100 serum dilution) in the BKV-I neutralization assay (Table 4). In contrast, there were 53 initially BKV-IV seronegative subjects (49%). The patients were then assessed for seroconversion, defined as a change from seronegative at the first time point to at least 95% neutralization at the 1:500 serum dilution at any subsequent time point. All of the 5 initially seronegative BKV-I patients seroconverted for BKV-I, and 23 (43%) of the initially BKV-IV seronegative patients seroconverted for BKV-IV (Table 4).

TABLE 4

Seroconversion of kidney transplant recipients

| Negative at entry (% total) | | Seroconversion (% initial negative) | | Stringent Seroconversion (% initial negative) | |
|---|---|---|---|---|---|
| BKV-I | BKV-IV | BKV-I | BKV-IV | BKV-I | BKV-IV |
| 5 (5%) | 53 (49%) | 5 (100%) | 23 (43%) | 5 (100%) | 12 (23%) |

The average BKV type-specificity ratio for sera from immunized mice was 1359 (FIG. 1). Two human subjects likewise showed type-specificity ratios >1000 (FIG. 3). To address the possibility that BKV-IV neutralization might be partly attributable to cross-reactivity of high titer antibody responses elicited by BKV-I, a more stringent definition of seroconversion was applied, in which the ratio of the BKV-I titer versus the BKV-IV titer (or vice-versa) must be less than 1000 at least one time point to be considered a clear type-specific seroconversion event. Even with these stricter criteria, 12 (23%) of the BKV-IV negative patients seroconverted within a year of transplantation (Table 2). Based on the results shown in FIGS. 1 and 3, the occurrence of BKV type-specificity ratios of 10 or less seems highly unlikely. Five patients (5%) underwent BKV-IV-specific seroconversion by the extremely strict criterion of having a BKV-I to BKV-IV titer ratio ≤10.

On average, the patients' BKV-I and BKV-IV neutralizing titers both increased substantially by one year after renal transplantation (FIG. 7). In some instances, titer increases occurred even in patients who showed moderate neutralizing antibody titers at study entry (FIGS. 5 and 6).

Example 5

BKV VP1 Protein Sequence Analysis

Full-length non-identical BKV VP1 peptide sequences available via GenBank were aligned (FIG. 8). The GenBank Accession numbers utilized to generate the alignment are provided in Table 5. Because it is not possible to distinguish between Ia and Ib1 subtypes based on VP1 amino acid sequences, BKV-Ia indicates genotypes Ia/Ib1 and BKV-Ib indicates genotype Ib2. It is also not possible to distinguish between BKV-IV subtypes based on VP1 amino acid sequences. Therefore, BKV-IV indicates genotypes IV-b1/IV-c2.

TABLE 5

GenBank Accession numbers of aligned BKV VP1 sequences

| BKV type | GenBank Accession Number | SEQ ID NO: |
|---|---|---|
| Ia | BAE96059 | 52 |
| Ia | CAA40239 | 53 |
| Ia | BAF02957 | 54 |
| Ia | AAT47395 | 55 |
| Ia | AAT47401 | 56 |
| Ia | BAF42979 | 57 |
| Ia | ABI94689 | 58 |
| Ia | ABI94671 | 59 |
| Ia | AAT47365 | 60 |
| Ia | AAT47389 | 61 |
| Ia | YP_717939 | 62 |
| Ia | AAT47371 | 63 |
| Ia | CAA24307 | 64 |
| Ia | AAT47413 | 65 |
| Ia | AAT47419 | 66 |
| Ia | BAF42937 | 67 |
| Ia | ABI94725 | 68 |
| Ia | AFA41877 | 69 |
| Ia | AFA41907 | 70 |
| Ia | AAT47425 | 71 |
| Ia | AAT47431 | 72 |
| Ia | CAA40243 | 73 |
| Ia | AEK21505 | 74 |
| Ib | ABI94623 | 75 |
| Ib | AFA41920 | 76 |
| Ib | ABI94611 | 77 |
| Ib | BAF42907 | 78 |
| Ib | ABD04662 | 79 |
| Ib | ABI94713 | 80 |
| Ib | CBX88302 | 81 |
| Ib | AFA41880 | 82 |
| Ib | BAF93325 | 83 |
| Ib | CAA40247 | 84 |

TABLE 5-continued

GenBank Accession numbers of aligned BKV VP1 sequences

| BKV type | GenBank Accession Number | SEQ ID NO: |
|---|---|---|
| Ib | CBX88314 | 85 |
| Ib | ABI94617 | 86 |
| Ib | BAF93319 | 87 |
| Ib | AAT47347 | 88 |
| Ib | BAF93283 | 89 |
| Ib | BAF03085 | 90 |
| Ib | AFA41909 | 91 |
| Ib | BAF03097 | 92 |
| Ib | ABI94695 | 93 |
| Ic | BAE53660 | 94 |
| Ic | BAE53648 | 95 |
| Ic | CAA40235 | 96 |
| Ic | BAI43588 | 97 |
| Ic | BAE53642 | 98 |
| Ic | BAG75361 | 99 |
| Ic | BAG75283 | 100 |
| Ic | BAF76196 | 101 |
| Ic | ABI94635 | 102 |
| Ic | BAF02975 | 103 |
| II | BAF42901 | 104 |
| II | BAF42925 | 105 |
| II | CAA79596 | 106 |
| III | BAF03017 | 107 |
| III | P14996 | 108 |
| III | AEO89615 | 109 |
| IV | BAF03115 | 110 |
| IV | BAE53654 | 111 |
| IV | BAF75138 | 112 |
| IV | BAE96077 | 113 |
| IV | BAG75277 | 114 |
| IV | BAF75102 | 115 |
| IV | BAF03029 | 116 |
| IV | BAF75180 | 117 |
| IV | AFA41889 | 118 |
| IV | BAF75096 | 119 |
| IV | BAF75114 | 120 |
| IV | AFA41881 | 121 |
| IV | AFA41883 | 122 |
| IV | AFA41885 | 123 |
| IV | BAG84476 | 124 |
| IV | BAF03035 | 125 |

With respect to the BIKV-I consensus. BKV-IV isolates tend to carry a variety of substitutions: E61N, N62D, F66Y, K69R, S71T, N74T, D75A, S77D, E82D, Q117K, H139N, 1178V, F225Y, A284P, R340Q, K353R, and L362V. Mapping of these BKV-I/BKV-IV variant residues onto homologous positions in the X-ray crystal structures of JCV (Neu et al., *Cell Host Microbe* 8:309-319, 2010) and SV40 (Stehle et al., *Structure* 4:165-182, 1996) suggested that, with the exception of positions 117, 225, 284, and 340, each of these BKV-I/BKV-IV variant residues is likely to be exposed on the exterior surface of the capsid. With the exception of residues 353 and 362, which are exposed along the floor of the canyons between capsomer knobs, all the exposed variations map to sites on the apical surface and apical rim of the capsomer knob, Many of the variations are adjacent to residues predicted to be involved in binding the cellular glycolipids that serve as receptors during BKV infectious entry (Dugan et al, *J. Virol.* 81:11798-11808, 2007; Low et al., *J. Virol.* 80:1361-1366, 2006). This is consistent with the idea that BKV-I/BKV-IV variations may alter epitopes recognized by antibodies that neutralize infectivity via steric occlusion of the receptor binding site.

In addition to the differences between BKV-I and BKV-IV, several positions differ stereotypically among BKV-I subtypes. For example, BKV subtype Ib-2 isolates tend to carry V42L, E82D, D175E, V210I, R340K, and L362V differences, with respect to subtypes Ia and Ib-1. Likewise, subtype Ic isolates frequently carry E20D, F225L, and R340K differences. Although these intra-genotype-I surface variations are chemically subtle, without being bound by theory, it is possible that the differences reflect selective pressure to escape neutralizing antibodies.

In human subjects, it was found that 6 of 48 subjects with BKV-Ia neutralizing antibodies were not able to neutralize a BKV-Ib2 isolate (including VP1 polypeptide with the amino acid sequence of SEQ ID NO: 14). Analysis of mutant pseudoviruses that are recombinant chimeras of types Ia and Ib2, identified key amino acid residues that allow the Ib2 isolate to escape from Ia-neutralizing antibody response. The variations were in the VP1 BC loop and included E73K and E82D (Ia to Ib2. variations). Several other Ib2 variants and genotype Ic BC loop variations were partially resistant to Ia-neutralizing human sera. These additional variants included E73Q, S77N, E82Q, or combinations of these variations. These results suggest that an optimal BKV vaccine should include at least BKV-Ia and BKV-Ib2 VP1 polypeptides, in order to elicit antibodies capable of neutralizing all BKV-I variants. Furthermore, validation of a candidate vaccine should include screening serum from vaccinated subjects for neutralization of multiple BKV-I subtypes (such as at least BKV-Ia and BKV-Ib2 subtypes).

Example 6

Additional BKV VP1 Polypeptides

Additional BKV serotypes may remain to be discovered and fully sequenced. GenBank accession numbers CCF70703-CCF70735 report a portion of the VP1 protein encompassing the BC and EF loops. Some of these sequences contain previously unknown variations in the BC and EF loops. In some instances, the sequence fragments are more divergent from all published BKV VP1 sequences than BKV-I is from BKV-IV (FIG. 9). Based on the an alignment of these additional sequences with BKV-Ia, BKV-Ib, BKV-Ic, BKV-II, BKV-III, BKV-IVb1, and BKV-IVc2 VP1 sequences (FIG. 10), accession numbers CCF70725 (SEQ ID NO: 154), CCF70727 (SEQ ID NO: 153), CCF70729 (SEQ ID NO: 158), and CCF70730 (SEQ ID NO: 157) appear to represent portions of distinct BKV serotypes. The GenBank Accession numbers utilized to generate the alignment are provided in Table 6. The serological distinctiveness of these recently reported sequences can be determined, for example by isolating the remainder of these VP1 sequences and using the methods described in Examples 1 and 2. Polypeptides comprising these additional BKV VP1 polypeptides can be utilized in the disclosed methods and compositions. In some cases, the disclosed methods and compositions include one or more of SEQ ID NOs: 126-158.

TABLE 6

GenBank Accession Nos. of additional partial BKV VP1 sequences

| GenBank Accession No. | SEQ ID NO: |
| --- | --- |
| CCF70703 | 126 |
| CCF70704 | 127 |
| CCF70705 | 128 |
| CCF70706 | 129 |
| CCF70707 | 130 |
| CCF70708 | 131 |
| CCF70709 | 132 |
| CCF70710 | 133 |
| CCF70711 | 134 |

TABLE 6-continued

GenBank Accession Nos. of additional partial BKV VP1 sequences

| GenBank Accession No. | SEQ ID NO: |
| --- | --- |
| CCF70712 | 135 |
| CCF70713 | 136 |
| CCF70714 | 137 |
| CCF70715 | 138 |
| CCF70716 | 139 |
| CCF70717 | 140 |
| CCF70718 | 141 |
| CCF70719 | 142 |
| CCF70720 | 143 |
| CCF70722 | 144 |
| CCF70723 | 145 |
| CCF70724 | 146 |
| CCF70726 | 147 |
| CCF70728 | 148 |
| CCF70732 | 149 |
| CCF70733 | 150 |
| CCF70734 | 151 |
| CCF70735 | 152 |
| CCF70727 | 153 |
| CCF70725 | 154 |
| CCF70731 | 155 |
| CCF70721 | 156 |
| CCF70730 | 157 |
| CCF70729 | 158 |

Example 7

Methods of Eliciting an Immune Response to BKV

This example provides exemplary methods for eliciting an immune response to one or more BKV serotypes in a subject. However, one of ordinary skill in the art will appreciate that methods that deviate from these specific methods can also be used to successfully elicit an immune response to BKV in a subject.

In particular examples, the method includes selecting a subject in need of enhanced immunity to BKV. Subjects in need of enhanced immunity to BKV include individuals who are immunocompromised and individuals who have had or are candidates for organ transplantation, for example a renal transplant or bone marrow transplant. Subjects in need of enhanced immunity to BKV also include individuals who are seronegative for at least one BKV serotype.

Subjects selected for treatment are administered a therapeutically effective amount of a disclosed immunogenic composition. In some examples, a therapeutically effective amount of one or more BKV-I capsid polypeptides (or fragments thereof) or one or more polynucleotides encoding the BKV-I capsid polypeptides and a therapeutically effective amount of one or more BKV-IV capsid polypeptides (or fragments thereof) or one or more polynucleotides encoding the BKV-IV capsid polypeptides is administered to the subject at doses of about 0.1 µg to 10 mg of each BKV capsid polypeptide or polynucleotide encoding the polypeptide or about 20-40 µg VLP per type for pentamers. However, the particular dose can be determined by a skilled clinician. The disclosed BKV capsid polypeptides (or a fragment thereof) or polynucleotide encoding the BKV capsid polypeptides or fragment thereof can be administered in one or several doses, for example continuously, daily, weekly, or monthly. When administered sequentially, the time separating the administration can be seconds, minutes, hours, days, or even weeks.

The mode of administration can be any used in the art, including but not limited to subcutaneous or intramuscular administration. The amount of agent administered to the subject can be determined by a clinician, and may depend on the particular subject treated. Specific exemplary amounts are provided herein (but the disclosure is not limited to such doses).

The development of immune response (such as development of antibodies, such as neutralizing antibodies) in a subject is monitored at time points following administration of the immunogenic composition. Methods of detecting antibodies in a sample (such as a blood or serum sample) include those known in the art, for example, ELISA methods. In some examples, the development of neutralizing antibodies to a BKV-Ia and/or BKV-Ib1 subtype and development of neutralizing antibodies to BKV-Ib2 subtype are monitored.

Example 8

Methods of Treating or Inhibiting PVAN

This example provides exemplary methods for treating or inhibiting PVAN in a subject. However, one of ordinary skill in the art will appreciate that methods that deviate from these specific methods can also be used to successfully treat or inhibit PVAN in a subject.

In particular examples, the method includes selecting a subject having, thought to have, or at risk of having PVAN. Subjects having or thought to have PVAN include those with >10 inclusion bearing epithelial cells ("decoy cells") in a urine sample per 10 high power fields, $>10^7$ BKV copies per 10 mL urine, or histopathological identification of viral alterations in a renal biopsy. Subjects at risk of PVAN include those who have had or are candidates for organ transplantation (such as renal transplant or bone marrow transplant), and immunocompromised individuals. In some examples, subjects who are candidates for renal transplant are selected. The selected subject can be a subject who does not have BKV-IV neutralizing antibodies.

Subjects selected for treatment are administered a therapeutically effective amount of a disclosed immunogenic composition. In some examples, a therapeutically effective amount of one or more BKV-IV capsid polypeptides or a polynucleotide encoding the BKV-IV capsid polypeptide(s) is administered to the subject at doses of about 0.1 μg to 10 mg of each BKV-IV capsid polypeptide or polynucleotide encoding the polypeptide or about 20-40 μg VLP per type for pentamers. However, the particular dose can be determined by a skilled clinician. The disclosed BKV-IV capsid polypeptides (or a fragment thereof) or polynucleotide encoding the BKV-IV capsid polypeptides or fragment thereof can be administered in one or several doses, for example continuously, daily, weekly, or monthly, with at least one dose at least 2 weeks prior to transplant. When administered sequentially, the time separating the administration can be seconds, minutes, hours, days, or even weeks.

The mode of administration can be any used in the art, including but not limited to subcutaneous or intramuscular administration. The amount of agent administered to the subject can be determined by a clinician, and may depend on the particular subject treated. Specific exemplary amounts are provided herein (but the disclosure is not limited to such doses).

The development of immune response (such as development of antibodies, such as neutralizing antibodies) in a subject is monitored at time points following administration of the immunogenic composition. Methods of detecting antibodies in a sample (such as a blood or serum sample) include those known in the art, for example, ELISA methods. A renal transplant is performed after an immune response is detected. The subject is also monitored for development of PVAN, for example by testing for presence of virus in urine or renal biopsy.

Example 9

Methods of Identifying a Renal Transplant Donor

This example provides exemplary methods for identifying a renal transplant donor, such as an individual who does not have serum antibodies capable of neutralizing one or more BKV types. However, one of ordinary skill in the art will appreciate that methods that deviate from these specific methods can also be used to successfully identify a renal transplant donor.

A blood sample is collected from a subject who is considered a possible renal transplant donor. Serum is prepared from the sample and serial dilutions of the serum are prepared (e.g., ten serial dilutions of four-fold ranging from 1:100 to $2.6\times10^7$). The diluted serum is mixed with a diluted BKV reporter vector carrying a reporter plasmid encoding *Gaussia princeps* luciferase under the control of a human elongation factor 1 alpha promoter and incubated on ice or at 4° C. for 1 hour. Then, the virus/serum mixture is added to 293TT cells plated in a 96-well plate at $3\times10^4$ cells/well. After 3 days, 25 μl of conditioned medium is collected and transferred to a luminometry plate. *Gaussia luciferase* substrate (50 μl NEB *Gaussia luciferase* assay kit substrate) is added and light emission is detected using a luminometer. Effective concentration 50% ($EC_{50}$) is calculated for the serum dilution series. An $EC_{50}$ of less than 100 indicates that the subject does not have BKV-IV neutralizing antibodies. A subject who does not have BKV-IV neutralizing antibodies is selected as a renal transplant donor.

A candidate renal transplant recipient can also be screened for the presence of BKV-IV neutralizing antibodies as described above. A candidate renal transplant recipient who is negative for BKV-IV neutralizing antibodies is considered a good candidate for receiving a kidney from a renal transplant donor who is negative for BKV-IV neutralizing antibodies.

Similar screening can be done for the presence of other BKV type-specific neutralizing antibodies in potential renal transplant donors and/or recipients. A potential renal transplant donor who does not have particular type-specific (such as BKV-I, BKV-II, or BKV-III) neutralizing antibodies is identified and selected as a renal transplant donor, particularly for a renal transplant recipient who also does not have the same type-specific neutralizing antibodies.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of eliciting a genotype-specific neutralizing antibody response against BK polyomaviruses (BKV) in a subject seropositive for BKV-Ia neutralizing antibodies but not for BKV-Ib2 neutralizing antibodies, comprising administering to the subject:
   - a therapeutically effective amount of an isolated BKV-Ib2 capsid polypeptide or a nucleic acid encoding the BKV-Ib2 capsid polypeptide; and
   - a therapeutically effective amount of at least one isolated BKV genotype IV (BKV-IV) capsid polypeptide or a nucleic acid encoding the at least one BKV-IV capsid polypeptide, thereby eliciting both BKV-Ib2-specific neutralizing antibodies and BKV-IV-specific neutralizing antibodies in the subject.

2. The method of claim 1, wherein the BKV-Ib2 capsid polypeptide and the at least one BKV-IV capsid polypeptide are administered concurrently or sequentially.

3. The method of claim 1, wherein:
   - administering the isolated BKV-Ib2 capsid polypeptide comprises administering a virus-like particle comprising the BKV-Ib2 capsid polypeptide; and/or
   - administering the at least one isolated BKV-IV capsid polypeptide comprises administering a virus-like particle comprising the at least one BKV-IV capsid polypeptide.

4. The method of claim 1, wherein:
   - the at least one BKV-IV capsid polypeptide comprises BKV-IV VP1, BKV-IV VP2, BKV-IV VP3 or a combination of two or more thereof.

5. The method of claim 4, wherein:
   - the BKV-IV VP1 polypeptide comprises one or more of a BKV subtype IVb VP1 polypeptide and a BKV subtype IVc VP1 polypeptide.

6. The method of claim 1, wherein:
   - the at least one isolated BKV-IV capsid polypeptide comprises the amino acid sequence of any one of SEQ ID NOs: 4-6, 16, and 110-125; and/or
   - the BKV-Ib2 capsid polypeptide comprises the amino acid sequence of SEQ ID NOs: 14 or 75-93.

7. The method of claim 1, further comprising:
   - administering to the subject a therapeutically effective amount of at least one isolated BKV genotype II (BKV-II) capsid polypeptide or a nucleic acid encoding the at least one BKV-II capsid polypeptide, thereby eliciting BKV-II neutralizing antibodies; and/or
   - administering to the subject a therapeutically effective amount of at least one isolated BKV genotype III (BKV-III) capsid polypeptide or a nucleic acid encoding the at least one BKV-III capsid polypeptide, thereby eliciting BKV-III neutralizing antibodies, wherein the BKV-II capsid polypeptide and the BKV-III capsid polypeptide are different.

8. The method of claim 1, further comprising administering to the subject a therapeutically effective amount of at least one isolated JC polyomavirus capsid polypeptide or a nucleic acid encoding the at least one JC polyomavirus capsid polypeptide.

9. The method of claim 1, further comprising administering an adjuvant to the subject.

10. The method of claim 1, wherein the subject is an immunocompromised subject, a subject who has been treated with or is a candidate for treatment with an immunosuppressant, or a subject who has received, or is a candidate for an organ transplant.

11. The method of claim 1, wherein the subject does not have BKV-Ib2-specific neutralizing antibodies and/or BKV-IV-specific neutralizing antibodies.

12. A method of eliciting a genotype-specific neutralizing antibody response against a BK polyomavirus (BKV) in a subject, comprising administering to a subject seropositive for BKV-Ia neutralizing antibodies but not for BKV-Ib2 neutralizing antibodies:
   - a therapeutically effective amount of an isolated BKV-Ib2 capsid polypeptide or a nucleic acid encoding the BKV-Ib2 capsid polypeptide;
   - a therapeutically effective amount of at least one isolated BKV genotype II (BKV-II) capsid polypeptide or a nucleic acid encoding the at least one BKV-II capsid polypeptide and
   - a therapeutically effective amount of at least one isolated BKV genotype IV (BKV-IV) capsid polypeptide or a nucleic acid encoding the at least one BKV-IV capsid polypeptide, wherein the at least one BKV-I capsid polypeptide, the at least one BKV-II capsid polypeptide, and the at least one BKV-IV capsid polypeptide are different, thereby eliciting BKV-I-specific neutralizing antibodies, BKV-II neutralizing antibodies, and BKV-IV-specific neutralizing antibodies.

13. The method of claim 12, further comprising: administering to the subject a therapeutically effective amount of at least one isolated BKV genotype III (BKV-III) capsid polypeptide or a nucleic acid encoding the at least one BKV-III capsid polypeptide, thereby eliciting BKV-III neutralizing antibodies.

14. The method of claim 12, wherein the BKV-Ib2 capsid polypeptide, the at least one BKV-II capsid polypeptide, and the at least one BKV-IV capsid polypeptide are administered concurrently or sequentially.

15. The method of claim 12, wherein:

administering the BKV-Ib2 capsid polypeptide comprises administering a virus-like particle comprising the at least one BKV-Ib2 capsid polypeptide;

administering the at least one isolated BKV-II capsid polypeptide comprises administering a virus-like particle comprising the at least one BKV-II capsid polypeptide; and/or administering the at least one isolated BKV-IV capsid polypeptide comprises administering a virus-like particle comprising the at least one BKV-IV capsid polypeptide.

16. The method of claim 12, wherein:

the isolated-BKV-Ib2 capsid polypeptide comprises BKV-Ib2 VP1, BKV-Ib2 VP2, BKV-Ib2 VP3, or a combination of two or more thereof;

the at least one BKV-II capsid polypeptide comprises BKV-II VP1, BKV-II VP2, BKV-II VP3 or a combination of two or more thereof; and/or the at least one BKV-IV capsid polypeptide comprises BKV-IV VP1, BKV-IV VP2, BKV-IV VP3 or a combination of two or more thereof.

17. The method of claim 16, wherein:

the BKV-IV VP1 polypeptide comprises one or more of a BKV subtype IVb VP1 polypeptide and a BKV subtype IVc VP1 polypeptide.

18. The method of claim 12, wherein:

the at least one isolated BKV-IV capsid polypeptide comprises the amino acid sequence of any one of SEQ ID NOs: 4-6, 16, and 110-125; and/or the at least one isolated BKV-Ib2 capsid polypeptide comprises the amino acid sequence of one of SEQ ID NOs: 14 or 75-93; and/or the at least one isolated BKV-II capsid polypeptide comprises the amino acid sequence of any one of SEQ ID NOs:7-9.

19. The method of claim 12, further comprising administering to the subject a therapeutically effective amount of at least one isolated JC polyomavirus capsid polypeptide or a nucleic acid encoding the at least one JC polyomavirus capsid polypeptide.

20. The method of claim 12, further comprising administering an adjuvant to the subject.

21. The method of claim 12, wherein the subject is an immunocompromised subject, a subject who has been treated with or is a candidate for treatment with an immunosuppressant, or a subject who has received, or is a candidate for an organ transplant.

22. The method of claim 21, wherein the subject has received, or is a candidate for a kidney transplant or a bone marrow transplant.

23. The method of claim 10, wherein the subject has received, or is a candidate for a kidney transplant or a bone marrow transplant.

24. The method of claim 1, wherein the isolated BKV-Ib2 capsid polypeptide comprises the amino acid sequence of SEQ ID NO: 90.

25. The method of claim 12, wherein the isolated BKV-Ib2 capsid polypeptide comprises the amino acid sequence of SEQ ID NO: 90.

* * * * *